United States Patent
Mallick

(10) Patent No.: US 11,970,693 B2
(45) Date of Patent: Apr. 30, 2024

(54) METHODS OF SELECTING BINDING REAGENTS

(71) Applicant: Nautilus Subsidiary, Inc., San Carlos, CA (US)

(72) Inventor: Parag Mallick, San Mateo, CA (US)

(73) Assignee: NAUTILUS SUBSIDIARY, INC., Seattle, WA (US)

( * ) Notice: Subject to any disclaimer, the term of this patent is extended or adjusted under 35 U.S.C. 154(b) by 0 days.

(21) Appl. No.: 16/791,456

(22) Filed: Feb. 14, 2020

(65) Prior Publication Data

US 2020/0318101 A1 Oct. 8, 2020

Related U.S. Application Data

(63) Continuation of application No. PCT/US2018/000364, filed on Aug. 20, 2018.

(60) Provisional application No. 62/547,699, filed on Aug. 18, 2017.

(51) Int. Cl.
*C12N 15/10* (2006.01)
*G01N 33/68* (2006.01)

(52) U.S. Cl.
CPC ..... *C12N 15/1055* (2013.01); *G01N 33/6845* (2013.01)

(58) Field of Classification Search
None
See application file for complete search history.

(56) References Cited

U.S. PATENT DOCUMENTS

| | | | |
|---|---|---|---|
| 5,324,633 A | 6/1994 | Fodor et al. |
| 5,445,934 A | 8/1995 | Fodor et al. |
| 5,695,934 A | 12/1997 | Brenner |
| 5,849,878 A | 12/1998 | Cantor et al. |
| 5,863,722 A | 1/1999 | Brenner |
| 5,888,737 A | 3/1999 | DuBridge et al. |
| 5,919,626 A | 7/1999 | Shi et al. |
| 6,140,489 A | 10/2000 | Brenner |
| 6,175,002 B1 | 1/2001 | DuBridge et al. |
| 6,391,625 B1 | 5/2002 | Park et al. |
| 6,589,726 B1 | 7/2003 | Butler et al. |
| 6,610,482 B1 | 8/2003 | Fodor et al. |
| 6,720,595 B2 | 4/2004 | Clevenger et al. |
| 6,806,361 B1 | 10/2004 | Kajisa et al. |
| 6,824,866 B1 | 11/2004 | Glazer et al. |
| 6,998,241 B2 | 2/2006 | Boga |
| 7,022,515 B2 | 4/2006 | Herron et al. |
| 7,148,058 B2 | 12/2006 | Charych et al. |
| 7,158,224 B2 | 1/2007 | Montagu |
| 7,239,860 B2 | 7/2007 | Stoks |
| 7,252,954 B2 | 8/2007 | Wang et al. |
| 7,545,496 B2 | 6/2009 | Prins et al. |
| 7,635,562 B2 | 12/2009 | Harris et al. |
| 7,794,799 B1 | 9/2010 | Kim et al. |
| 7,842,793 B2 | 11/2010 | Rothemund |
| 7,932,060 B2 | 4/2011 | Nadeau et al. |
| 8,133,719 B2 | 3/2012 | Drmanac et al. |
| 8,467,061 B2 | 6/2013 | McCaffrey et al. |
| 8,501,923 B2 | 8/2013 | Rothemund |
| 8,680,483 B2 | 3/2014 | Haga et al. |
| 8,865,077 B2 | 10/2014 | Chiou et al. |
| 8,951,781 B2 | 2/2015 | Reed et al. |
| 9,193,996 B2 | 11/2015 | Buermann et al. |
| 9,340,416 B2 | 5/2016 | Maune et al. |
| 9,528,984 B2 | 12/2016 | Mitra |
| 9,606,058 B2 | 3/2017 | Rothberg et al. |
| 9,678,012 B2 | 6/2017 | Rothberg et al. |
| 9,880,175 B2 | 1/2018 | Mitra |
| 9,921,157 B2 | 3/2018 | Rothberg et al. |
| 10,175,248 B2 | 1/2019 | Mitra |
| 10,330,598 B2 | 6/2019 | Schleipen et al. |
| 10,351,909 B2 | 7/2019 | Drmanac et al. |
| 10,473,654 B1 | 11/2019 | Mallick |
| 10,571,473 B2 | 2/2020 | Mitra |
| 10,605,730 B2 | 3/2020 | Rothberg et al. |
| 10,712,274 B2 | 7/2020 | Rothberg et al. |
| 10,741,382 B2 | 8/2020 | Sills et al. |
| 10,775,305 B2 | 9/2020 | Rothberg et al. |
| 10,829,816 B2 | 11/2020 | Staker et al. |
| 10,845,308 B2 | 11/2020 | Rothberg et al. |
| 10,895,534 B2 | 1/2021 | Finkelstein et al. |
| 10,921,317 B2 | 2/2021 | Mallick |
| 10,948,488 B2 | 3/2021 | Mallick |

(Continued)

FOREIGN PATENT DOCUMENTS

| CN | 100500865 C | 6/2009 |
|---|---|---|
| EP | 1105529 B2 | 5/2013 |

(Continued)

OTHER PUBLICATIONS

Reineke (2009 Methods of Molecular Biology, Epitope Mapping Protocols vol. 524) (Year: 2009).*
Reineke et al.(Methods in Molecular Biology, Epitope Mapping Protocols 524:145-167) (Year: 2009).*
3-Aminopropyl)triethoxysilane. Wikipedia.org. Apr. 5, 2019 (Apr. 5, 2019), entire document esp p. 1 (https://en.wikipedia.org/w/index.php?title=(3- Aminopropyl)triethoxysilaneoldid=891131780).
Arnold et al. "The majority of immunogenic epitopes generate CD44-T cells that are dependent on MHC class II-bound peptide-flanking residues," J Immunol, Jul. 15, 2002 (Jul. 15, 2002), vol. 169, No. 2, pp. 739-749.

(Continued)

*Primary Examiner* — Christopher M Gross
(74) *Attorney, Agent, or Firm* — Orrick, Herrington & Sutcliffe LLP

(57) ABSTRACT

Methods and systems are provided herein for selecting an affinity reagent which binds a desired peptide epitope in a plurality of sequence contexts. The method relies on obtaining a peptide library, each peptide having the sequence $\alpha X \beta$, wherein X is the desired peptide epitope, wherein each of $\alpha$ and $\beta$ comprise an amino acid, using the peptide library to select an affinity reagent.

23 Claims, 14 Drawing Sheets

Specification includes a Sequence Listing.

(56) References Cited

U.S. PATENT DOCUMENTS

| | | |
|---|---|---|
| 11,203,612 B2 | 12/2021 | Gremyachinskiy et al. |
| 2003/0054408 A1 | 3/2003 | Ravi et al. |
| 2004/0023413 A1 | 2/2004 | Opalsky |
| 2004/0091931 A1 | 5/2004 | Gold |
| 2004/0166106 A1 | 8/2004 | Wang et al. |
| 2004/0209383 A1 | 10/2004 | Yin et al. |
| 2005/0054118 A1 | 3/2005 | Lebrun |
| 2005/0095577 A1 | 5/2005 | Yang et al. |
| 2005/0287523 A1 | 12/2005 | Letant et al. |
| 2006/0035220 A1 | 2/2006 | Tashiro et al. |
| 2006/0160234 A1 | 7/2006 | Lopez-Avila et al. |
| 2006/0263769 A1 | 11/2006 | Luo et al. |
| 2007/0188750 A1 | 8/2007 | Lundquist et al. |
| 2007/0218503 A1 | 9/2007 | Mitra |
| 2009/0161100 A1 | 6/2009 | Minot et al. |
| 2009/0214591 A1 | 8/2009 | Manucharyan et al. |
| 2009/0247414 A1 | 10/2009 | Obradovic et al. |
| 2009/0257952 A1* | 10/2009 | Cochran ............... A61K 38/08 424/9.1 |
| 2009/0311774 A1 | 12/2009 | Chiou et al. |
| 2010/0111768 A1 | 5/2010 | Banerjee et al. |
| 2011/0065807 A1 | 3/2011 | Radovic-Moreno et al. |
| 2011/0263688 A1 | 10/2011 | Barany et al. |
| 2012/0077688 A1 | 3/2012 | Bergo et al. |
| 2013/0310274 A1 | 11/2013 | Meng et al. |
| 2015/0160204 A1 | 6/2015 | Mitra |
| 2015/0185199 A1 | 7/2015 | Joo et al. |
| 2015/0330974 A1 | 11/2015 | Staker et al. |
| 2016/0060687 A1 | 3/2016 | Zhu et al. |
| 2016/0102344 A1 | 4/2016 | Niemeyer et al. |
| 2016/0167413 A1 | 6/2016 | Furuya |
| 2016/0310926 A1 | 10/2016 | Sun et al. |
| 2017/0044245 A1* | 2/2017 | Meng ............... C07K 16/2803 |
| 2017/0175184 A1 | 6/2017 | Drmanac et al. |
| 2017/0191051 A1 | 7/2017 | Nikiforov |
| 2017/0283868 A1 | 10/2017 | Beechem et al. |
| 2019/0195869 A1 | 6/2019 | Fan et al. |
| 2019/0204339 A1 | 7/2019 | Mitra |
| 2020/0025752 A1 | 1/2020 | Gopinath et al. |
| 2020/0025757 A1 | 1/2020 | Gopinath et al. |
| 2020/0158722 A1 | 5/2020 | Mallick |
| 2020/0173988 A1 | 6/2020 | Mallick |
| 2020/0232994 A1 | 7/2020 | Mitra |
| 2021/0101930 A1 | 4/2021 | Gremyachinskiy et al. |
| 2022/0017567 A1 | 1/2022 | Gremyachinskiy et al. |
| 2022/0050049 A1 | 2/2022 | Indermuhle et al. |
| 2022/0074931 A1 | 3/2022 | Mallick |

FOREIGN PATENT DOCUMENTS

| | | | |
|---|---|---|---|
| EP | 2872898 | B1 | 12/2016 |
| EP | 3498865 | B1 | 10/2020 |
| JP | 2017504795 | A | 2/2017 |
| WO | WO1999/002733 | A1 | 1/1999 |
| WO | WO-0146675 | A2 | 6/2001 |
| WO | WO-02086081 | A2 | 10/2002 |
| WO | WO2003/099999 | A2 | 12/2003 |
| WO | WO-2006135527 | A2 | 12/2006 |
| WO | WO-2007117444 | A2 | 10/2007 |
| WO | WO-2007120208 | A3 | 8/2008 |
| WO | WO-2007123744 | A3 | 11/2008 |
| WO | WO-2009012343 | A2 | 1/2009 |
| WO | WO-2010065531 | A1 | 6/2010 |
| WO | WO-2014078855 | A1 | 5/2014 |
| WO | WO2015/034364 | A1 | 3/2015 |
| WO | WO-2015097077 | A2 | 7/2015 |
| WO | WO-2016174525 | A1 | 11/2016 |
| WO | WO-2017127762 | A1 | 7/2017 |
| WO | WO-2018102759 | A1 | 6/2018 |
| WO | WO-2019036055 | A2 | 2/2019 |
| WO | WO-2019195633 | | 10/2019 |
| WO | WO-2019236749 | A2 | 12/2019 |
| WO | WO-2020106889 | A1 | 5/2020 |
| WO | WO-2020108588 | A1 | 6/2020 |
| WO | WO-2020223368 | A1 | 11/2020 |

OTHER PUBLICATIONS

Ayoglu, et al., Autoantibody Profiling in Multiple Sclerosis Using Arrays of Human Protein Fragments, Molecular & Cellular Proteomics, (12)9 Sep. 1, 2013 (Sep. 1, 2013), pp. 2657-2672, XP055294116, US, ISSN: 1535-9476, DOI: 10.1074/mcp.M112.026757.

Blatch, et al. The tetratricopeptide repeat: a structural motif mediating protein-protein interactions. Bioessays Nov. 1999;21(11):932-939.

Buenrostro, et al. Quantitative analysis of RNA-protein interactions on a massively parallel array for mapping biophysical and evolutionary landscapes. Nat Biotechnol. Jun. 2014; 32(6): 562-568.

Bunka et al. "Production and characterization of RNA aptamers specific for amyloid fibril epitopes," J Biol Chem, Sep. 18, 2007 (Sep. 18, 2007), vol. 282, No. 47, pp. 34500-34509.

Buus, et al. High-resolution mapping of linear antibody epitopes using ultrahigh-density peptide microarrays. Molecular & Cellular Proteomics 11.12 (2012): 1790-1800.

Choung, et al. Determination of B-Cell Epitopes in Patients with Celiac Disease: Peptide Microarrays. PloS one vol. 11(1) e0147777. Jan. 29, 2016, doi: 10.1371/journal.pone.0147777.

Co-pending U.S. Appl. No. 16/760,032, inventors Chee; Mark S. et al., filed Apr. 28, 2020.

Co-pending U.S. Appl. No. 16/972,341, inventor Mallick; Parag, filed Dec. 4, 2020.

Co-pending U.S. Appl. No. 17/153,877, inventor Mallick; Parag, filed Jan. 20, 2021.

Co-pending U.S. Appl. No. 17/191,632, inventor M; Parag, filed Mar. 3, 2021.

Domenyuk, et al. Plasma Exosome Profiling of Cancer Patients by a Next Generation Systems Biology Approach. Sci Rep. 2017; 7: 42741.

EP17877076.4 The Extended European Search Report dated Aug. 11, 2020.

EP18846671.8 Extended European Search Report dated Apr. 23, 2021.

Fodor, et al. Light-Directed, Spatially Addressable Parallel Chemical Synthesis. Science, vol. 251, 767-773, 1991.

Ford et al. "Degenerate recognition of T cell epitopes: impact of T cell receptor reserve and stability of peptide:MHC complexes," Mol Immunol, Feb. 1, 2004 (Feb. 1, 2004), vol. 40, No. 14-15, pp. 1019-1025.

Hung, et al. Large-area spatially ordered arrays of gold nanoparticles directed by lithographically confined DNA origami. Nat Nanotechnol. Feb. 2010;5(2):121-6. doi: 10.1038/nnano.2009.450. Epub Dec. 20, 2009.

Hunniger, et al. Just in time-selection: A rapid semiautomated SELEX of DNA aptamers using magnetic separation and BEAMing. Anal Chem. Nov. 4, 2014;86(21): 10940-7.

Kang, H. The prevention and handling of the missing data. Korean journal of anesthesiology vol. 64,5 (2013): 402-6. doi:10.4097/kjae.2013.64.5.402.

Laurenson, et al. Development of peptide aptamer microarrays for detection of HPV16oncoproteins in cell extracts, Analytical Biochemistry, Academic Press, Amsterdam,NL, vol. 410, No. 2, Oct. 30, 2010 (Oct. 30, 2010), pp. 161-170, XP028146256, ISSN: 0003-2697, DOI: 10.1016/J.AB.2010.10.038.

Lin et al. Development of a novel peptide microarray for large-scale epitope mapping of food allergens, Journal of Allergy and Clinical Immunology, Elsevier, Amsterdam, Nl, vol. 124, No. 2, Aug. 1, 2009 (Aug. 1, 2009), pp. 315-322.e3, XP026390934, ISSN: 0091-6749, DOI: 10.1016/J.JACI.2009.05.024.

Lutz, et al. Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.

McKay, et al. Click Chemistry in Complex Mixtures: Bioorthogonal Bioconjugation. Chem Biol. Sep. 18, 2014; 21(9): 1075-1101.

(56) References Cited

OTHER PUBLICATIONS

Meldal, et al. Cu-catalyzed azide-alkyne cycloaddition. Chem Rev. Aug. 2008;108(8):2952-3015. doi: 10.1021/cr0783479.
Nonobe et al. A tabu search approach to the constraint satisfaction problem as a general problem solver. Eur. J. Oper. Res. 106 (1998): 599-623.
Patronov et al. "Peptide binding prediction for the human class II MHC allele HLA-DP2: a molecular docking approach," BMC Struct Biol, Jul. 14, 2011 (14.07.2011), vol. 11, No. 32, pp. 1-10.
PCT/US17/64322 International Search Report and Written Opinion dated Apr. 25, 2018.
PCT/US18/00364 International Search Report and Written Opinion dated Mar. 22, 2019.
PCT/US2019/025909 International Search Report and Written Opinion dated Jun. 14, 2019.
PCT/US2019/035654 International Search Report dated Nov. 25, 2019.
PCT/US2019/062482 International Search Report dated Mar. 3, 2020.
PCT/US2020/030501 International Search Report dated Aug. 11, 2020.
Price, et al., On silica peptide microarrays for high-resolution mapping of antibody epitopes and diverse protein-protein interactions, Nature Medicine, vol. 18, No. 9, Aug. 19, 2012, pp. 1434-1440, XP055793803, New York ISSN: 1078-8956, DOI: 10.1038/nm.2913Retrieved from the Internet:URL:http://www.nature.com/articles/nm.2913.
Reyes et al. "Critical role of HLA-DR11" binding peptides' peripheral flanking residues in fully-protective malaria vaccine development, Biochem Biophys Res Commun, May 23, 2017 (May 23, 2017), vol. 489, No. 3, pp. 339-345.
Richer, et al., Epitope identification from fixed-complexity random-sequence peptide microarrays, Molecular & cellular proteomics, vol. 14, No. 1, Nov. 3, 2014, pp. 136-147.
Rothemund, et al. Folding DNA to create nanoscale shapes and patterns. Nature. Mar. 16, 2006;440(7082):297-302.
Sant'Angelo et al. "Recognition of core and flanking amino acids of MHC class II-bound peptides by the T cell receptor," Eur J Immunol, Sep. 1, 2002 (Sep. 1, 2002), vol. 32, No. 9, pp. 2510-2520.
She, et al. Comprehensive and quantitative mapping of RNA-protein interactions across a transcribed eukaryotic genome. Proc Natl Acad Sci U S A. Apr. 4, 2017; 114(14): 3619-3624.
Sjoberg et al. Validation of affinity reagents using antigen microarrays, Newbiotechnology, vol. 29, No. 5, Jun. 1, 2012 pp. 555-563, XP055793929,NLISSN: 1871-6784, DOI: 10.1016/j.nbt.2011.11.009.
Speltz, et al. Design of Protein-Peptide Interaction Modules for Assembling Supramolecular Structures in Vivo and in Vitro. ACS Chem Biol. Sep. 18, 2015;10(9):2108-15. doi: 10.1021/acschembio.5b00415. Epub Jul. 17, 2015.
Stöhr, et al. A 31-residue peptide induces aggregation of tau's microtubule-binding region in cells. Nat Chem. Sep. 2017; 9(9): 874-881. Published online Apr. 3, 2017.doi: 10.1038/nchem.2754.
Tessler, L. Digital Protein Analysis: Technologies for Protein Diagnostics and Proteomics through Single-Molecule Detection (2011). All Theses and Dissertations (ETDs). 346 https://openscholarship.wustl.edu/etd/346.
U.S. Appl. No. 16/659,132 Notice of Allowance dated Jan. 14, 2021.
U.S. Appl. No. 16/659,132 Office Action dated Oct. 8, 2020.
U.S. Appl. No. 16/788,536 Notice of Allowance dated Dec. 9, 2020.
U.S. Appl. No. 16/788,536 Office Action dated Mar. 10, 2020.
U.S. Appl. No. 16/788,536 Office Action dated Sep. 24, 2020.
U.S. Appl. No. 17/062,405 Office Action dated Apr. 14, 2021.
U.S. Appl. No. 17/191,632 Office Action dated May 12, 2021.
U.S. Appl. No. 16/426,917 Notice of Allowance dated Oct. 1, 2019.
Wilson, et al. Single-Step Selection of Bivalent Aptamers Validated by Comparison with SELEX Using High-Throughput Sequencing. PLoS One. 2014; 9(6): e100572.
Zandian, Arash et al. Whole-Proteome Peptide Microarrays for Profiling Autoantibody Repertoires within Multiple Sclerosis and Narcolepsy. Journal of proteome research 16(3) 2017: 1300-1314. doi: 10.1021/acs.jproteome.6b00916.
Co-pending U.S. Appl. No. 17/496,742, inventors Gremyachinskiy; Dmitriy et al., filed Oct. 7, 2021.
U.S. Appl. No. 17/191,632 Examiner's Interview Summary dated Nov. 9, 2021.
Co-pending U.S. Application No. 202117390666, inventor Mallick; Parag, filed on Jul. 30, 2021.
Co-pending U.S. Application No. 202117424435, inventors Klein; Joshua et al., filed on Jul. 20, 2021.
Riccelli, et al. Hybridization of single-stranded DNA targets to immobilized complementary DNA probes: comparison of hairpin versus linear capture probes. Nucleic acids research vol. 29,4 (2001): 996-1004. doi:10.1093/nar/29.4.996.
U.S. Appl. No. 17/062,405 Final Office Action dated Aug. 24, 2021.
U.S. Appl. No. 17/062,405 Notice of Allowance dated Sep. 30, 2021.
U.S. Appl. No. 17/191,632 Final Office Action dated Sep. 17, 2021.
Anonymous. List of protein hydrodynamic diameters. Dynamic Biosensors. May 17, 2017, XP055857934, Available at https://www.dynamic-biosensors.com/project/list-of-protein-hydrodynamic-diameters/. Retrieved on Nov. 4, 2021.
EP19781106.0 Extended European Search Report dated Nov. 19, 2021.
Rusmini, Federica et al. Protein immobilization strategies for protein biochips. Biomacromolecules vol. 8,6 (2007): 1775-89. doi:10.1021/bm061197b.
U.S. Appl. No. 17/390,666 Office Action dated Jan. 28, 2022.
Office Action for Chinese Patent Application No. 2018800681790 with English translation, 10 pages, dated Feb. 24, 2023.
Office Action for Japanese Patent Application No. 2020-509044 with English translation, 3 pages, dated Jan. 24, 2023.
EP3884048 European Search Report dated Jul. 15, 2022.
Office Action in Chinese Application No. 201880068179.0, mailed Sep. 22, 2023, 21 pages.
Ogawa et al., "Aptamer selection for the inhibition of cell adhesion with fibronectin as target." Bioorganic & Medicinal Chemistry Letters 14 (2004), Elsevier, Jun. 15, 2004, pp. 4001-4004.

\* cited by examiner

```
                       SEQUENCE LISTING

<160> NUMBER OF SEQ ID NOS: 31

<210> SEQ ID NO 1
    <211> LENGTH: 10
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 1

Glu Gln Lys Leu Ile Ser Glu Glu Asp Leu
    1               5                   10

<210> SEQ ID NO 2
    <211> LENGTH: 5
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 2

Ala Ala Ala Ala Ala
    1               5

<210> SEQ ID NO 3
    <211> LENGTH: 5
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 3

Ala Ala Ala Ala Cys
    1               5

<210> SEQ ID NO 4
    <211> LENGTH: 5
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 4

Cys Ala Ala Ala Ala
    1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Ala Ala Ala Cys
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Ala Ala Ala Asp
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Arg Asp Glu Tyr Trp Cys
1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ala Lys Asp
1

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Ala Ala Ala Leu
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 10

Tyr Ala Ala Ala Ser
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Ala Ala Ala Thr
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ala Ala Ala Asp
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Ala Ala Ala Ala
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Ala Ala Ala Cys
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Ala Ala Ala Asp
1               5

<210> SEQ ID NO 16
<211> LENGTH: 5
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 16

Tyr Ala Ala Ala Tyr
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Arg Leu Leu Gly
1               5

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 18 nntgactcan                                                            10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (9)..(10)
<223> OTHER INFORMATION: a, c, t, g, unknown or other

<400> SEQUENCE: 19 natgactcnn                                                            10

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:

```
<221> NAME/KEY: modified_base
<222> LOCATION: (10)..(10)
<223> OTHER INFORMATION: a, c, t, g, unknown or other

<400> SEQUENCE: 20 nntgactaan                                                                     10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (9)..(10)
<223> OTHER INFORMATION: a, c, t, g, unknown or other

<400> SEQUENCE: 21 ngtgactcnn                                                                     10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(10)
<223> OTHER INFORMATION: a, c, t, g, unknown or other

<400> SEQUENCE: 22 tatgactnnn                                                                     10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (9)..(10)
<223> OTHER INFORMATION: a, c, t, g, unknown or other

<400> SEQUENCE: 23 natgactann                                                                     10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
```

```
<220> FEATURE:
<221> NAME/KEY: modified_base
<222> LOCATION: (9)..(10)
<223> OTHER INFORMATION: a, c, t, g, unknown or other

<400> SEQUENCE: 24 natgactgnn                                                                10

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other

<400> SEQUENCE: 25 nnngactcat                                                                10

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(10)
<223> OTHER INFORMATION: a, c, t, g, unknown or other

<400> SEQUENCE: 26 gatgactnnn                                                                10

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (9)..(10)
<223> OTHER INFORMATION: a, c, t, g, unknown or other

<400> SEQUENCE: 27 natgacacnn                                                                10

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other

<400> SEQUENCE: 28
```

```
nnnagctacc                                                              10

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (9)..(10)
<223> OTHER INFORMATION: a, c, t, g, unknown or other

<400> SEQUENCE: 29 ngatactann                                                              10

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other

<400> SEQUENCE: 30 nnntcctaac                                                              10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (9)..(10)
<223> OTHER INFORMATION: a, c, t, g, unknown or other

<400> SEQUENCE: 31 natgaatgnn                                                              10
```

METHODS OF SELECTING BINDING REAGENTS

CROSS-REFERENCE

This application is a Continuation Application of International Application No. PCT/US2018/000364, filed Aug. 20, 2018, which claims the benefit of U.S. Provisional Application No. 62/547,699, filed Aug. 18, 2017, which application is incorporated herein by reference.

SEQUENCE LISTING

The instant application contains a Sequence Listing which has been submitted electronically in ASCII format and is hereby incorporated by reference in its entirety. Said ASCII copy, created on May 4, 2020, is named 51612-703_301_SL.txt and is 8,871 bytes in size.

BACKGROUND OF THE INVENTION

Selection methods for the generation of binding reagents are typically designed to select for binding reagents with high affinity and specificity for a single epitope or protein. For some applications it may be useful to select binding reagents which bind multiple epitopes, or to characterize the binding patterns of binding reagents which are not specific for a single protein or epitope.

SUMMARY OF THE INVENTION

The present disclosure provides methods and systems for selecting and characterizing affinity reagents. In some embodiments, the present disclosure provides approaches in which an affinity reagent is selected to bind to an epitope in a variety of sequence contexts. Methods and systems described herein may also be used to characterize the binding pattern of an affinity reagent, and the effects of sequence context on the binding of the affinity reagent to an epitope. Additionally, methods and systems described herein may be used to characterize and select affinity reagents that bind across multiple epitopes, such as binding across multiple epitopes having a same length. By demonstrating promiscuity across multiple epitopes of a same length, a particular affinity reagent may be used in identifying sequences as containing at least one epitope of the multiple epitope to which the particular affinity reagent binds.

An aspect of the invention provides a method for choosing an affinity reagent which binds a desired peptide epitope in a plurality of sequence contexts. The method comprises obtaining a peptide library, each peptide having the sequence $\alpha X \beta$ and a length k, wherein X is the desired peptide epitope of length m. The method also comprises exposing the peptide library to a plurality of a particular affinity reagent. The method also comprises determining which peptides within the peptide library are bound by the particular affinity reagent. Additionally, the method comprises using the peptide library to choose the particular affinity reagent if the particular affinity reagent is bound to more than a threshold number of peptides within the peptide library.

An aspect of the invention provides a method for selecting an affinity reagent which binds a desired peptide epitope in a plurality of sequence contexts. The method comprises obtaining a peptide library, each peptide having the sequence $\alpha X \beta$, wherein X is the desired peptide epitope, and wherein each of $\alpha$ and $\beta$ comprise an amino acid; and using the peptide library to select an affinity reagent. In some cases, each of $\alpha$ and $\beta$ consists of one amino acid. In some cases, at least one of $\alpha$ and $\beta$ comprises a linker. In some cases, at least one of $\alpha$ and $\beta$ comprises a modification. In some cases, a plurality of affinity reagents are selected using the method herein. In some cases, the desired peptide epitope X is between 2 and 7 amino acids. In some cases, the selected affinity reagent is an aptamer. In some cases, the selected affinity reagent is an antibody. In some cases, the method further comprises characterizing the binding of the selected affinity reagent by screening the selected affinity reagent against a plurality of peptides of the same length of the desired epitope. In some cases, the plurality of peptides of the same length of the desired epitope is representative of 90% of all possible variations of peptides of the same length of the desired epitope. In some cases, the method further comprises characterizing the binding of the selected affinity reagent by screening the selected affinity reagent against a plurality of peptides, wherein each peptide of the plurality of peptides comprises the desired epitope and one or more flanking residues. In some cases, the method further comprises characterizing the binding of the selected affinity reagent by screening the selected affinity reagent against a second plurality of peptides, wherein each peptide of the plurality of peptides comprises a secondary epitope, that was identified in a characterizing step, and one or more flanking residues. In some cases, the method further comprises characterizing the binding of the selected affinity reagent by screening the selected affinity reagent against a plurality of subsets of a plurality of peptides shorter than the desired epitope. In some cases, the method further comprises characterizing the selected affinity reagent by screening the selected affinity reagent against a panel of proteins which contain the three amino acid epitope. In some cases, the selected affinity reagent is retained if it binds to greater than about 10%, 20%, 30%, 40%, 60%, 75%, or 90% of the proteins. In some cases, the method further comprises characterizing the selected affinity reagent by screening the selected affinity reagent against a panel of proteins which do not contain the three amino acid epitope. In some cases, the selected affinity reagent is retained if it binds to less than about 15%, 10%, 5%, 1%, 0.1%, or 0.01% of the proteins.

In some cases, the selected affinity reagent is screened against a library of random peptides having a length between 2 and 10 amino acids, and further comprising: identifying the peptides bound by the selected affinity reagent; and retaining the selected affinity reagent if 1) it binds less than, or equal to, a number of epitopes determined by the equation $20*(k-2)$, where k is the length of a central epitope, and 2) it binds at least 10% of all longer peptides containing that epitope. As affinity reagents are selected based on their ability to bind to a particular central epitope of length k, it is noted that the percentage of the proteome that is able to bind to a particular affinity reagent will generally decrease as the length k of a particular central epitope increases. While there are some embodiments where it is beneficial to select affinity reagents that bind to a large percentage of the proteome, and therefore there are benefits to identifying affinity reagents that may have a smaller length k of a central epitope, it may also be beneficial to identify and select affinity reagents that are more specific, even though they may cover a smaller percentage of the proteome. In particular, it may be beneficial to use selected affinity reagents in pools that are designed to address different scenarios of protein identifications. For example, if selected affinity reagents are able to quickly distinguish between a small number of candidate proteins that are narrowed down using other methods, those selected affinity reagents may be very beneficial to use in a set of pooled affinity reagents.

In some cases, the selected affinity reagent is not retained unless it binds at least 15%, 20%, 30%, 40%, 50%, 75%, 90%, or 95% of all longer peptides containing the epitope. In some cases, the method further comprises characterizing the binding of the affinity reagent by screening the affinity reagent against a library of peptides, the library of peptides comprising peptides shorter than the desired epitope, peptides of the same length of the desired epitope, and peptides longer than the desired epitope; and identifying the sequences of bound peptides, thereby characterizing the binding of the affinity reagent. In some cases, the affinity reagents are immobilized to one or more substrates, such as solid supports, and wherein the library of random peptides is passed over the immobilized affinity reagents. In some cases affinity reagents are immobilized, in other cases targets are immobilized. In some cases, a solid support may be a bead. An aspect of the invention provides a method of selecting an affinity reagent from a set of affinity reagents, comprising screening the set of affinity reagents against a library of random peptides having a length between 2 and 10 amino acids; identifying peptides bound by each affinity reagent of the set of affinity reagents; and selecting an affinity reagent that 1) binds less than 20 different epitopes and that 2) binds at least 10% of all longer peptides containing that epitope. In some cases, the affinity reagent is not selected unless it binds at least 15%, 20%, 30%, 40%, 50%, 75%, 90%, or 95% of all longer peptides containing the epitope. An aspect of the invention provides an affinity reagent which specifically binds an amino acid epitope, does not bind to more than nineteen other amino acid epitopes, and binds at least 10% of sequences of the form $\alpha X\beta$, wherein X is the desired epitope and $\alpha$ and $\beta$ are any amino acid residues. In some cases, the affinity reagent binds at least 0.25%, 0.5%, 0.75%, 1%, 2%, 3%, 4%, 5%, 6%, 7%, 8%, 9%, 10%, 11%, 12%, 13%, 14%, 15%, 20%, 30%, 40%, 50%, 75%, or 90% of sequences of the form $\alpha X\beta$.

An aspect of the invention provides an affinity reagent which specifically binds a three amino acid epitope, does not bind any other three amino acid epitopes, and binds the desired epitope with substantially similar affinity regardless of flanking sequence surrounding the desired epitope. In some cases, the affinity reagent does not bind a subset of the epitope. Another aspect of the invention provides an affinity reagent which preferentially binds a known set of three amino acid epitopes for which the preference for these epitopes relative to other epitopes, and subject to flanking residues, has been determined.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 discloses SEQ ID NOS 9-11, 2-3, 12, 4-5, and 13-16, respectively, in order of appearance.

FIG. 3B discloses SEQ ID NOS 2, 2, 2-3, 3, 3, 2-3, 12, 4-5, and 13-16, respectively, in order of appearance.

FIG. 5A illustrates examples of peptides forming alpha helices with embedded targets (shown as checked boxes) in different regions of the alpha helical peptide, in accordance with some embodiments. FIG. 5B illustrates examples of peptides forming beta sheets with embedded targets (shown as solid black boxes) in different regions of the beta sheet forming peptide, in accordance with some embodiments.

DETAILED DESCRIPTION OF THE INVENTION

Figure 1:
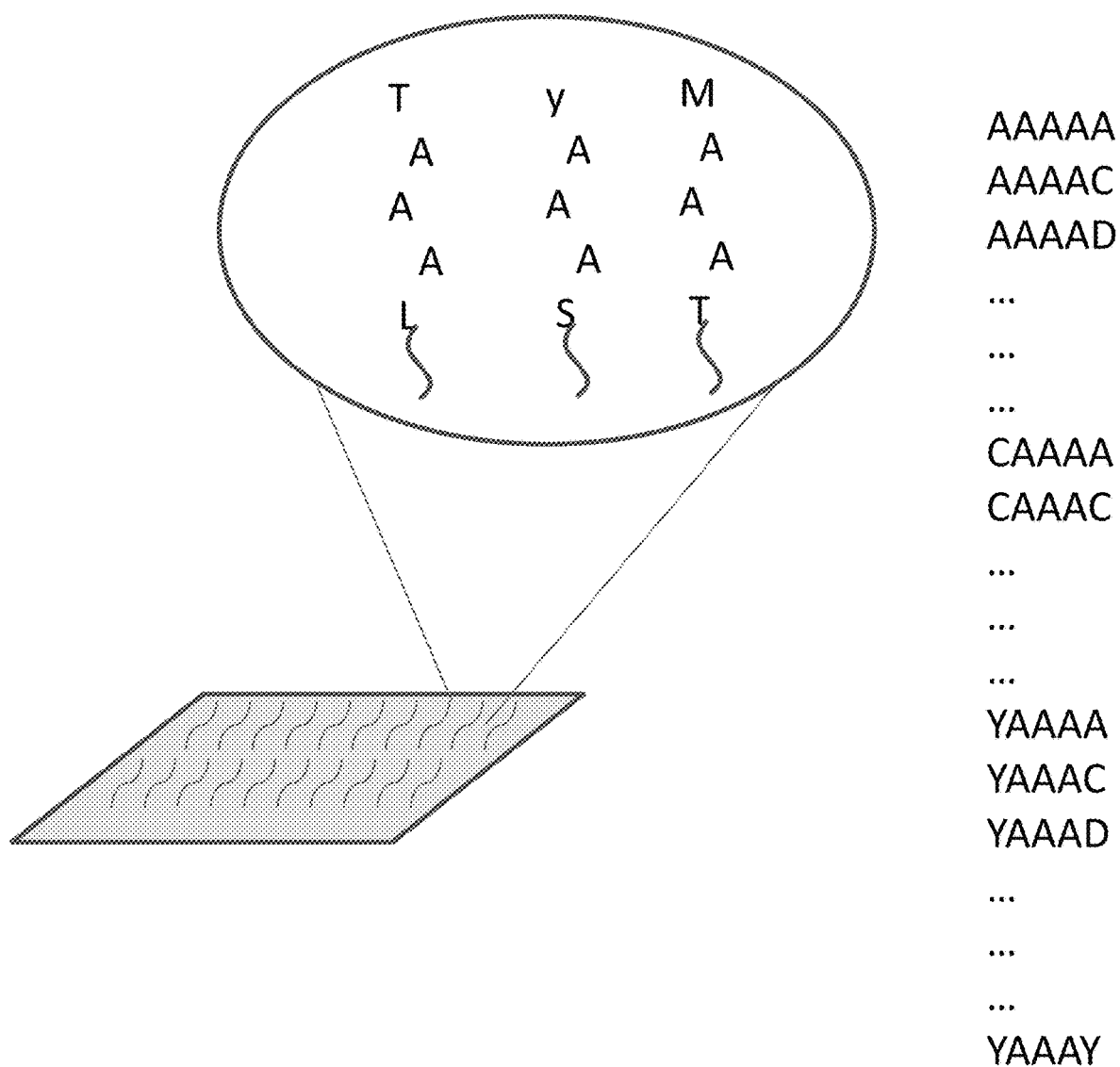
FIG. 1 illustrates an immobilized target for selection of affinity reagents, along with an exemplary list of peptides which comprise the target, in accordance with some embodiments.

Throughout the life sciences there has been substantial interest in the development of affinity reagents that are able to bind to specific proteins, metabolites, cells or cell interfaces. More recently, affinity reagent selection techniques have been extended to include non-natural nucleotides and amino acids. The objective of these approaches has been to develop reagents that bind exclusively to a given epitope.

Exclusivity of binding is considered to be a desirable trait in an affinity reagent. Substantial efforts are made to ensure that the affinity reagent binds to just one protein, with minimal binding to other proteins. Exceptions to this are antibodies raised against functionally important residues, such as phospho-tyrosines.

One particular challenge faced by affinity reagents may be context sensitivity. For example, affinity reagents may bind perfectly to a core epitope, but may be biased to binding well or not binding at all depending upon flanking residues. For example, when generating an affinity reagent against a peptide n-Glu-Gln-Lys-Leu-Ile-Ser-Glu-Glu-Asp-Leu (SEQ ID NO: 1), the reagent may bind better if the n-terminal residue is a Gly than if it is a Ser.

While generating affinity reagents that are not specific to any single protein may be generally undesirable, there are particular use cases in which it may be optimal to have affinity reagents that are specific to one or more peptides that may occur in many proteins.

The term 'epitope,' as used herein, may refer to a part of a macromolecule, such as a protein or peptide, which is recognized by an affinity reagent. In some cases, an epitope may be a part of a protein or peptide which is recognized by an antibody. In some cases, an epitope may be a part of a protein or peptide which is recognized by an antibody fragment. In some cases, an epitope may be a part of a protein or peptide which is recognized by an aptamer. In some cases, an epitope may be a part of a protein or peptide which is recognized by peptide.

The term 'antigenicity,' as used herein, may refer to capacity of a chemical structure (either an antigen, a hapten, an epitope or a amino acid sequence) to bind specifically with a group of certain products that have adaptive immunity, or to a class of affinity reagents. The term 'antigenicity' may be used interchangeably with the term 'aptagenicity'— the capacity of a chemical structure to be recognized by aptamers. The term 'antigenicity' may also be used interchangeably with the term 'affinity reagent-genicity' which refers to the capacity of a chemical structure to be recognized by affinity reagents generally.

Selection of Affinity Reagents

Novel affinity reagents may be generated by any method known in the art. Methods of developing affinity reagents include Systematic evolution of ligands by exponential enrichment (SELEX), phage display, yeast display, mammalian cell display, insect cell display, ribosome display, particle display, peptimer evolution, peptimer design, and inoculation. In some examples, affinity reagents may be designed using structure based drug design methods. Structure-based drug design (or direct drug design) utilizes knowledge of the three dimensional structure of the epitope of interest and the binding site of the affinity reagent.

In some cases, affinity reagents of this disclosure may be chosen for an ability to bind a desired epitope regardless of the sequence context. In some embodiments, affinity reagents may be designed to bind a desired epitope when a protein is in a denatured context. In some embodiments, the affinity reagents of this disclosure may be chosen for an ability to bind a desired epitope in a protein within a folded or unfolded context. In some embodiments, proteins that have been denatured may contain or generate microfolding within the proteins. In some embodiments, an affinity reagent chosen to recognize the desired epitope AAA may bind equally well, or nearly equally well, to all peptides containing the sequence AAA. In some cases, affinity reagents of this disclosure may be a desired epitope with different affinities according to the sequence context of the epitope. In some cases, affinity reagents of this disclosure may bind several different epitopes regardless of sequence context. In some cases, affinity reagents of this disclosure may bind several different epitopes with different affinities depending on sequence context. Identification of such affinity reagents may be achieved through a three step screening process: 1) an initial screen for binding to a target which comprises the epitope, 2) peptide level qualification screening to characterize the binding of the affinity reagent, and 3) protein level screening to confirm the binding characterization seen in step 2. In some cases, step 3 may be performed before, or partially before, step 2. In some cases, step 2 may be omitted and step 3 may be sufficient to characterize the binding of the affinity reagent.

In some cases, the desired epitope may be a peptide. In some cases, several different epitopes may be desired, in this case an affinity reagent may be selected which binds the desired epitopes. In some cases, the desired epitope or epitopes may be referred to as X. In some cases, the epitope is a non-contiguous epitope. For example an epitope may comprise every second amino acid residue. In another example, an epitope may comprise several amino acid residues that are located proximal to each other in a protein secondary or tertiary structure even though the residues are not proximal in the protein sequence. In some cases, the epitope is a contiguous epitope. In some embodiments, the desired epitope, X, is a short amino acid sequence, of 2, 3, 4, 5, 6 or 7 amino acids. In some cases, X comprises several different short amino acid sequences. In some embodiments, the desired epitope, X, is a three amino acid sequence, $X_1 X_2 X_3$. Affinity reagents which bind this desired epitope in a variety of sequence contexts may be identified by screening for affinity reagents which bind a target comprising the desired epitope.

The target may comprise peptides which include the desired sequence, X. In some cases, the target is a pool of peptides all of sequence X. In some embodiments the target may comprise a pool of peptides of sequence $\alpha X \beta$, wherein X is the desired epitope and $\alpha$ and $\beta$ may be any sequence of zero, one, or more than one amino acids. For example, if the desired epitope, X, is AAA, then examples of the sequences which may be found in the target peptides may include: AAAAA (SEQ ID NO: 2), AAAAC (SEQ ID NO: 3), CAAAA (SEQ ID NO: 4), CAAAC (SEQ ID NO: 5), and CAAAD (SEQ ID NO: 6). In some cases, $\alpha$ and $\beta$ may each be any single amino acid. In some cases, at least one of $\alpha$ and $\beta$ may be 2, 3, 4, 5, 6, 7, 8, 9, 10, or more than 10 amino acids. In some cases, at least one of $\alpha$ and $\beta$ may comprise a linker or spacer. The linkers or spacers may be any linkers or spacers known in the art. In some cases, the linker is an amino acid linker. In some cases, the linker is a polyethylene glycol (PEG) or a PEG polymer chain. The PEG chain may consist of 2, 3, 4, 5, 6, 7, 8, 9, 10, 12, 14, 16, 18, 20, 22, 24, 26, 28, 30, 34, 36, 38, 40, 42, 44, 46, 48, 50 or more than 50 PEG moieties. In some cases, the linker may be a carbon chain. The peptides may also comprise an N terminal or C terminal modification, for example capping. In some cases, the peptides may be modified to remove a charge, for example, terminal amidation (C-terminus) or acetylation (N-terminus). In some cases, the $\alpha X \beta$ peptide may contain nonnaturally occurring amino acids. In some cases, the $\alpha X \beta$ peptide may be modified with a linker and a functional group. For example, the molecule may be of the structure F-L-$\alpha X \beta$, where F is a functional group and L is a linker. In other cases, the molecule may be of the structure $\alpha X \beta$-L-F, where F is a functional group and L is a linker. In some cases, $\alpha$ and $\beta$ may each be glycine, or may each be one or more glycine residues. In some embodiments, residues may be modified to alter their aptagenicity. For example, residues may be altered by adding a positive charge; adding a negative charge; adding a hydrophobic group; modified so as to add a sugar; or other modifications so as to increase chemical diversity.

Peptides may be synthesized using any method known in the art. Several commercial platforms exist for peptide synthesis, such as the MultiPep RSi synthesizer (Intavis, Germany). Peptides may be synthesized using liquid phase or solid phase methods. Synthesized peptides may be verified using any known method for peptide analysis. For example, peptides may be verified using Mass spectrometry, Matrix Assisted Laser Desorption/Ionization Time of Flight Mass spectrometry (MALDI-TOF), Matrix Assisted Laser Desorption/Ionization, AMS (Accelerator Mass Spectrometry), Gas Chromatography-MS, Liquid Chromatography-MS, Inductively Coupled Plasma-Mass spectrometry (ICP-MS), Isotope Ratio Mass Spectrometry (IRMS), Ion Mobility Spectrometry-MS, Tandem MS, Thermal Ionization-Mass Spectrometry (TIMS), or Spark Source Mass Spectrometry (SSMS). Concentration of the synthesized peptides may also be assessed by spectroscopy. An example of a peptide synthesis reaction and verification is provided in Example 8.

FIG. 1 illustrates an immobilized target for selection of affinity reagents, along with an exemplary list of peptides which comprise the target, in accordance with some embodiments. In the example of FIG. 1 the desired epitope is AAA, and the peptides of the target comprise sequences $\alpha$AAA$\beta$, wherein $\alpha$ and $\beta$ are each a single amino acid. In this example the target comprises 400 different peptides, representing each possible sequence of $\alpha$AAA$\beta$, wherein $\alpha$ and $\beta$ are each a single amino acid.

In this way, for any given 3-mer epitope a target comprising a pool of 5-mers may contain 400 different sequences (20 possibilities for $\alpha$ and 20 possibilities for $\beta$, where each of $\alpha$ and $\beta$ are a single amino acid). In some cases, the target may comprise a pool of peptides longer than 5 amino acids in which each or both of $\alpha$ and $\beta$ may comprise two or more amino acids. In some cases, one of $\alpha$ and $\beta$ may comprise zero amino acids, and the other of $\alpha$ or $\beta$ may comprise one or more amino acids. In some cases, the target may comprise a peptide of sequence X without additional amino acids.

In some cases, the target sequence X may be embedded in a longer sequence. For example the target sequence X may be embedded in a 15-mer. The target sequence X may be embedded at any position within the 15-mer, for example in the case of a three amino acid target sequence X, the target sequence X may begin at position 1, 2, 3, 4, 5, 6, 7, 8, 9, 10, 11, 12, or 13 of the 15-mer. Peptides comprising embedded target sequences may be synthesized in solution, or may be synthesized on a chip, such as for example a PEPperPRINT chip or other peptide array. In some embodiments, peptides comprising embedded target sequences may be bound or synthesized onto a single molecule protein array. The longer sequence may be selected to form a secondary structure, or to lack secondary structure. Examples of such secondary structures include alpha helices, beta sheets, proline bends, turns, loops, and cysteine bridges. In some cases, the longer sequence may comprise non-naturally occurring amino acids, or other groups.

An initial selection step may comprise screening a library of affinity reagents against a target which comprises a desired epitope. The affinity reagent library may comprise DNA, RNA, or peptide aptamers with random sequences, or with sequences similar to those of known protein binding aptamers. In some cases, an aptamer library may be a commercial library. In some cases, an aptamer library may be available from an institute, university, academic center, or research center. In some cases, a library may comprise a bead library. In some cases, an aptamer library may be generated from a library of known sequences, or from random sequences. In some cases, an aptamer library may comprise aptamers with particular structures, such as, for example, a stem loop library. In some cases, the aptamer library may comprise switchable aptamers—aptamers which can be switched between two conformations. For example, an aptamer may require a metal ion cofactor to form a first conformation, adding a chelating agent such as EDTA, or EGTA, sequesters the metal ions and causes the aptamer to adapt a different conformation. Other factors that may be used to induce aptamer switching include light, pH, temperature, magnetic fields, and electrical current.

The screening of an aptamer library against the target may be performed by any method known in the art. In one aspect, the target may be immobilized on a solid support and the aptamers may be added under conditions that allow binding of aptamers with low specificity. Unbound aptamers may be washed from the target with a series of washes of increasing stringency. Aptamers that remain bound to the target through the wash steps may be sequenced and amplified for further rounds of selection, or used for the design of additional aptamers with high sequence similarity. Several rounds of target binding, washing, sequencing and amplification, or design of new aptamers, may be repeated until aptamers of desired specificity and binding affinity are generated. An aptamer library may also be screened using a bead based approach utilizing beads which each comprise multiple copies of an aptamer. An aptamer library may also be screened using an array-based approach, for example by spotting multiple copies of each aptamer of the library onto an array and then assessing the spots to which the target binds. An aptamer library may also be screened using a particle display approach. In some embodiments, an aptamer library may be screened using a single molecule protein array.

In some cases, the percentage of the target pool to which an identified affinity reagent binds may be measured, for example by comparing the number of bound copies of the affinity reagent with the number of target peptides available for binding. In some embodiments, an affinity reagent may bind to 10%, 20%, 30%, 40%, 50%, 60%, 70%, 80% or more than 80% of the peptides comprising the target. Additionally, once a particular affinity reagent is identified and selected, the affinity reagent may be validated. In some embodiments, a selected affinity reagent may be validated against a plurality of sequences containing epitopes to which the affinity reagent is characterized as binding to. In some embodiments, a selected affinity reagent may be validated by assessing the selected affinity reagent against a plurality of protein sequences on a single molecule protein array.

Figure 2:
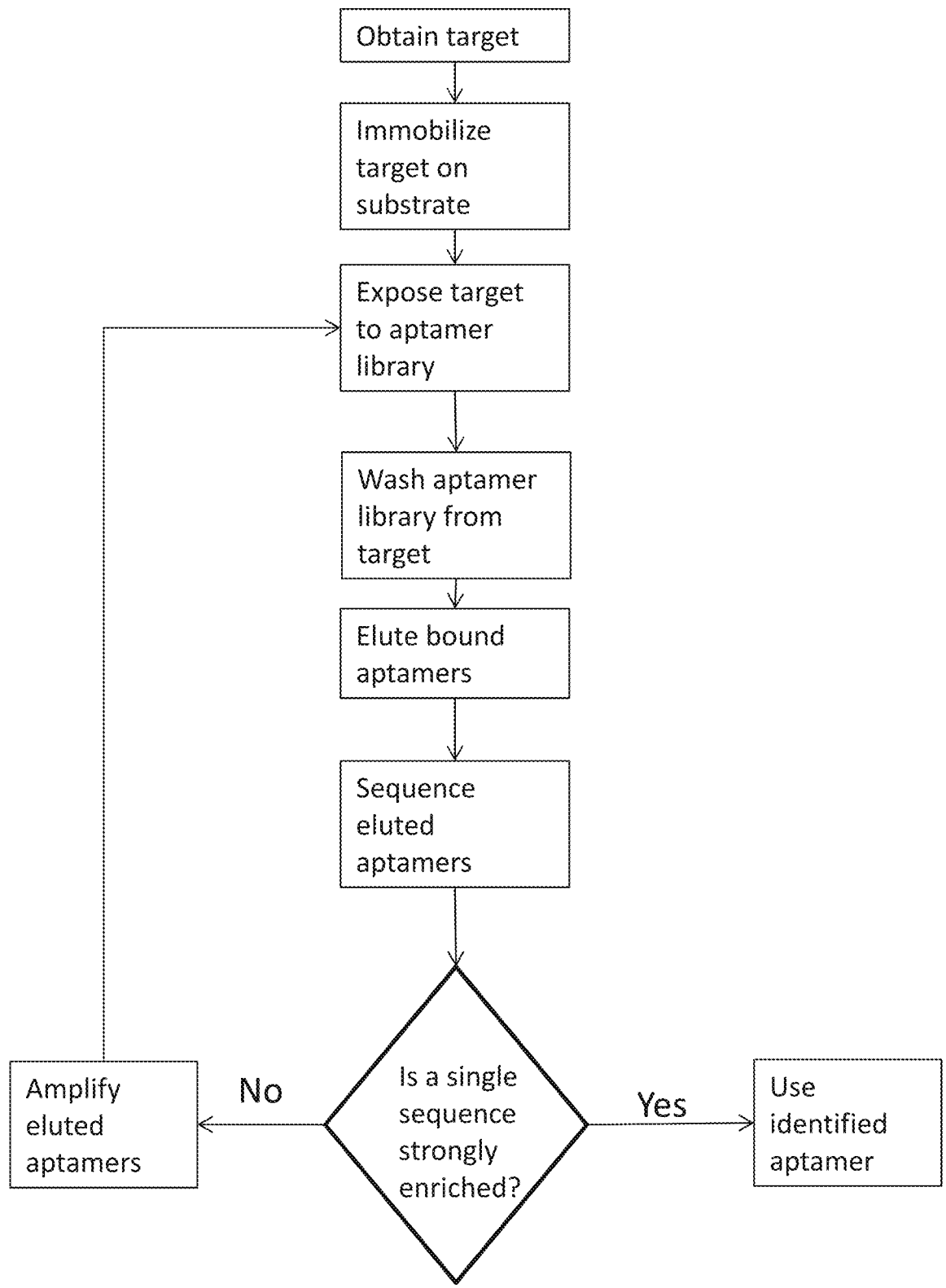
FIG. 2 illustrates a flowchart of a process of affinity reagent selection, in accordance with some embodiments.

FIG. 2 illustrates a flowchart of a process of affinity reagent selection, in accordance with some embodiments. First, a target is obtained and immobilized on a solid support. The target is then exposed to a library of affinity reagents. In this example, the affinity reagents are aptamers. Unbound aptamers was washed from the target, and the remaining aptamers are eluted. The eluted aptamers may be sequenced in a manner which preserves the aptamers, or an aliquot of the eluted aptamers may be sequenced. Based on the sequencing results a decision is made whether a single aptamer, or small group of aptamers, is highly enriched, indicating strong binding, and should be selected for further screening, or whether many different aptamers show mild enrichment in which case the eluted aptamers may be amplified and reapplied to the target. These steps may be repeated until an aptamer with desired binding affinity is produced. The stringency of the wash step may be increased in subsequent wash steps. The length of the wash step may be selected to obtain affinity reagents with low off rates.

In other aspects, the initial selection step may comprise immobilizing aptamers of the library onto a solid support and adding labeled targets. The solid support may be a slide, a bead, a magnetic bead, a surface within a flowcell. Aptamers of the library may be immobilized as single copies, or may be immobilized in a pool. For example, multiple copies of single aptamer may be immobilized on a region of a solid support, while multiple copies of other aptamers are immobilized on other regions of said solid support. In some cases, aptamers of a library may be modified with adapters and hybridized to an oligo coated solid support. Cluster amplification may then be used to locally amplify each aptamer on the solid support. In some cases, a solid support is a glass slide. In some cases, a solid support is a flow cell. In some cases, a solid support is a flow cell suitable for fluorescent imaging. In some cases, a solid support is a magnetic bead, or a plurality of magnetic beads. Each magnetic bead of a plurality of magnetic beads may be coated in multiple copies of a single, distinct, aptamer, such that each bead is coated with a different aptamer from each other bead.

In other aspects the initial selection step may comprise injecting a target into a host animal capable of producing antibodies against the target. The host animal may be any animal capable of producing antibodies, for example a rabbit, a goat, a mouse, a rat, a horse, a cow, a sheep, a camel or a donkey. Antibodies may be recovered from the serum of the host animal. Serum from the host animal may be used as is, or the antibodies may be purified from the serum. Methods of purifying antibodies include physicochemical fractionation, class-specific affinity or antigen-specific affinity. Class-specific affinity may involve binding of the antibodies to immobilized biological ligands with specific affinity to immunoglobins. Antigen-specific affinity may involve use of immobilized target to pull down antibodies which bind the target. The purified antibodies may be sequenced to identify the antibodies from the serum, identified antibodies may then be synthesized in vivo or in vitro.

In some cases, rather than extract antibodies from the serum of the immunized host animal the spleen may be extracted and spleen cells may be immortalized. One method to immortalize the spleen cells may be to fuse the cells with myeloma cells to form hybridomas. Individual clones may be isolated from the hybridoma, each of which will produce a single monoclonal antibody. The different monoclonal antibodies may be screened against the target using similar methods as above. Briefly, the target may be immobilized on a solid support and the antibodies may be added under increasingly stringent conditions to determine the antibodies which bind with desired affinity. The sequence of a selected monoclonal antibody may be derived by sequencing the protein, or by sequencing the coding sequence from the cell line which produced it.

In some cases, an antibody may be selected using phage display. A phage library may be obtained in which each phage expresses an antibody on its surface and encodes the sequence for generating that antibody. The phage library may be applied to the peptide target and phages which express, and encode, antibodies that do not bind to the target may be washed away. Phages which express, and encode, antibodies that bind the target may be eluted from the target. The eluted phages may be amplified by infecting cells with the phages, and the amplified phages may be used to repeat the selection step for a desired number of iterations. Succeeding iterations may utilize wash buffers with increasing stringency or increasing wash times. Once the desired number of iterations has been completed the selected phages may be analyzed, for example by lysing the phage to sequence the DNA encoding the expressed antibody. This sequence may be used to construct a cell line which will express the selected antibody.

In some cases, an antibody, or other affinity reagent, may be selected using bacterial, mammalian cell, insect cell or yeast display. These methods are similar to phage display described above, but a bacterial, mammalian cell, insect cell or yeast library is obtained in which each bacterium, mammalian cell, insect cell or yeast cell expresses an antibody on its surface and encodes the sequence for generating that antibody. The selection method is the same as that described for phage display.

In some embodiments, affinity reagents may be selected against many different targets in parallel. For example, many different targets may be fixed to different locations on an array, and used with a SELEX selection method. In another example, many different targets may be attached to magnetic beads and used with a SELEX selection method. In some embodiments, affinity reagents may be selected against targets on a single molecule protein array.

In an embodiment, an Illumina style next generation sequencing platform may be adapted for aptamer selection. An aptamer library may be labeled on each end with an adapter and hybridized to oligonucleotides in a flow cell. Solid state amplification is used to create an aptamer cluster from each starting aptamer of the aptamer library. The surface of the flow cell may now be covered in a plurality of nucleic acid clusters, each one comprising many copies of a single aptamer from the aptamer library. A sequencing reaction may be run on the flow cell, using nucleic acid polymerases, primers and four different fluorescently labeled reversible terminators (A, T, C, and G). This may provide the sequence of the aptamer at each location in the flow cell. Once identity of each aptamer cluster is known one or more detectably labeled peptide targets may be added to the flow cell and incubated with the aptamer clusters. After a period of incubation unbound targets are washed off and the flow cell is imaged to determine the locations where targets are bound. As multiple phases of wash steps are performed, $K_D$ values may be generated. In particular, after an initial wash step to remove unbound targets, an initial image may be taken to identify which bound targets are still present. After the initial image is taken, a second wash step may be performed to remove targets that have become unbound during the elapsed time and a second image may then be taken. This process may be iterated over a plurality of stages so as to calculate $K_D$ values across a number of targets based on the times at which they become unbound. In some instances, an initial wash step may be followed immediately by a second wash step. $K_D$ affinity determinations may be performed using techniques including, for example, surface plasmon resonance or biolayer interferometry (BLI) techniques.

In some cases, many different targets with different, resolvable, labels may be added to the flow cell to perform multiple parallel selections. An example of this method is provided in Example 7.

In some embodiments the ease of affinity reagent selection may be affected by the sequence/structure of the epitope. Epitopes with high 'immunogenicity', 'antigenicity', 'aptamergenicity' or 'affinity reagent-genicity' may be easier to design affinity reagents against. For example, epitopes containing amino acid residues with very different chemical properties may be easier to select affinity reagents for. Epitopes such as GGG or AAA may be harder to select affinity reagents against than epitopes such as KWK or DCY. In some embodiments, epitopes may be modified, such as using chemical bioconjugation, so as to identify affinity reagents to interact with the modified epitopes. Amino acids KRDEYWC (SEQ ID NO: 7), in particular are readily modified. In some embodiments, when identifying an affinity reagent to bind to a desired epitope of, it may be beneficial to modify DYW with a chemical reaction that adds a component that is easier to identify using an affinity reagent. In particular, DYW may be modified to add a positive charge or nucleic acid which may then have an affinity reagent tailored to that component. In this way, the DYW epitope may be easier to stand out. Further, when running a platform to identify a desired epitope that has been modified, a protein sample (such as a blood sample) may be exposed to a chemical reaction that will modify a DYW epitope in an expected and particular way, which may then allow the protein to be assessed against a particular affinity reagent to determine whether the unmodified DYW epitope corresponding to the modified DYW epitope having a positive charge or nucleic acid component was present in the original protein sample. In some embodiments, the chemical reaction to the DYW epitope may be reversible. In some embodiments, the chemical reaction to the DYW epitope may be irreversible. In this way, tailored assays may be run to identify the modified DYW epitope.

In some cases, a collection of potential targets may be stratified into different groups based on the predicted 'antigenicity' or 'affinity reagent-genicity' of the target epitopes. For example, in some cases combining both high antigenicity targets and low antigenicity targets into a single parallel selection step may result in the affinity reagents against the high antigenicity targets swamping out signals from affinity reagents against the low antigenicity targets. Predicted antigenicity may be based on the chemical properties of the amino acid residues in the targets, with charged, and larger, amino acids being expected to have higher antigenicity. Targets which contain two or more same or chemically similar amino acid residues may have lower antigenicity than targets which contain amino acid residues with very different chemical properties. In some cases, the antigenicity of different targets may be determined experimentally, based on the results of initially affinity reagent selection screens.

Characterization Screening of Affinity Reagents

A peptide characterization or qualification screen may be performed on any affinity reagent identified as binding the target. The affinity reagent may have been identified in a screen as described above, or may have been obtained through any method known in the art. In some embodiments, a secondary characterization screen may be used to determine the specificity of the affinity reagent to a desired epitope over other possible sequences. For the secondary screen, a library of possible n-mer sequences may be used to determine if the affinity reagent recognizes other sequences. In some cases, the library comprises at least 80%, 85%, 90%, 95%, 96%, 97%, 98%, 99%, 99.9%, or more than 99.9% of all possible n-mer sequences. In some cases, the library comprises all possible n-mer sequences. If the affinity reagent is believed to bind a 3-mer, then the other sequences may be selected to represent all possible 3-mers ($20^3$=8000). In some embodiments, the sequences that are selected to represent the possible epitopes of interest may be embedded within other sequences, such as flanking sequences. In some embodiments, the sequences that are selected to represent the desired epitopes may have a flanking sequence, or a chemical linker, added to the side of the desired epitope that attaches to a solid substrate so that the desired epitope is in a position far enough from the solid substrate so as to allow the affinity reagent to access the desired epitope. If the affinity reagent is believed to bind a 4-mer then the other sequences may be selected to represent all possible 4-mers ($20^4$=160,000). In one embodiment the pool of different n-mers may be immobilized in different wells of a multiwall plate, or on different regions of a solid support. The affinity reagent may then be incubated with the library and unbound affinity reagent is gently washed off. Regions where the affinity reagent has bound to the library may be detected by any method suitable for visualizing the affinity reagent. In some examples, the affinity reagent may be visualized by a dye or reagent which binds to proteins and/or nucleic acids, or the affinity reagents may be labeled with a detectable moiety prior to addition to the library. In some cases, binding of the affinity reagent to the target may be detected by Fluorescence Resonance Energy Transfer (FRET) Microscopy, Surface Plasmon Resonance (SPR), Bioluminescence Resonance Energy Transfer (BRET), NanoBRET, Bio-layer Interferometry (BLI), or Octet.

In some cases, presence or absence of the affinity reagent may be determined under several different conditions—for example different stringencies of washing, which may be achieved, for example, by using different washing buffers, different times of washing, different washing temperatures, or different levels of agitation. In some cases, the binding of the affinity reagent may be measured repeatedly over time to generate a time course of binding. In some cases, determining the binding of the affinity reagent under different conditions and/or at different times may enable estimation of the $K_D$, $K_{ON}$ or $K_{OFF}$ of the affinity reagent for the target.

In some embodiments, different washing and detecting conditions may be used to identify affinity reagents with desired properties, such as, for example desired on rates and off rates, or association constants ($K_{ON}$) and disassociation constants ($K_{OFF}$). In some cases, desired affinity reagents may have slow off rates. Equilibrium of an affinity reagent epitope binding reaction is reached when:

$$[\text{affinity reagent}]\cdot[\text{epitope}]\cdot K_{ON}=[\text{affinity reagent-epitope}]\cdot K_{OFF}.$$

In some cases, preferred affinity reagents may have a $K_{OFF}$ value that is less than about 1 $s^{-1}$, $10^{-1}$ $s^{-1}$, $10^{-2}$ $s^{-1}$, $10^{-3}$ $s^{-1}$, $10^{-4}$ $s^{-1}$, $10^{-5}$ $s^{-1}$, $10^{-6}$ $s^{-1}$, $10^{-7}$ $s^{-1}$, $10^{-8}$ $s^{-1}$, $10^{-9}$ $s^{-1}$, or $10^{-10}$ $s^{-1}$. In some cases, the off rate may be more critical than the on rate as a poor on rate may be compensated for by increasing the amount of affinity reagent added to a reaction, or by increasing the incubation time before washing. In some cases, the affinity reagents are selected such that the off rate is sufficient to enable the affinity reagent to remain bound through one or more washing steps, and until after an imaging step has been completed. In some cases, an affinity reagent may remain bound to an epitope for at least about 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 25 min, 30 min, 35 min, 40 min, 45 min, 50 min, 55 min, 60 min, or more than about 60 min.

In some cases, a preferred affinity reagent only binds to one of the 3-mers in the library. In other cases, a preferred affinity reagent may bind to 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100 or more than 100 different 3-mers. In some embodiments, the step of washing off the affinity reagents may be repeated with increasing stringencies and the affinity reagents which remain bound may be detected after each washing step.

In another method, the affinity reagents may be immobilized on a solid support and the pool of all possible n-mers may be added to the affinity reagents, unbound n-mers may be removed by washing and the remaining n-mers may be analyzed to find the sequences bound by the affinity reagents. Repeated screening steps may be performed with washing steps of differing stringency. The bound n-mers may be identified using any suitable method, for example mass spectrometry or high performance liquid chromatography mass spectrometry. In some cases, a pool of random n-mers may be used rather than the pool of all possible n-mers. In cases where a pool of random n-mers was used for the characterization screen, both the bound and unbound n-mers may be identified. Sequences which were not represented in either the bound or unbound n-mer pools may be noted for follow up in subsequent characterization screens. In some cases, the pool of random n-mers may be characterized before applying to the affinity reagent to ensure that the pool includes at least 70%, 75%, 80%, 85%, 90%, 95%, 96%, 97%, 98%, 99% or more than 99% of possible n-mer sequences. In some cases, a preliminary characterization screen may be performed with random n-mers and affinity reagents which bind less than about 30, 25, 20, 15, 10 or 5 n-mers may be selected for further characterization using a pool of all possible n-mers.

A further peptide qualification screen may be performed to determine whether the affinity reagent binds specifically to the desired epitope or whether the affinity reagent is binding to a subpart of the epitope. For example, an affinity reagent believed to be specific for the 3-mer sequence AKD may actually be specific for the dimer sequence AK. Thus for each n-mer affinity reagent a screening step may be performed against the set of all (n−1)-mers. In some cases, where a characterization screen has been performed and the set of all n-mers bound by the affinity reagent is known, the screen may be limited to merely the (n−1)-mers which are contained within the n-mers which are bound by the affinity reagent. For example, if the only 4-mer bound by the affinity reagent is AAKD (SEQ ID NO: 8) then a screen may be performed against AAK and AKD, rather than all possible 3-mers. If an affinity reagent does bind to a (n−1)-mer then an additional screen against (n−2)-mers may be performed to further define the specificity of the affinity reagent. In some cases, affinity reagents which bind to (n−1)-mers may not be selected for further screening. In other cases an affinity reagent which binds to no more than one of the (n−1)-mers may be selected. In other cases, affinity reagents which bind to more than one (n−1)-mers may be retained for further screening.

An additional peptide qualification screen may be performed to determine the effect of flanking sequences on the affinity reagent's affinity for its epitope or epitopes. For this step a library of peptides of the sequence $\alpha X\beta$, (wherein X is the affinity reagents epitope, or epitopes, and $\alpha$ and $\beta$ may be any one or more amino acids), may be created. In the example of an affinity reagent which binds to a single epitope, and given a case wherein $\alpha$ and $\beta$ are each a single amino acid, given that the sequence of the bound epitope is set, there are 400 possible $\alpha X\beta$ sequences regardless of the length of the desired epitope. For cases where the affinity reagent binds two or more different epitopes, or where $\alpha$ and $\beta$ may each be none, one, or more than one amino acids, there may be many possible sequences of $\alpha X\beta$. In some cases, the set of $\alpha X\beta$ peptides used in this screening step may be the same set of $\alpha X\beta$ peptides which comprised the target used for the selection of the affinity reagent. The affinity reagent may be screened against the set of $\alpha X\beta$ sequences using standard screening methods. Reviewing the list of $\alpha X\beta$ sequences to which the affinity reagent binds, as well as the relative binding affinities, may allow a determination of the effects of the flanking sequence on the binding affinity of the affinity reagent. If strong effects are seen then a further screen may be performed with longer flanking sequences, for example if a first library of sequences consisted of peptides $\alpha X\beta$ wherein $\alpha$ and $\beta$ where each a single amino acid then a subsequent screen may be performed with a library of peptides consisting of $\gamma X\delta$, wherein $\gamma$ and $\delta$ each comprise two amino acids.

Figure 3A:
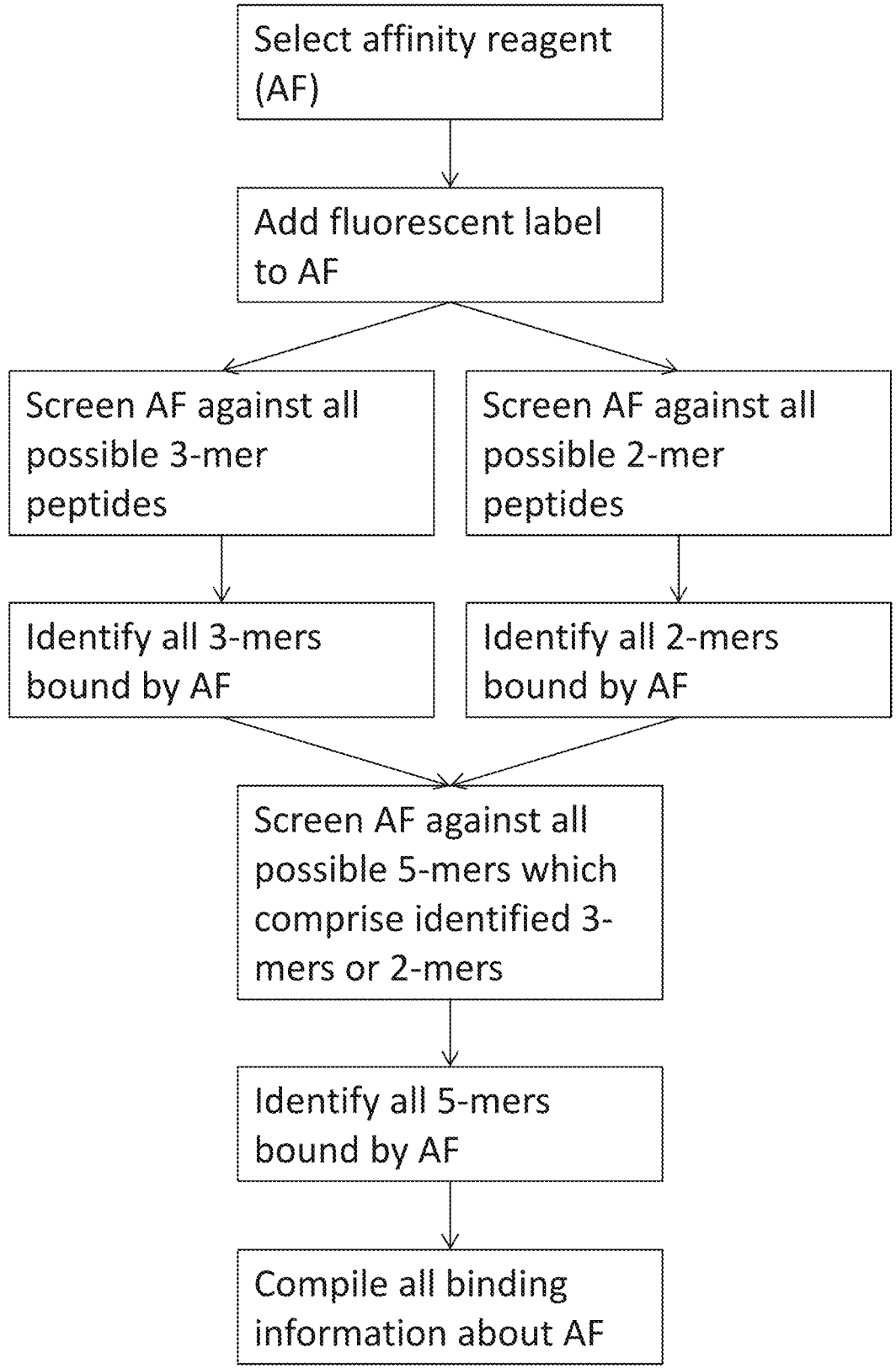
FIG. 3A illustrates an exemplary flowchart of screening steps in the process of affinity reagent characterization, in accordance with some embodiments.
Figure 3B:
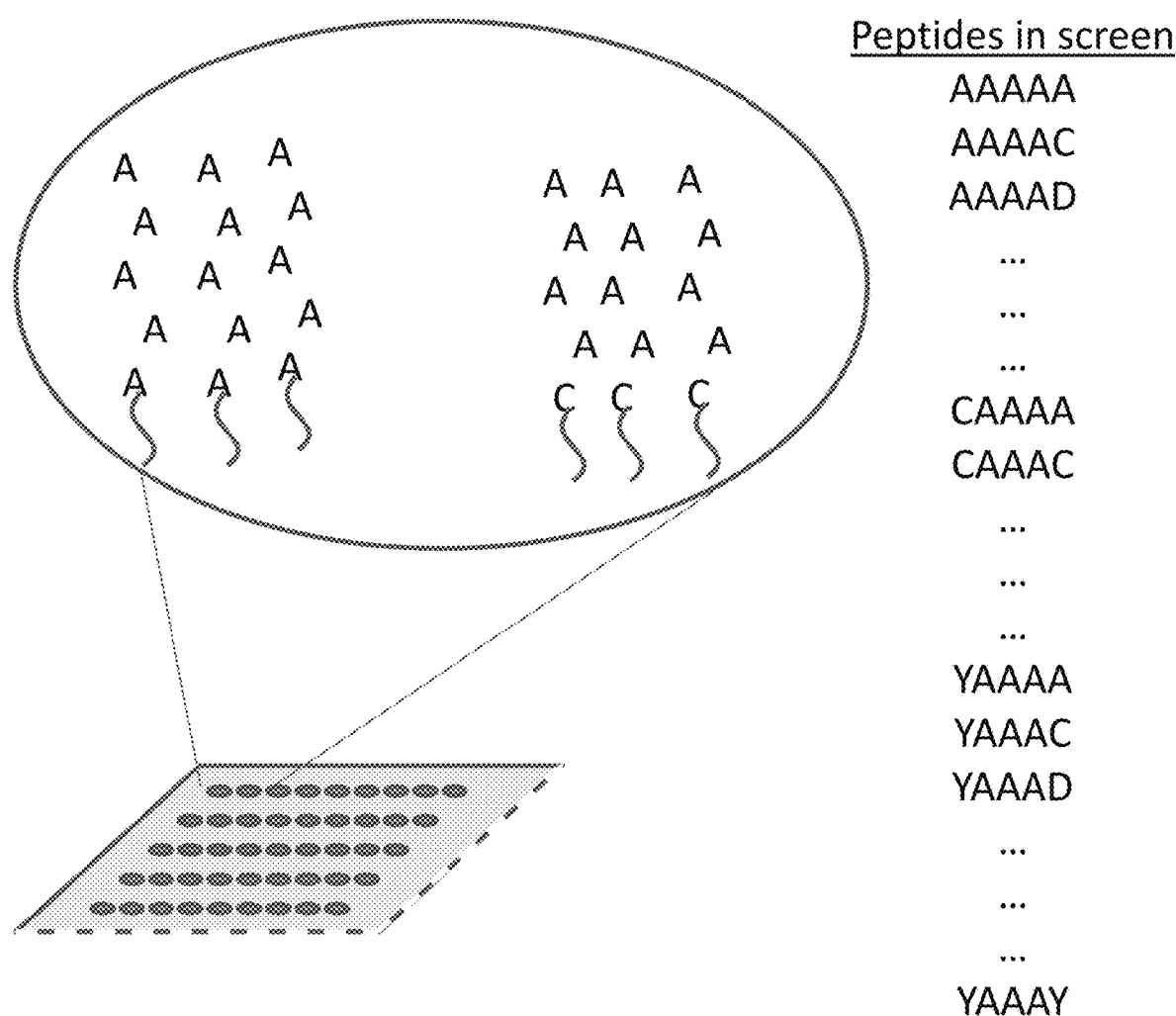
FIG. 3B illustrates an array of 5-mer $\alpha X\beta$ peptides for undertaking a screening step to determine the effect of flanking sequences on the binding of an affinity reagent to the epitope AAA, in accordance with some embodiments.
Figure 4:
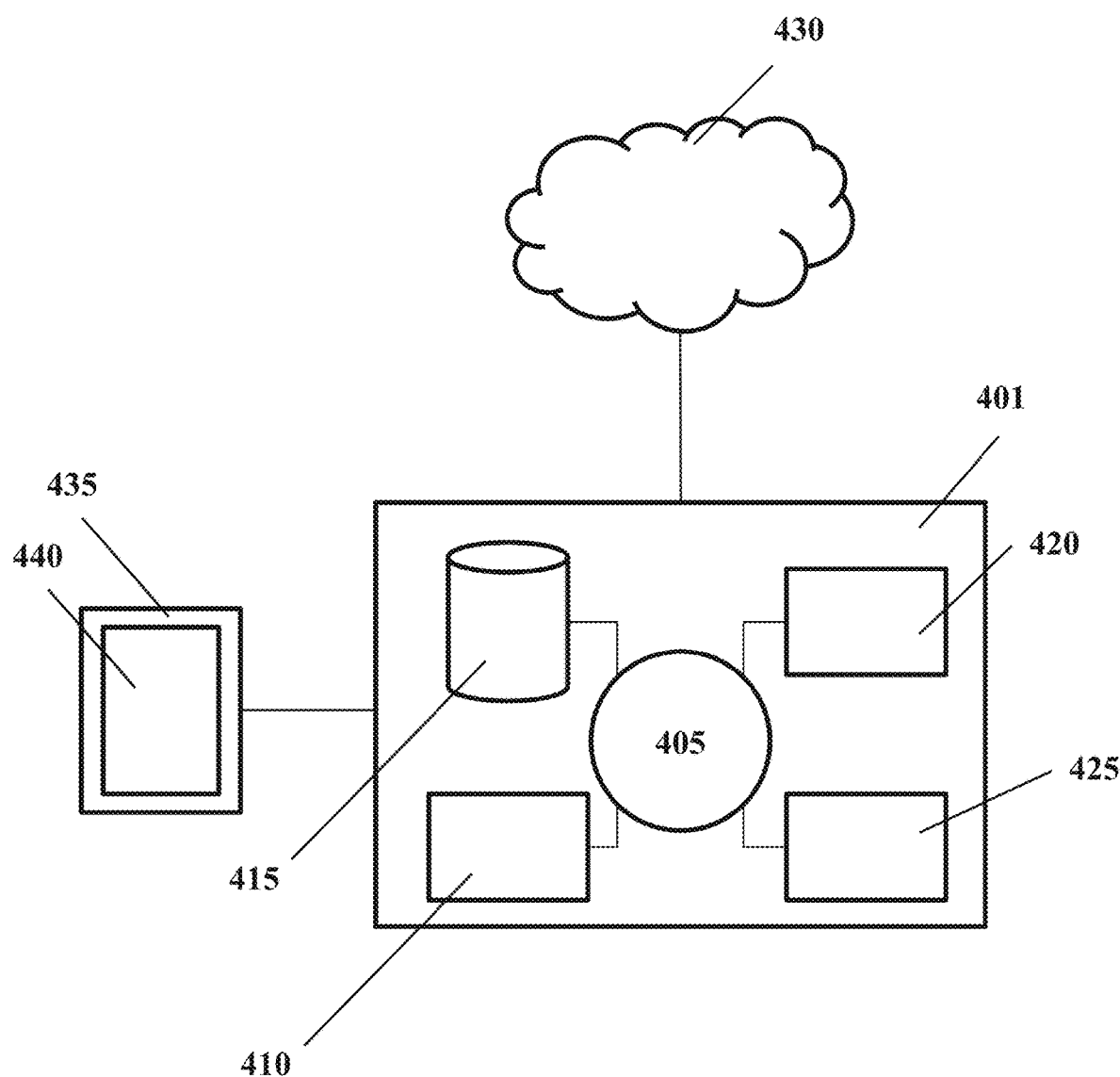
FIG. 4 illustrates a computer control system that is programmed or otherwise configured to implement methods provided herein.
Figure 5A:
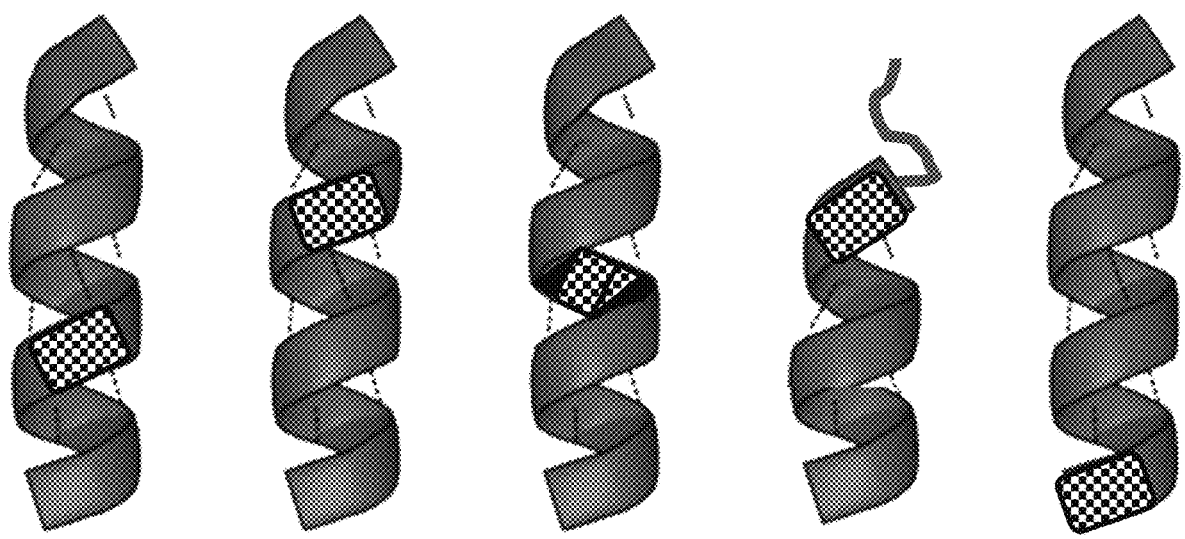
FIGS. 5A and 5B illustrate examples of a target embedded in longer sequences with different secondary structures.
Figure 5B:
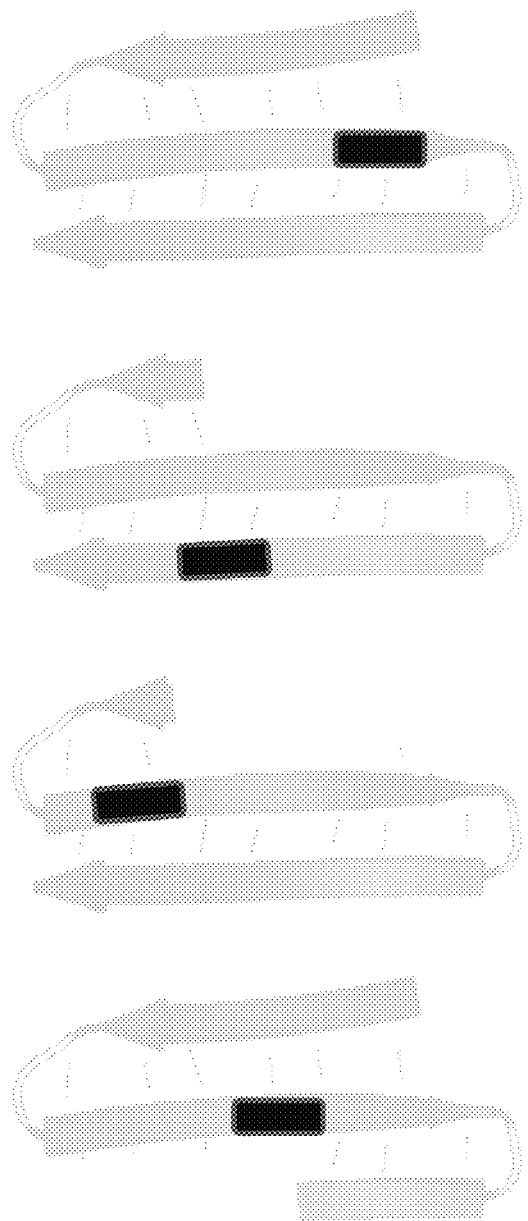

FIG. 3A illustrates an exemplary flowchart of screening steps in the process of affinity reagent characterization, in accordance with some embodiments. An affinity reagent is labeled with a fluorescent label to facilitate detection of the affinity reagent. The affinity reagent is then applied to a pool of peptides comprising all possible 3-mer sequences. The pool of peptides comprising all possible 3-mer sequences may be immobilized as an array on a solid support. In some embodiments, the pool of peptides comprising all possible 3-mer sequences may be immobilized on one or more single molecule protein arrays. In some embodiments, a plurality of 3-mer sequences may be immobilized on a solid substrate. In some embodiments, a plurality of 3-mer sequences may be immobilized on a single molecule protein array. In another step, which may be performed in parallel, the affinity reagent is then applied to a pool of peptides comprising all possible 2-mer sequences. All 3-mer and 2-mer peptides bound by the affinity reagent are identified. A pool of 5-mer peptides is obtained which contains all possible 5-mer peptides which contain the sequences of the identified bound 3-mers and 2-mers. As an example, if the affinity reagent is known to bind only the epitope AAA, then the pool of all possible 5-mer peptides consist of the peptides $\alpha AAA\beta$, as illustrated in FIG. 3B. The affinity reagent is then applied to the pool of 5-mer peptides, and data from all three screening steps is compiled to provide a binding characterization of the affinity reagent. In other examples steps may be omitted or performed in different a different order. A protein qualification screen may be performed to confirm that the affinity reagent binds to the desired epitope, or epitopes, in the context of a protein rather than a peptide. Proteins of known identity and sequence may be immobilized on a solid support and exposed to the affinity reagent. The proteins may be applied to the solid support from purified protein stocks, or may be synthesized on the solid support through a process such as Nucleic Acid-Programmable Protein Array (NAPPA). In some cases, the proteins used for this screen may consist of proteins which include the predicted or known epitope or epitopes of the affinity reagent. In some cases, the proteins used for this screen may consist of proteins which do not include the predicted or known epitope or epitopes of the affinity reagent. In some cases, the proteins used for this screen may consist of both proteins which include the predicted or known epitope or epitopes of the affinity reagent, and proteins which do not include these epitopes. Binding of the affinity reagent to different proteins may be assessed by any method known in the art. For example, bound affinity reagents may be identified by affinity reagent specific antibodies, by dyes which bind to protein or nucleic acid, or by labeling the affinity reagents with a detectable moiety prior to screening. Once the bound and unbound proteins have been determined the sequences may be compared to determine how often the affinity reagent binds to its epitope, or epitopes, and whether the binding is affected by the surrounding protein sequence. The binding results and protein sequences may also be fed into a machine learning algorithm to verify the most likely binding sites. Off-target affects may also be determined by this method. In some cases, an affinity reagent against an epitope may be selected if it binds to at least about 1%, 2%, 3%, 5%, 7%, 10%, 15%, 20%, 30%, 40%, 50%, 60%, 70%, 80%, 90%, 95%, or more than 95% of the proteins which contain the epitope. In some cases, an affinity reagent against an epitope may be selected if it binds to less than about 50%, 40%, 30%, 20%, 10%, 5%, or less than 5% of the proteins which do not contain the epitope. In some cases, multiple affinity reagents may be selected against the same epitope. Said multiple affinity reagents may be pooled together and used as a pooled affinity reagent.

Characterization of Affinity Reagents Using Binding Data from Interactions with Known Proteins It is useful to find ways of characterizing binding affinities of particular affinity reagents across the proteins comprising a proteome (e.g. human proteome, yeast proteome, E. coli proteome). Even when looking at the ~70,000 canonical protein sequences defined within the reference proteome database on Uniprot (https://www.uniprot.org/proteomes/UP000005640), it would take a great amount of effort to characterize the binding affinity of a set of particular affinity reagents across the entire set of proteins in the human proteome. Further, when proteoforms are considered, the number of distinct proteoforms within the human proteome that may be identified may number in the hundreds of thousands or millions. As such, it is beneficial to efficiently characterize binding affinities of affinity reagents in a way that is able to be applied across a number of unknown proteins. In some embodiments, binding affinities of affinity reagents are generated by assessing interactions of affinity reagents with known proteins. In some embodiments, binding affinities of affinity reagents are generated by assessing interaction of affinity reagents with proteins with sequences derived from sequence databases such as reference proteomes from NCBI or Uniprot. In some embodiments, protein sequences used in methods provided herein may have no known natural origin, such as proteins having random sequences. In some embodiments, printing proteins having non-natural sequences may be useful in providing additional input into models such as those discussed herein. In some embodiments, binding affinities of affinity reagents to particular targets within known proteins may be assessed based on the presence of that target within the known protein and based on the number of copies of the target within the known protein.

Accordingly, in some cases, affinity reagents, such as affinity reagents disclosed herein, may be characterized by screening the affinity reagents against an array of known proteins. Binding data that is generated from the screening of the affinity reagents against the known proteins may be used to generate binding affinity information that may be used to assess whether an epitope, or multiple epitopes, that the affinity reagent binds is present within an unknown protein. In particular, each affinity reagent may bind to one or more epitopes. Further, each protein may contain multiple epitopes that may each bind to a particular affinity reagent. For proteins that contain multiple epitopes that bind to a particular affinity reagent, the protein may have multiple copies of a particular epitope and/or may have multiple copies of distinct epitopes. As such, in some cases a particular protein may bind to multiple affinity reagent molecules, with each of the multiple affinity reagent molecules potentially attaching to one of a plurality of epitopes present within a protein. Accordingly, information that helps to characterize affinity reagents and predict binding to proteins may be applicable to methods of identifying unknown proteins. In some embodiments, the binding data that is generated may be used to identify unknown proteins for which a sequence is represented within a protein database. In some embodiments, the binding data may be used to generate a particular profile that may be used to characterize an unknown protein until a sequences that is associated with the unknown protein is identified. In particular, binding data generated from interactions of affinity reagents with proteins in the array of known proteins may be used to determine the binding affinity of an affinity reagent for one or more epitopes within the known proteins. This, in turn, may be used in assessing binding affinity for the screened affinity reagents against proteins having one or more copies of those one or more epitopes. Additionally or alternatively, the binding affinity of an affinity reagent for one or more epitopes may be used in assessing binding affinity for the screened affinity reagents against proteins having other epitopes that are similar to, or the same as, the characterized one or more epitopes. In some embodiments, binding data from interactions of affinity reagents screened against proteins in the array of known proteins may be used to determine affinity characteristics of particular types of epitopes, such as each possible epitope of a particular length, epitopes within a particular subset of the complete protein sequence, epitopes in a particular location of the folded protein structure, each epitope predicted or observed to be highly accessible in the folded protein structure, or each epitope identified from an empirical or in silico binding screen, within one or more proteins within the array of known proteins. In some embodiments, the binding data from interactions of affinity reagents screened against proteins in the array of known proteins may be used to determine binding affinities of affinity reagents with multiple epitopes within one or more proteins within the array of known proteins. In some embodiments, the binding data from interactions of affinity reagents screened against proteins in the array of known proteins may be used to determine a binding affinity of an affinity reagent with a protein that has multiple copies of a particular epitope.

A method for conducting a screen of affinity reagents against an array of known proteins is described below. As described below, the method may provide that tested affinity reagents bind at least one three amino acid epitope (a trimer) or a combination of trimers. However, embodiments of the method may include one or more epitopes of different lengths other than trimers, such as dimers 4-mers, 5-mers, 6-mers, 7-mers, longer epitopes and non-contiguous epitopes. In some embodiments, methods may provide that tested affinity reagents bind at least one dimer or a combination of dimers. In some embodiments, methods may provide that tested affinity reagents bind at least one dimer or trimer or combination of dimers or trimers. In some embodiments, methods may provide that tested affinity reagents bind two or more n-mers selected from the group consisting of dimers, trimers, 4-mers, 5-mers, 6-mers, 7-mers, n-mers longer than 7-mers, and non-contiguous epitopes. In some embodiments, methods may provide that tested affinity reagents bind three or more n-mers selected from the group consisting of dimers, trimers, 4-mers, 5-mers, 6-mers, 7-mers, n-mers longer than 7-mers, and non-contiguous epitopes. In some embodiments, methods may provide that tested affinity reagents bind more than three n-mers selected from the group consisting of dimers, trimers, 4-mers, 5-mers, 6-mers, 7-mers, n-mers longer than 7-mers, and non-contiguous epitopes.

Using methods provided herein, protein inferences may be calculated. In some embodiments, protein inferences may be calculated based on one or more considerations, such as binding measurements of particular affinity reagents to a protein; information related to protein sequences of possible candidate proteins of the protein; and information, such as binding affinity information, from which a prediction having a particular degree of confidence of the expected degree of binding for each affinity reagent to each candidate protein may be derived. Some methods as described herein are provided for generating a statistical model of an affinity reagent from which the probability of the affinity reagent binding to a protein may be computed provided a primary sequence of that protein.

In some embodiments, a statistical model may be trained using a series of binding measurements of a plurality of particular affinity reagent to each of a plurality of known proteins. This approach may be used to predict affinity reagent—protein binding when direct empirical measurements are not available. In the context of applying methods to proteins within a human proteome, a minimal list of candidate human proteins may contain approximately 20,000 proteins. Further, allowing for splicing variants, polymorphisms, partial degradation, and additional non-human genomes may rapidly expand candidate proteins to number in the hundreds of thousands or millions.

Method

In some embodiments, an array of known proteins sequences is obtained. In some embodiments, this array of known proteins may be generated by spotting pure protein samples onto a chip. In some embodiments, this array of known proteins may be generating by translating proteins directly onto a chip, for example by using a nucleic acid programmable protein array (NAPPA). The number of known proteins which may be analyzed, across one or more particular arrays, may contain less than 50 different protein sequences, may contain 50 different protein sequences, may contain more than 50 protein sequences, may contain approximately 100, 150, 200, 250, 300, 350, 400, 500, 600, 700, 800, 900, 1,000, 2,000, 3,000, 5,000, 10,000, 15,000, 20,000, or more than 20,000 protein sequences. As a generalized concept, as more proteins are analyzed, the accuracy of a model being developed may be increased. In some embodiments, the number of known protein which may be analyzed may be between about 300 and about 3000 different protein sequences; between about 500 and about 2000 different protein sequences; between about 600 and about 1500 different protein sequences; between about 600 and about 1000 different protein sequences; or between about 1000 and 3000 different protein sequences, among other examples. In some embodiments, each known protein may be present in multiple copies at a single location on the array. In some embodiments, each protein may present, in multiple copies, in numerous locations across the array. In some embodiments, each protein may be present in two locations, three locations, four locations, five locations, six locations, seven locations, eight locations, more than eight locations, or a combination of different numbers of locations, across the array. In some embodiments, each protein may be present in greater than about 1000 copies, 2000 copies, 3000 copies, 5000 copies, 10,000 copies, 20,000 copies, 50,000 copies, 100,000 copies, 500,000 copies, 1,000,000 copies, 2,000,000 copies, 5,000,000 copies, 10,000,000 copies, 100,000,000 copies, 1 billion copies, 10 billion copies, 100 billion copies, or more than 100 billion copies at each of one, two, three, four, five, six, seven, eight, or more than eight locations, across the array. Further, in some embodiments, affinity reagents may also be characterized by assessing small numbers of proteins at particular locations, such as 1 copy per location, 2 copies per location, 3 copies per location, 4 copies per location 5 copies per location, 10 copies per location, or more than 10 copies per location. In some embodiments, locations may be distinguished from one another when each particular location has resolvably distinct from another location based on optical detection or other detection sensors.

In some embodiments, binding of one or more affinity reagents to known proteins within the array may be assessed by hybridizing a fluorescently-labelled affinity reagent to the array and measuring observed fluorescence at each spot on the array. In some embodiments, the identity of each protein at each spot may be known so that fluorescence (as a proxy for binding) may be mapped to protein identities.

In some embodiments, trimer epitopes may be used in assessing binding of affinity reagents to particular epitopes within proteins. However, in some embodiments, methods discussed herein may be expanded to different lengths of epitopes other than trimers. In some embodiments, protein-level fluorescence measurements may be used to derive a fractional contribution to the fluorescence measurement from individual epitopes, such as from each individual epitope. In some embodiments, protein binding may be modeled as a linear combination of a count of each of the 8000 possible trimers in the protein sequence and the fractional fluorescence from those trimers. This may be expressed as:

$$F_{pr} = \sum_{t=1}^{t=8000} c_{t,pr}\beta_t$$

Where:
$F_p$=Measurement (e. g. fluorescence) for protein pr
$c_{t,pr}$=Count of trimer t in protein pr
$\beta_t$=Fractional fluorescence from binding of affinity reagent to trimer t In some embodiments, measurements for an affinity reagent against multiple proteins may form a linear system of equations:

$$\vec{F} = C\vec{\beta} + \varepsilon$$

Where:
$\vec{F}$ is a length N column vector containing the observed measurement (e.g. fluorescence) for each protein
C is an N×8000 matrix of trimer counts with each column being counts for a particular trimer in each measured protein
$\vec{\beta}$ is a length 8000 column vector of fractional fluorescence from binding of the reagent to each possible trimer
$\varepsilon$ is a scalar constant to correct for background binding or a noise floor In some embodiments, methods provided herein may include non-standard amino acids and/or model n-mers of different length. In the case of known NAPPA or similar binding measurements, $\vec{F}$ and C are known variables, and values for $\vec{\beta}$ and $\varepsilon$ may be derived by linear regression or related approaches. In particular, non-negative least squares and non-negative least absolute shrinkage and selection operator (LASSO) regression may be well-suited for considerations of methods described herein. Non-negative least squares bounds the solution $\vec{\beta}$ to be non-negative, and non-negative LASSO regression further imposes a sparsity constraint. LASSO regression is particularly effective when the system is underdetermined, that is, when the number of unique proteins measured is less than the number of unique trimers (8,000 in this example). In some embodiments, the fractional fluorescence derived from each epitope may be used to estimate binding characteristics, such as binding kinetics, of particular affinity reagents to individual epitopes. In some embodiments, the relative fractional fluorescence may be considered proportional to relative binding affinity of the affinity reagent to each of the epitopes. In some embodiments, fractional fluorescence may be converted to a calculation of the fraction of sites bound by dividing by the number of fluorescent counts per fluorophore and then dividing by the expected number of protein molecules per spot on the array. A simulation of this method is provided in Example 5 where a set of binding affinities of a theoretical affinity reagent are used to predict binding of the affinity reagent to 720 human proteins, and the predicted binding data is then solved to determine the affinities of the affinity reagent to each possible trimer epitope.

Data that is gathered from embodiments of modeling protein to affinity reagent binding may be used to help train other models that predict protein binding affinity from the primary sequence of a protein. In some embodiments, data that is gathered from embodiments of modeling protein to affinity reagent binding may be used to help train other models that predict protein binding affinity from a derivative of the primary sequence (e.g. amino acid composition, trimer count, predicted three dimensional structure). In some embodiments, models may include similar parameters to those discussed with epitopes having different lengths (e.g. 1 mers, 2 mers, 4 mers, etc.) or a mixture of epitopes having different lengths. In some embodiments, models may use a non-linear model, for example with an exponential function relating trimer affinity to observed fluorescence or a multiplicative model where trimer-level affinities are multiplied to generate a protein level affinity. In some embodiments, a neural network may be used to predict protein binding affinity from protein sequence or trimer composition. Additionally, a support vector regression model may be used to predict protein binding affinity from protein sequence or trimer composition.

Assessing the Influence of Secondary Structure on Affinity Reagent Protein Binding Binding of affinity reagents to proteins may be influenced by the presence of secondary structural elements, such as helices, turns, loops, and sheets. In some embodiments, an approach leveraging peptide arrays and protein structure databases may be used to assess how binding of an affinity reagent to an epitope is altered by the presence of secondary structure. In some embodiments, information related to known protein structures may be used to identify regions of proteins which form different secondary structures, such as alpha helices and beta sheets, and which also contain epitopes of interest. In some embodiments, the epitopes of interest may be within the identified secondary structures. In some embodiments, the epitopes of interest may be nearby the identified secondary structures. In some embodiments, protein regions having known secondary structures may be synthesized and used to assess the binding of the affinity reagents compared to different protein regions which have not been observed to have secondary structure. In some embodiments, protein regions having known secondary structures may be synthesized and used to assess the binding of the affinity reagents as compared to scrambled sequences which contain the epitopes of interest and the same amino acid composition as the structured region but a different amino acid sequence.

In some embodiments, methods for measuring binding affinities of an affinity reagent to different secondary structures may involve using hundreds or thousands of peptides on printed peptide arrays such as those available from PEPperPRINT. For example, an array containing 11,000 peptides, each peptide having a length of 10-30 residues, may be printed and then hybridized with a fluorescently labeled affinity reagent. The amount of fluorescence measured at each spot on the array may be considered to be proportional to a binding affinity of an affinity reagent to a corresponding peptide localized at the spot. In some embodiments, methods may be provided to test for structural influence. For example, an array may be printed containing "structural" peptides—e.g. peptides such as 15 mers that may be expected to have a particular secondary structure that also contain the epitope of interest. Additionally, an array may alternatively or additionally be printed to include "unstructured" peptides that have not been observed to have secondary structure and that also include a same epitope of interest. "Unstructured" peptides may be constructed by modifying portions of a particular sequence so as to modify one or more sequences portions that are associated with secondary structures, thereby producing a modified sequence that is either observed to have less secondary structures than an original peptide or is observed as not having any secondary structures. By measuring the different indicators of binding affinity (e.g., an amount of fluorescence, or another indicator of attachment between the affinity reagents and the peptides), a determination may be made as to how the presence of secondary structural components may influence the particular binding affinities of particular affinity reagents with respect to one or more epitopes of interest.

Finding Structured Peptides

In some embodiments, sequences for structured peptides may be derived from regions of endogenous proteins that are known to be structured. In some embodiments, these peptides may be found by initially searching a reference proteome (e.g. Uniprot human reference proteome) to find all occurrences of the epitope in annotated protein sequences for the species of interest. Once the occurrences of the epitope in annotated protein sequences for the species of interest are identified, sequence locations containing epitopes may be cross-referenced with structural data from a protein database, such as Protein Data Bank (PDB). Additionally or alternatively, software that predicts secondary structures may be used to determine whether sequence locations containing epitopes are associated with a structural motif (e.g. a secondary structure) of interest. Software programs that may be used to predict secondary structure include, but are not limited to, Rosetta (https://www.rosettacommons.org/software), I-TASSER (https://zhanglab.ccmb.med.umich.edu/I-TASSER/), and PEP-FOLD (http://bioserv.rpbs.univ-paris-diderot.fr/services/PEP-FOLD/), among other examples.

Once sequence locations/sequence portions that are associated with structural data are identified, epitopes that are not within sequence portions associated with a structural motif of interest (e.g. beta sheet, alpha helix, turn) may be removed. Further, for each instance of the epitope that is within a structural element, the epitope and structured flanking sequence may be extracted from either side of the epitope. Several different extractions may be performed for each epitope, for example one where the epitope is at the beginning of the peptide, one where the epitope is near the middle of the peptide, and one with the epitope at the end of the peptide. In some cases, a peptide length may be selected, for example a peptide length may be less than 10, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more than 40 residues. In some embodiments, possible fragments of an epitope and flanking sequences may be selected. For example, in a case with an epitope length of 3 and a peptide length of 15, there are 13 different sequences which may be selected depending on whether the epitope starts at the $1^{st}$-$13^{th}$ positions of the peptide. In some cases multiple peptide lengths may be selected. Further, for each extracted peptide sequence (epitope+structured flanking sequence), "unstructured" peptides, where sequence portions associated with secondary structures are modified to alter or remove secondary structural characteristics. In some embodiments, "unstructured" peptides may be generated by shuffling one or more flanking sequences, but leaving the epitope in the same position. Shuffling a sequence may comprise changing the order of residues in the sequence while maintaining composition. Additionally, a composition may be regarded as a count of each residue in a sequence. In some embodiments, shuffling a sequence may comprise randomly altering the order of residues in the sequence while maintaining composition. In some embodiments, "unstructured" peptides may be generated by non-randomly altering the order of residues within a sequence while maintaining sequence composition. In some embodiments, "unstructured" peptides may be generated by incorporating non-natural or modified amino acid residues into a sequence. In some embodiments, "unstructured" peptides may be generated applying one or more of these methods in combination, in sequence, or to a subset of one or more flanking sequences associated with an epitope. In some embodiments, the secondary structures of the "unstructured" peptides may be assessed by synthesizing the peptides and using a method such as circular dichroism spectroscopy.

Assessing the Structured Peptides

Once structured and unstructured epitope containing peptides have been identified as above an array may be printed with many replicates of each of the structured and unstructured peptides. The array may then be hybridized with a fluorescently labeled affinity reagent. The amount of fluorescence measured at each spot on the array may be measured and a paired t-test comparing fluorescence measurements between the structured and unstructured peptides may be performed to determine if there is a significant increase or decrease in binding, e.g. due to secondary structure. If the fluorescence of the structured peptides is decreased relative to the unstructured peptides, this may indicate some degree of disruption of affinity reagent binding due to secondary structural elements. Due to challenges of protein folding, it is possible that not all of the "structured" peptides will fold into the predicted 'native' conformations when printed on an array. Use of multiple different structured peptide sequences and redundant fragments for each epitope may help to address this challenge. Any peptide which shows a significant change in binding affinity compared to other peptides with the same epitope may be selected for further study. For example, the peptide may be assessed by circular dichroism spectroscopy (CD spectroscopy) to determine whether it has adopted the expected secondary structure. In some cases, all peptides may be assessed by CD spectroscopy to determine the secondary structures prior to hybridization with the affinity reagents.

An alternative method for assessing the effect of secondary structure on affinity reagent binding may be to use full length proteins, either from cell free expression or from cell lysates. In some cases highly structured proteins may be isolated from tissue samples, for example prion proteins, amyloid plaques, or tau fibrils. For example, samples of different recombinant proteins with known secondary structures may be obtained and used to assess the binding of the affinity reagents to the structured proteins compared to unstructured proteins, scrambled proteins, or denatured proteins. The method as described above may be used for any epitopes which are located within structured regions of the selected structured proteins. The proteins may be bound to a solid support to facilitate the assessment of binding, or may be maintained in solution and methods such as affinity pull down may be used to assess binding.

In some cases, the peptide qualification screen and protein qualification screen may be performed to select affinity reagents with desired properties. In other cases the affinity reagents may be selected before performing either of the screens, and the screens may be performed to collect binding data about the affinity reagents.

Screening and selection steps may be performed for all possible epitopes of a given n-mer, for example for all 8000 possible 3-mers. In some cases, screening steps may only be performed for a subset of the possible n-mers. For example, rather than screening for affinity reagents for all 8000 3-mers, 800 3-mers may be selected as desired epitopes and the other 7200 3-mers may not be screened against.

In some cases, an affinity reagent selected using the methods described herein may bind to about 50% of all possible proteins in a proteome. In some cases, a plurality of affinity reagents with different binding properties may be selected and pooled together such that the affinity reagent pool binds to about half of all proteins in a proteome. In some cases, an affinity reagent pool may be used in place of a single affinity reagent.

Affinity reagents may be any reagents which bind proteins or peptides with reproducible specificity. For example the affinity reagents may be antibodies, antibody fragments, aptamers, or peptides. In some examples, monoclonal antibodies may be preferred. In some examples, antibody fragments such as Fab fragments may be preferred. In some examples, aptamers may be preferred. In some cases the affinity reagents may be commercially available affinity reagents, such as commercially available antibodies. In some cases the desired affinity reagents may be selected by screening commercially available affinity reagents to identify those with useful characteristics. In some cases, affinity reagents may be screened for their ability to bind a single protein. In some cases, affinity reagents may be screened for their ability to bind an epitope or amino-acid sequence. In some cases, groups of affinity reagents may be screened for their ability to collectively resolve similar proteins (e.g those with highly similar sequence) through differential binding. In some cases, affinity reagents may be screened for overlapping binding characteristics to increase binding specificity for a particular protein. Screening of affinity reagents may be performed in a variety of different ways. One example would be to screen affinity reagents against a NAPPA or an epitope tiling array. In some cases, protein-specific affinity reagents designed to bind to a protein target may be used (e.g. commercially available antibodies or aptamers). In some cases, multiple protein-specific, or epitope specific, affinity reagents may be mixed prior to performing a binding measurement. For example, for each binding measurement pass, a new mixture of protein specific affinity reagents may be selected comprising a subset of the available affinity reagents selected at random from the complete set. For example, each subsequent mixture may be generated in the same random manner, with the expectation that many of the affinity reagents will be present in more than one of the mixtures. In some cases, protein identifications may be generated more rapidly using mixtures of protein-specific affinity reagents. In some cases, such mixtures of protein-specific affinity reagents may increase the percentage of unknown proteins for which an affinity reagent binds in any individual pass. Mixtures of affinity reagents may consist of 1%, 5%, 10%, 20%, 30%, 40%, 50%, 60%, 70%, 80%, 90% or more of all available affinity reagents.

The affinity reagents may have high, moderate or low specificity. In some examples the affinity reagents may recognize several different epitopes. In some examples the affinity reagents may recognize epitopes present in two or more different proteins. In some examples the affinity reagents may recognize epitopes present in many different proteins. In some cases an affinity reagent used in the methods of this disclosure may be highly specific for a single epitope. In some cases an affinity reagent used in the methods of this disclosure may be highly specific for a single epitope containing a posttranslational modification.

In some embodiments, an affinity reagent that is directed towards identifying a target amino acid sequence may actually comprise a group of different components which are not differentiated or distinguishable from each other as used in methods described herein. In particular, the different components that may be used to identify the same target amino acid sequence may use the same detection moiety to identify the same target amino acid sequence. For example, an affinity reagent which binds a trimer amino acid sequence (AAA) regardless of flanking sequences may comprise either a single probe which binds the trimer AAA sequence without any effect from flanking sequences, or a group of 400 probes, each of which binds to a different 5 amino acid epitope of the form $\alpha AAA\beta$, where $\alpha$ and $\beta$ may be any amino acid. In the some cases of the second case, the 400 probes may be combined such that there is an equal amount of each one. In some cases of the second case, the 400 probes may be combined such that the amounts of each probe may be weighted by the characteristic binding affinities of each probe such that there is an equal probability of any given 5 amino acid epitope being bound.

Novel affinity reagents may be generated by any method known in the art. Methods of developing affinity reagents include SELEX, phage display, and inoculation. In some examples affinity reagents may be designed using structure based drug design methods. Structure-based drug design (or direct drug design) utilizes knowledge of the three dimensional structure of the epitope of interest and the binding site of the affinity reagent.

In some cases the affinity reagents may be labeled with nucleic acid barcodes. In some examples, nucleic acid barcodes may be used to purify affinity reagents after use. In some examples, nucleic acid barcodes may be used to sort the affinity reagents for repeated uses. In some cases the affinity reagents may be labeled with fluorophores which may be used to sort the affinity reagents after use.

In some cases, multiple affinity reagents that are labeled with nucleic acid barcodes may be multiplexed and then detected using complementary nucleic acid probes. A multiplexed group of affinity reagents may be detected in a single cycle using multiple complementary nucleic acids with distinct detection moieties. In some cases, a multiplexed group of affinity reagents may be detected in multiple cycles using a single complementary nucleic acid conjugated to a detection moiety. In some cases, a multiplexed group of affinity reagents may be detected in multiple cycles using multiple complementary nucleic acids each conjugated to a distinct detection moiety. In some cases, a multiplexed group of affinity reagents may be detected in multiple cycles using multiple complementary nucleic acids each conjugated to a distinct group detection moieties.

In some cases, one or more affinity reagents, that are labeled with nucleic acid barcodes, may be cross-linked to a bound protein. Once the one or more affinity reagents are cross-linked to the protein, the barcodes may be sequenced to determine the identity of the cross-linked affinity reagent. In some cases, multiple bound proteins may be exposed to the one or more affinity reagents. In some cases, when multiple bound proteins are cross-linked with one or more affinity reagents, the barcodes associated with the bound affinity reagents may be sequenced to determine the identity of the cross-linked affinity reagents associated with each of the multiple bound proteins.

The family of affinity reagents may comprise one or more types of affinity reagents. For example the methods of the present disclosure may use a family of affinity reagents comprising one or more of antibodies, antibody fragments, Fab fragments, aptamers, peptides, and proteins.

The affinity reagents may be modified. Modifications include, but are not limited to, attachment of a detection moiety. Detection moieties may be directly or indirectly attached. For example the detection moiety may be directly covalently attached to the affinity reagent, or may be attached through a linker, or may be attached through an affinity reaction such as complementary nucleic acid tags or a biotin streptavidin pair. Attachment methods that are able to withstand gentle washing and elution of the affinity reagent may be preferred.

Detection moieties include, but are not limited to, fluorophores, bioluminescent proteins, nucleic acid segments including a constant region and barcode region, or chemical tethers for linking to a nanoparticle such as a magnetic particle. Detection moieties may include several different flurophores with different patterns of excitation or emission.

The detection moiety may be cleavable from the affinity reagent. This can allow for a step in which the detection moieties are removed from affinity reagents that are no longer of interest to reduce signal contamination.

In some cases the affinity reagents are unmodified. For example if the affinity reagent is an antibody then the presence of the antibody may be detected by atomic force microscopy. The affinity reagents may be unmodified and may be detected, for example, by having antibodies specific to one or more of the affinity reagents. For example if the affinity reagent is a mouse antibody then the mouse antibody may be detected by using an anti-mouse secondary antibody. Alternately the affinity reagent may be an aptamer which is detected by an antibody specific for the aptamer. The secondary antibody may be modified with a detection moiety as described above. In some cases the presence of the secondary antibody may be detected by atomic force microscopy.

In some examples, the affinity reagents may comprise the same modification, for example a conjugated green fluorescent protein, or may comprise two or more different types of modification. For example, each affinity reagent may be conjugated to one of several different fluorescent moieties, each with a different wavelength of excitation or emission. This may allow multiplexing of the affinity reagents as several different affinity reagents may be combined and/or distinguished. In one example, a first affinity reagent may be conjugated to a green fluorescent protein, a second affinity reagent may be conjugated to a yellow fluorescent protein and a third affinity reagent may be conjugated to a red fluorescent protein, thus the three affinity reagents can be multiplexed and identified by their fluorescence. In a further example a first, fourth and seventh affinity reagent may be conjugated to a green fluorescent protein, a second, fifth and eighth affinity reagent may be conjugated to a yellow fluorescent protein and a third, sixth and ninth affinity reagent may be conjugated to a red fluorescent protein; in this case the first, second and third affinity reagents may be multiplexed together while the second, fourth and seventh, and third, sixth and ninth affinity reagents form two further multiplexing reactions. The number of affinity reagents which can be multiplexed together may depend on the detection moieties used to differentiate them. For example, the multiplexing of affinity reagents labeled with fluorophores may be limited by the number of unique fluorophores available. For further example, the multiplexing of affinity reagents labeled with nucleic acid tags may be determined by the length of the nucleic acid bar code.

The specificity of each affinity reagent can be determined prior to use in an assay. The binding specificity of the affinity reagents can be determined in a control experiment using known proteins. Any appropriate experimental methods may be used to determine the specificity of the affinity reagent. In one example a solid support may be loaded with known protein standards at known locations and used to assess the specificity of a plurality of affinity reagents. In another example, a solid support may contain both experimental samples and a panel of controls and standards such that the specificity of each affinity reagent can be calculated from the binding to the controls and standards and then used to identify the experimental samples. In some cases affinity reagents with unknown specificity may be included along with affinity reagents of known specificity, data from the known specificity affinity reagents may be used to identify proteins, and the pattern of binding of the unknown specificity affinity reagents to the identified proteins may be used to determine their binding specificity. It is also possible to reconfirm the specificity of any individual affinity reagent by using the known binding data of other affinity reagents to assess which proteins the individual affinity reagent bound. Thus with multiple uses of an affinity reagent panel the specificities of the affinity reagents may be increasingly refined with each iteration. While affinity reagents that are uniquely specific to particular proteins may be used, methods described herein may not require them. Additionally, methods may be effective on a range of specificities. In some examples, methods described herein may be particularly efficient when affinity reagents are not specific to any particular protein, but are instead specific to amino acid motifs (e.g. the tri-peptide AAA).

In some examples, one or more affinity reagents may be chosen to bind amino acid motifs of a given length, such as 2, 3, 4, 5, 6, 7, 8, 9, 10, or more than 10 amino acids. In some examples, one or more affinity reagents may be chosen to bind amino acid motifs of a range of different lengths from 2 amino acids to 40 amino acids.

In some examples, the affinity reagents may be chosen to have high, moderate, or low binding affinities. In some cases affinity reagents with low or moderate binding affinities may be preferred. In some cases the affinity reagents may have dissociation constants of about $10^{-3}$ M, $10^{-4}$ M, $10^{-5}$ M, $10^{-6}$ M, $10^{-7}$ M, $10^{-8}$ M, $10^{-9}$ M, $10^{-10}$ M or lower. In some cases the affinity reagents may have dissociation constants of greater than about $10^{-10}$ M, $10^{-9}$ M, $10^{-8}$ M, $10^{-7}$ M, $10^{-6}$ M, $10^{-5}$ M, $10^{-4}$ M, $10^{-3}$ M, $10^{-2}$ M or higher.

Some of the affinity reagents may be chosen to bind modified amino acid sequences, such as phosphorylated or ubiquinated amino acid sequences. In some examples, one or more affinity reagents may be chosen to be broadly specific for a family of epitopes that may be contained by one or more proteins. In some examples, one or more affinity reagents may bind two or more different proteins. In some examples, one or more affinity reagents may bind weakly to their target or targets. For example, affinity reagents may bind less than 10%, less than 10%, less than 15%, less than 20%, less than 25%, less than 30%, less than 35%, or less than 35% to their target or targets. In some examples, one or more affinity reagents may bind moderately or strongly to their target or targets. For example, affinity reagents may bind more than 35%, more than 40%, more than 45%, more than 60%, more than 65%, more than 70%, more than 75%, more than 80%, more than 85%, more than 90%, more than 91%, more than 92%, more than 93%, more than 94%, more than 95%, more than 96%, more than 97%, more than 98%, or more than 99% to their target or targets.

To compensate for weak binding, an excess of the affinity reagent may be applied to the solid support. The affinity reagent may be applied at about a 1:1, 2:1, 3:1, 4:1, 5:1, 6:1, 7:1, 8:1, 9:1 or 10:1 excess relative to the sample proteins. The affinity reagent may be applied at about a 1:1, 2:1, 3:1, 4:1, 5:1, 6:1, 7:1, 8:1, 9:1 or 10:1 excess relative to the expected incidence of the epitope in the sample proteins.

The affinity reagents may also comprise a magnetic component. The magnetic component may be useful for manipulating some or all bound affinity reagents into the same imaging plane or z stack. Manipulating some or all affinity reagents into the same imaging plane may improve the quality of the imaging data and reduce noise in the system.

Substrates/Solid Supports

In some embodiments, peptides may be applied to a functionalized substrate, such as a solid support, to facilitate the affinity reagent selection or screening steps. FIG. 3B shows an example of a solid support with arrayed peptides conjugated to the solid support for use in an affinity reagent characterization screen to determine the effect of flanking sequence on the binding of an affinity reagent to the epitope AAA. In some cases, the target peptides may be directly applied to a solid support. In some cases, the target peptides may be synthesized or grown on a solid support. In some cases, peptides may be synthesized on a solid support such as an array or beads. For example, a peptide array may be manufactured to contain multiple copies of a single peptide sequence at each location on the array. Custom peptide microarrays may also be bought commercially, for example PEPperPRINT.

The substrate may be any substrate capable of forming a solid support. Substrates, such as solid supports, as used herein can refer to any solid surface to which peptides can be covalently or non-covalently attached. Non-limiting examples of solid supports include particles, beads, slides, surfaces of elements of devices, membranes, flow cells, wells, chambers, macrofluidic chambers, microfluidic chambers, channels, microfluidic channels, or any other surfaces. Solid support surfaces can be flat or curved, or can have other shapes, and can be smooth or textured. Solid support surfaces may contain microwells. In some embodiments, a solid support can be composed of glass, carbohydrates such as dextrans, plastics such as polystyrene or polypropylene, polyacrylamide, latex, silicon, metals such as gold, or cellulose, and may be further modified to allow or enhance covalent or non-covalent attachment of the oligonucleotides. For example, a solid support surface may be functionalized by modification with specific functional groups, such as maleic or succinic moieties, or derivatized by modification with a chemically reactive group, such as amino, thiol, or acrylate groups, such as by silanization. Suitable silane reagents include aminopropyltrimethoxysilane, aminopropyltriethoxysilane and 4-aminobutyltriethoxysilane. The solid support may be functionalized with N-Hydroxysuccinimide (NHS) functional groups. Glass surfaces can also be derivatized with other reactive groups, such as acrylate or epoxy, using, e.g., epoxysilane, acrylatesilane or acrylamidesilane. The solid support and process for oligonucleotide attachment are preferably stable for repeated binding, washing, imaging and eluting steps. In some examples, the solid support may be a slide or a flow cell.

The spacing of the functional groups on the solid support may be ordered or random. An ordered array of functional groups may be created by photolithography. Functional groups in an ordered array may be located such that each functional group is at least about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, or about 1000 nm from any other functional group. Functional groups in a random spacing may be provided at a concentration such that functional groups are on average at least about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, or about 1000 nm from any other functional group.

A substrate, such as a solid support, may be indirectly functionalized. For example, a solid support may be PEGylated and a functional group may be applied to all or a subset of the PEG molecules.

A substrate may comprise any material, including metals, glass, plastics, ceramics or combinations thereof. In some preferred embodiments, the solid support can be a flow cell. The flow cell can be composed of a single layer or multiple layers. For example, a flow cell can comprise a base layer (e.g., of boro silicate glass), a channel layer (e.g., of etched silicon) overlaid upon the base layer, and a cover, or top, layer. When the layers are assembled together, enclosed channels can be formed having inlet/outlets at either end through the cover. The thickness of each layer can vary, but is preferably less than about 1700 µm. Layers can be composed of any suitable material known in the art, including but not limited to photosensitive glasses, borosilicate glass, fused silicate, PDMS or silicon. Different layers can be composed of the same material or different materials.

In some embodiments, flow cells can comprise openings for channels on the bottom of the flow cell. A flow cell can comprise millions of attached target conjugation sites in locations that can be discretely visualized. In some embodiments, various flow cells of use with embodiments of the invention can comprise different numbers of channels (e.g., 1 channel, 2 or more channels, 3 or more channels, 4 or more channels, 6 or more channels, 8 or more channels, 10 or more channels, 12 or more channels, 16 or more channels, or more than 16 channels). Various flow cells can comprise channels of different depths or widths, which may be different between channels within a single flow cell, or different between channels of different flow cells. A single channel can also vary in depth and/or width. For example, a channel can be less than about 50 µm deep, about 50 µm deep, less than about 100 µm deep, about 100 µm deep, about 100 µm io about 500 µm deep, about 500 µm deep, or more than about 500 µm deep at one or more points within the channel. Channels can have any cross sectional shape, including but not limited to a circular, a semi-circular, a rectangular, a trapezoidal, a triangular, or an ovoid cross-section.

The peptides may be spotted, dropped, pipetted, flowed, washed or otherwise applied to the solid support. In the case of a solid support that has been functionalized with a moiety such as an NHS ester, no modification of the peptide is required. In the case of a solid support that has been functionalized with alternate moieties (e.g. a sulfhydryl, amine, or linker DNA), a crosslinking reagent (e.g. disuccinimidyl suberate, NHS, sulphonamides) may be used. In the case of a solid support that has been functionalized with linker DNA the peptides of the target may be modified with complementary DNA tags.

Photo-activatable cross linkers may be used to direct cross linking of a sample to a specific area on the solid support. Photo-activatable cross linkers may be used to allow multiplexing of peptide samples by attaching each sample in a known region of the solid support. Photo-activatable cross linkers may allow the specific attachment of peptides which have been successfully tagged, for example by detecting a fluorescent tag before cross linking a peptide. Examples of photo-activatable cross linkers include, but are not limited to, N-5-azido-2-nitrobenzoyloxysuccinimide, sulfosuccinimidyl 6-(4'-azido-2'-nitrophenylamino)hexanoate, succinimidyl 4,4'-azipentanoate, sulfosuccinimidyl 4,4'-azipentanoate, succinimidyl 6-(4,4'-azipentanamido)hexanoate, sulfosuccinimidyl 6-(4,4'-azipentanamido)hexanoate, succinimidyl 2-((4,4'-azipentanamido)ethyl)-1,3'-dithiopropionate, and sulfosuccinimidyl azipentanamido)ethyl)-1,3'-dithiopropionate.

The peptides may be attached to the substrate by one more residues. In some examples, the peptides may be attached via the N terminal, C terminal, both terminals, or via an internal residue.

In some embodiments, each peptide sequence may be associated with a unique spatial address. For example, once the peptides are attached to the solid support in spatially separated locations, each peptide sequence can be assigned an indexed address, such as by coordinates. In some examples, a grid of pre-assigned unique spatial addresses may be predetermined. In some embodiments the solid support may contain easily identifiable fixed marks such that placement of each peptide can be determined relative to the fixed marks of the solid support. In some examples, the solid support may have grid lines and/or and "origin" or other fiducials permanently marked on the surface. In some examples, the surface of the solid support may be permanently or semi-permanently marked to provide a reference by which to locate cross linked peptides. The shape of the patterning itself, such as the exterior border of the conjugated peptides may also be used as fiducials for determining the unique location of each spot.

Use of Affinity Reagents to Identify Proteins

The affinity reagents of this disclosure may be used to identify and quantify proteins in a sample. In some examples, the approach can comprise three aspects: 1) an addressable substrate in which proteins and/or protein fragments can be conjugated; 2) a set of affinity reagents, e.g. where each affinity reagent can bind to a peptide with varying specificity; and 3) a software that is able to use a combination of prior knowledge about the binding characteristics of the affinity reagents, the specific pattern of binding of affinity reagents at each address in the substrate, and/or a database of the possible sequences of the proteins in the mixture (e.g. the human proteome) to infer the identity of a protein at a precise spatial address in the substrate. In some examples, the precise spatial address may be a unique spatial address. In some embodiments, affinity reagents having reproducible affinities for one or more epitopes that may be present in a sample may be used with this method. An affinity reagent which binds to different epitopes, or with different affinities to epitopes in every assay may not be suitable for this method.

Samples

The samples may be any biological sample containing protein. The samples may be taken from tissue or cells or from the environment of tissue or cells. In some examples, the sample could be a tissue biopsy, blood, blood plasma, extracellular fluid, cultured cells, culture media, discarded tissue, plant matter, synthetic proteins, archael, bacterial and/or viral samples, fungal tissue, archaea, or protozoans. In some examples, the protein is isolated from its primary source (cells, tissue, bodily fluids such as blood, environmental samples etc) during sample preparation. The protein may or may not be purified from its primary source. In some cases the primary source is homogenized prior to further processing. In some cases cells are lysed using a buffer such as RIPA buffer. Denaturing buffers may also be used at this stage. The sample may be filtered or centrifuged to remove lipids and particulate matter. The sample may also be purified to remove nucleic acids, or may be treated with RNases and DNases. The sample may contain intact proteins, denatured proteins, protein fragments or partially degraded proteins.

The sample may be taken from a subject with a disease or disorder. The disease or disorder may be an infectious disease, an immune disorder or disease, a cancer, a genetic disease, a degenerative disease, a lifestyle disease, an injury, a rare disease or an age related disease. The infectious disease may be caused by bacteria, viruses, fungi and/or parasites. Non-limiting examples of cancers include Bladder cancer, Lung cancer, Brain cancer, Melanoma, Breast cancer, Non-Hodgkin lymphoma, Cervical cancer, Ovarian cancer, Colorectal cancer, Pancreatic cancer, Esophageal cancer, Prostate cancer, Kidney cancer, Skin cancer, Leukemia, Thyroid cancer, Liver cancer, and Uterine cancer. Some examples of genetic diseases or disorders include, but are not limited to, cystic fibrosis, Charcot-MarieTooth disease, Huntington's disease, Peutz-Jeghers syndrome, Down syndrome, Rheumatoid arthritis, and Tay-Sachs disease. Non-limiting examples of lifestyle diseases include obesity, diabetes, arteriosclerosis, heart disease, stroke, hypertension, liver cirrhosis, nephritis, cancer, chronic obstructive pulmonary disease (copd), hearing problems, and chronic backache. Some examples of injuries include, but are not limited to, abrasion, brain injuries, bruising, burns, concussions, congestive heart failure, construction injuries, dislocation, flail chest, fracture, hemothorax, herniated disc, hip pointer, hypothermia, lacerations, pinched nerve, pneumothorax, rib fracture, sciatica, spinal cord injury, tendons ligaments fascia injury, traumatic brain injury, and whiplash. The sample may be taken before and/or after treatment of a subject with a disease or disorder. Samples may be taken before and/or after a treatment. Samples may be taken during a treatment or a treatment regime. Multiple samples may be taken from a subject to monitor the effects of the treatment over time. The sample may be taken from a subject known or suspected of having an infectious disease for which diagnostic antibodies are not available.

The sample may be taken from a subject suspected of having a disease or a disorder. The sample may be taken from a subject experiencing unexplained symptoms, such as fatigue, nausea, weight loss, aches and pains, weakness, or memory loss. The sample may be taken from a subject having explained symptoms. The sample may be taken from a subject at risk of developing a disease or disorder due to factors such as familial history, age, environmental exposure, lifestyle risk factors, or presence of other known risk factors.

The sample may be taken from an embryo, fetus, or pregnant woman. In some examples, the sample may comprise of proteins isolated from the mother's blood plasma. In some examples, the sample may comprise proteins isolated from circulating fetal cells in the mother's blood. In some cases, the sample may comprise proteins isolated from amniotic fluid.

Protein may be treated to remove modifications that may interfere with epitope binding. For example the protein may be glycosidase treated to remove post translational glycosylation. The protein may be treated with a reducing agent to reduce disulfide binds within the protein. The protein may be treated with a phosphatase to remove phosphate groups. Other non-limiting examples of post translational modifications that may be removed include acetate, amide groups, methyl groups, lipids, ubiquitin, myristoylation, palmitoylation, isoprenylation or prenylation (e.g. farnesol and geranylgeraniol), farnesylation, geranylgeranylation, glypiation, lipoylation, flavin moiety attachment, phosphopantetheinylation, and retinylidene Schiff base formation. Samples may also be treated to retain posttranslational protein modifications. In some examples, phosphatase inhibitors may be added to the sample. In some examples, oxidizing agents may be added to protect disulfide bonds.

Next, proteins may be denatured in full or in part. In some embodiments, proteins can be fully denatured. Proteins may be denatured by application of an external stress such as a detergent, a strong acid or base, a concentrated inorganic salt, an organic solvent (e.g., alcohol or chloroform), radiation or heat. Proteins may be denatured by addition of a denaturing buffer. Proteins may also be precipitated, lyophilized and suspended in denaturing buffer. Proteins may be denatured by heating. Methods of denaturing that are unlikely to cause chemical modifications to the proteins may be preferred.

Proteins of the sample may be treated to produce shorter polypeptides, either before or after conjugation. Remaining proteins may be partially digested with an enzyme such as ProteinaseK to generate fragments or may be left intact. In further examples the proteins may be exposed to proteases such as trypsin. Additional examples of proteases may include serine proteases, cysteine proteases, threonine proteases, aspartic proteases, glutamic proteases, metalloproteases, and asparagine peptide lyases.

In some cases it may be useful to remove extremely large and small proteins (e.g. Titin), such proteins may be removed by filtration or other appropriate methods. In some examples, extremely large proteins may include proteins that are over 400 kD, 450 kD, 500 kD, 600 kD, 650 kD, 700 kD, 750 kD, 800 kD or 850 kD. In some examples, extremely large proteins may include proteins that are over about 8,000 amino acids, about 8,500 amino acids, about 9,000 amino acis, about 9,500 amino acids, about 10,000 amino acids, about 10,500 amino acids, about 11,000 amino acids or about 15,000 amino acids. In some examples, small proteins may include proteins that are less than about 10 kD, 9 kD, 8 kD, 7 kD, 6 kD, 5 kD, 4 kD, 3 kD, 2 kD or 1 kD. In some examples, small proteins may include proteins that are less than about 50 amino acids, 45 amino acids, 40 amino acids, 35 amino acids or about 30 amino acids. Extremely large or small proteins can be removed by size exclusion chromatography. Extremely large proteins may be isolated by size exclusion chromatography, treated with proteases to produce moderately sized polypeptides and recombined with the moderately size proteins of the sample.

In some cases, proteins may be ordered by size. In some cases, proteins may be ordered by sorting proteins into microwells. In some cases, proteins may be ordered by sorting proteins into nanowells. In some cases, proteins may be ordered by running proteins through a gel such as an SDS-PAGE gel. In some cases, proteins may be ordered by other size-dependent fractionation methods. In some cases, proteins may be separated based on charge. In some cases, proteins may be separated based on hydrophobicity. In some cases, proteins may be separated based on other physical characteristics. In some cases, proteins may be separated under denaturing conditions. In some cases, proteins may be separated under non-denaturing conditions. In some cases, different fractions of fractionated proteins may be placed on different regions of the substrate. In some cases, different portions of separated proteins may be placed on different regions of the substrate. In some cases, a protein sample may be separated in an SDS-PAGE gel and transferred from the SDS-PAGE gel to the substrate such that the proteins are sorted by size in a continuum. In some cases, a protein sample may be sorted into three fractions based on size, and the three fractions may be applied to a first, second, and third region of the substrate, respectively. In some cases, proteins used in the systems and methods described herein may be sorted. In some cases, proteins used in the systems and methods described herein may not be sorted.

Proteins may be tagged, e.g. with identifiable tags, to allow for multiplexing of samples. Some non-limiting examples of identifiable tags include: fluorophores or nucleic acid barcoded base linkers. Fluorophores used may include fluorescent proteins such as GFP, YFP, RFP, eGFP, mCherry, tdtomato, FITC, Alexa Fluor 350, Alexa Fluor 405, Alexa Fluor 488, Alexa Fluor 532, Alexa Fluor 546, Alexa Fluor 555, Alexa Fluor 568, Alexa Fluor 594, Alexa Fluor 647, Alexa Fluor 680, Alexa Fluor 750, Pacific Blue, Coumarin, BODIPY FL, Pacific Green, Oregon Green, Cy3, Cy5, Pacific Orange, TRITC, Texas Red, R-Phycoerythrin, Allophcocyanin, or other fluorophores known in the art.

Any number of protein samples may be multiplexed. For example a multiplexed reaction may contain proteins from 2, 3, 4, 5, 6, 7, 8, 9, 10, 11, 12, 13, 14, 15, 16, 17, 18, 19, about 20, about 25, about 30, about 35, about 40, about 45, about 50, about 55, about 60, about 65, about 70, about 75, about 80, about 85, about 90, about 95, about 100 or more than 100 initial samples. The identifiable tags may provide a way to interrogate each protein as to its sample of origin, or may direct proteins from different samples to segregate to different areas on a solid support.

Substrate

In some embodiments, the proteins are then applied to a functionalized substrate to chemically attach proteins to the substrate. In some cases, the proteins may be attached to the substrate via biotin attachment. In some cases, the proteins may be attached to the substrate via nucleic acid attachment. In some embodiments, the proteins may be applied to an intermediate substance, where the intermediate substance is then attached to the substrate. In some cases, proteins may be conjugated to beads (e.g., gold beads) which may then be captured on a surface (e.g., a thiolated surface). In some cases, one protein may be conjugated to each bead. In some cases, proteins may be conjugated to beads (e.g., one protein per bead) and the beads may be captured on a surface (e.g. in microwells and/or nanowells).

The substrate may be any substrate capable of forming a solid support. Substrates, or solid substrates, as used herein can refer to any solid surface to which proteins can be covalently or non-covalently attached. Non-limiting examples of solid substrates include particles, beads, slides, surfaces of elements of devices, membranes, flow cells, wells, chambers, macrofluidic chambers, be flat or curved, or can have other shapes, and can be smooth or textured. In some cases, substrate surfaces may contain microwells. In some cases, substrate surfaces may contain nanowells. In some cases, substrate surfaces may contain one or more microwells in combination with one or more nanowells. In some embodiments, the substrate can be composed of glass, carbohydrates such as dextrans, plastics such as polystyrene or polypropylene, polyacrylamide, latex, silicon, metals such as gold, or cellulose, and may be further modified to allow or enhance covalent or non-covalent attachment of the oligonucleotides. For example, the substrate surface may be functionalized by modification with specific functional groups, such as maleic or succinic moieties, or derivatized by modification with a chemically reactive group, such as amino, thiol, or acrylate groups, such as by silanization. Suitable silane reagents include aminopropyltrimethoxysilane, aminopropyltriethoxysilane and 4-aminobutyltriethoxysilane. The substrate may be functionalized with N-Hydroxysuccinimide (NHS) functional groups. Glass surfaces can also be derivatized with other reactive groups, such as acrylate or epoxy, using, e.g., epoxysilane, acrylatesilane or acrylamidesilane. The substrate and process for oligonucleotide attachment are preferably stable for repeated binding, washing, imaging and eluting steps. In some examples, the substrate may be a slide or a flow cell.

An ordered array of functional groups may be created by, for example, photolithography, Dip-Pen nanolithography, nanoimprint lithography, nanosphere lithography, nanoball lithography, nanopillar arrays, nanowire lithography, scanning probe lithography, thermochemical lithography, thermal scanning probe lithography, local oxidation nanolithography, molecular self-assembly, stencil lithography, or electron-beam lithography. Functional groups in an ordered array may be located such that each functional group is less than 200 nanometers (nm), or about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 675 nm, about 700 nm, about 725 nm, about 750 nm, about 775 nm, about 800 nm, about 825 nm, about 850 nm, about 875 nm, about 900 nm, about 925 nm, about 950 nm, about 975 nm, about 1000 nm, about 1025 nm, about 1050 nm, about 1075 nm, about 1100 nm, about 1125 nm, about 1150 nm, about 1175 nm, about 1200 nm, about 1225 nm, about 1250 nm, about 1275 nm, about 1300 nm, about 1325 nm, about 1350 nm, about 1375 nm, about 1400 nm, about 1425 nm, about 1450 nm, about 1475 nm, about 1500 nm, about 1525 nm, about 1550 nm, about 1575 nm, about 1600 nm, about 1625 nm, about 1650 nm, about 1675 nm, about 1700 nm, about 1725 nm, about 1750 nm, about 1775 nm, about 1800 nm, about 1825 nm, about 1850 nm, about 1875 nm, about 1900 nm, about 1925 nm, about 1950 nm, about 1975 nm, about 2000 nm, or more than 2000 nm from any other functional group. Functional groups in a random spacing may be provided at a concentration such that functional groups are on average at least about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm, or more than 100 nm from any other functional group.

The substrate may be indirectly functionalized. For example, the substrate may be PEGylated and a functional group may be applied to all or a subset of the PEG molecules. Additionally, as discussed above, in some cases beads (e.g., gold beads) may be conjugated, and then the beads may be captured on a surface (e.g., a thiolated surface). In some cases, one protein may be conjugated for to each bead. In some cases, proteins may be conjugated to beads (e.g., one protein per bead) and the beads may be captured on a surface (e.g. in microwells and/or nanowells).

The substrate may be functionalized using techniques suitable for microscaled or nanoscaled structures (e.g., an ordered structure such as microwells, nanowells, micropillars, single molecular arrays, nanoballs, nanopillars, or nanowires). In some cases, a substrate may have microwells of different sizes. In some cases, microwells may be 1 micrometer (μm), may be about 2 μm, about 3 μm, about 4 μm, about 5 μm, about 6 μm, about 7 μm, about 8 μm, about 9 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, about 200 μm, about 205 μm, about 210 μm, about 215 μm, about 220 μm, about 225 μm, about 230 μm, about 235 μm, about 240 μm, about 245 μm, about 250 μm, about 255 μm, about 260 μm, about 265 μm, about 270 μm, about 275 μm, about 280 μm, about 285 μm, about 290 μm, about 295 μm, about 300 μm, about 305 μm, about 310 μm, about 315 μm, about 320 μm, about 325 μm, about 330 μm, about 335 μm, about 340 μm, about 345 μm, about 350 μm, about 355 μm, about 360 μm, about 365 μm, about 370 μm, about 375 μm, about 380 μm, about 385 μm, about 390 μm, about 395 μm, about 400 μm, about 405 μm, about 410 μm, about 415 μm, about 420 μm, about 425 μm, about 430 μm, about 435 μm, about 440 μm, about 445 μm, about 450 μm, about 455 μm, about 460 μm, about 465 μm, about 470 μm, about 475 μm, about 480 μm, about 485 μm, about 490 μm, about 495 μm, about 500 μm, or more than 500 μm. In some cases, a substrate may have microwells that range in size from 5 μm to 500 μm. In some cases, a substrate may have microwells that range in size from about 5 μm to about 500 μm. In some cases, a substrate may have microwells that range in size from 10 μm to 100 μm. In some cases, a substrate may have microwells that range in size from about 10 μm to about 100 μm. In some cases, a substrate may have a range of different sized microwells such that proteins of different sizes may be sorted into different sized microwells. In some cases, microwells in the substrate may be distributed by size (e.g. with larger microwells distributed in a first region and with smaller microwells distributed in a second region). In some cases, a substrate may have microwells of about ten different sizes. In some cases, a substrate may have microwells of about 20 different sizes, about 25 different sizes, about 30 different sizes, about 35 different sizes, about 40 different sizes, about 45 different sizes, about 50 different sizes, about 55 different sizes, about 60 different sizes, about 65 different sizes, about 70 different sizes, about 75 different sizes, about 80 different sizes, about 85 different sizes, about 90 different sizes, about 95 different sizes, about 100 different sizes, or more than 100 different sizes.

In some cases, a substrate may have nanowells of different sizes. In some cases, nanowells may be about 100 nanometers (nm), about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, or between 950 nm and 1 micrometer. In some cases, a substrate may have nanowells that range in size from 100 nm to 1 micrometer. In some cases, a substrate may have nanowells that range in size from 100 nm to 500 nm. In some cases, a substrate may have a range of different sized nanowells such that proteins of different sizes may be sorted into different sized nanowells. In some cases, nanowells in the substrate may be distributed by size (e.g. with larger nanowells distributed in a first region and with smaller nanowells distributed in a second region). In some cases, a substrate may have nanowells of about ten different sizes. In some cases, a substrate may have nanowells of about 20 different sizes, or more than 30 different sizes.

In some cases, a substrate may have a range of different sized nanowells and/or microwells such that proteins of different sizes may be sorted into different sized nanowells and/or microwells. In some cases, nanowells and/or microwells in the substrate may be distributed by size (e.g. with larger microwells distributed in a first region and with smaller nanowells distributed in a second region). In some cases, a substrate may have nanowells and/or microwells of about ten different sizes. In some cases, a substrate may have nanowells and/or microwells of about 20 different sizes, about 25 different sizes, about 30 different sizes, about 35 different sizes, about 40 different sizes, about 45 different sizes, about 50 different sizes, about 55 different sizes, about 60 different sizes, about 65 different sizes, about 70 different sizes, about 75 different sizes, about 80 different sizes, about 85 different sizes, about 90 different sizes, about 95 different sizes, about 100 different sizes, or more than 100 different sizes.

The substrate may comprise any material, including metals, glass, plastics, ceramics or combinations thereof. In some preferred embodiments, the solid substrate can be a flow cell. The flow cell can be composed of a single layer or multiple layers. For example, a flow cell can comprise a base layer (e.g., of boro silicate glass), a channel layer (e.g., of etched silicon) overlaid upon the base layer, and a cover, or top, layer. When the layers are assembled together, enclosed channels can be formed having inlet/outlets at either end through the cover. The thickness of each layer can vary, but is preferably less than about 1700 μm. Layers can be composed of any suitable material known in the art, including but not limited to photosensitive glasses, borosilicate glass, fused silicate, PDMS or silicon. Different layers can be composed of the same material or different materials.

In some embodiments, flow cells can comprise openings for channels on the bottom of the flow cell. A flow cell can comprise millions of attached target conjugation sites in locations that can be discretely visualized. In some embodiments, various flow cells of use with embodiments of the invention can comprise different numbers of channels (e.g., 1 channel, 2 or more channels, 3 or more channels, 4 or more channels, 6 or more channels, 8 or more channels, 10 or more channels, 12 or more channels, 16 or more channels, or more than 16 channels). Various flow cells can comprise channels of different depths or widths, which may be different between channels within a single flow cell, or different between channels of different flow cells. A single channel can also vary in depth and/or width. For example, a channel can be less than about 50 μm deep, about 50 μm deep, less than about 100 μm deep, about 100 μm deep, about 100 μi about 500 μm deep, about 500 μm deep, or more than about 500 μm deep at one or more points within the channel. Channels can have any cross sectional shape, including but not limited to a circular, a semi-circular, a rectangular, a trapezoidal, a triangular, or an ovoid cross-section.

The proteins may be spotted, dropped, pipetted, flowed, washed or otherwise applied to the substrate. In the case of a substrate that has been functionalized with a moiety such as an NHS ester, no modification of the protein is required. In the case of a substrate that has been functionalized with alternate moieties (e.g. a sulfhydryl, amine, or linker nucleic acid), a crosslinking reagent (e.g. disuccinimidyl suberate, NHS, sulphonamides) may be used. In the case of a substrate that has been functionalized with linker nucleic acid the proteins of the sample may be modified with complementary nucleic acid tags.

In some cases, a protein may be conjugated to a nucleic acid. Using the nucleic acid, a nucleic acid nanoball may be formed, thereby having the protein linked to the nucleic acid nanoball. When the nucleic acid nanoball is attached to a substrate, the protein attached to the nucleic acid is attached to the substrate by way of the nucleic acid nanoball. A DNA nanoball can be attached (e.g. by adsorption or by conjugation) to a substrate. The substrate may have an amine functionalized surface to which the nucleic acid nanoballs can attach.

In some cases, a nucleic acid nanoball may be formed with a functionally active terminus (e.g. a maleimide, NHS-Ester, etc.). The protein may then be conjugated to the nanoball thereby having the protein linked to the nucleic acid nanoball. When the nucleic acid nanoball is attached to a substrate, the protein attached to the nucleic acid is attached to the substrate by way of the nucleic acid nanoball. A DNA nanoball can be attached (e.g. by adsorption or by conjugation) to a substrate. The substrate may have an amine functionalized surface to which the nucleic acid nanoballs can attach.

Photo-activatable cross linkers may be used to direct cross linking of a sample to a specific area on the substrate. Photo-activatable cross linkers may be used to allow multiplexing of protein samples by attaching each sample in a known region of the substrate. Photo-activatable cross linkers may allow the specific attachment of proteins which have been successfully tagged, for example by detecting a fluorescent tag before cross linking a protein. Examples of photo-activatable cross linkers include, but are not limited to, N-5-azido-2-nitrobenzoyloxysuccinimide, sulfosuccinimidyl 6-(4'-azido-2'-nitrophenylamino)hexanoate, succinimidyl 4,4'-azipentanoate, sulfosuccinimidyl 4,4'-azipentanoate, succinimidyl 6-(4,4'-azipentanamido)hexanoate, sulfosuccinimidyl 6-(4,4'-azipentanamido)hexanoate, succinimidyl 2-((4,4'-azipentanamido)ethyl)-1,3'-dithiopropionate, and sulfosuccinimidyl azipentanamido)ethyl)-1,3'-dithiopropionate.

Samples may also be multiplexed by restricting the binding of each sample to a discrete area on the substrate. For example the substrate may be organized into lanes. Another method for multiplexing is to apply the samples iteratively across the substrate, following each sample application with a protein detection step utilizing a nonspecific protein binding reagent or dye. In some cases, examples of dyes may include fluorescent protein gel stains such as SYPRO® Ruby, SYPRO® Orange, SYPRO® Red, SYPRO® Tangerine, and Coomassie™ Fluor Orange.

By tracking the locations of all proteins after each addition of sample it is possible to determine the stage at which each location on the substrate first contained a protein, and thus from which sample that protein was derived. This method may also determine the saturation of the substrate after each application of sample and allows for maximization of protein binding on the substrate. For example if only 30% of functionalized locations are occupied by protein after a first application of a sample then either a second application of the same sample or an application of a different sample may be made.

The polypeptides may be attached to the substrate by one more residues. In some examples, the polypeptides may be attached via the N terminal, C terminal, both terminals, or via an internal residue.

In addition to permanent crosslinkers, it may be appropriate for some applications to use photo-cleavable linkers and that doing so enables proteins to be selectively extracted from the substrate following analysis. In some cases photo-cleavable cross linkers may be used for several different multiplexed samples. In some cases photo-cleavable cross linkers may be used from one or more samples within a multiplexed reaction. In some cases a multiplexed reaction may comprise control samples cross linked to the substrate via permanent crosslinkers and experimental samples cross linked to the substrate via photo-cleavable crosslinkers.

Each conjugated protein may be spatially separated from each other conjugated protein such that each conjugated protein is optically resolvable. Proteins may thus be individually labeled with a unique spatial address. In some embodiments, this can be accomplished by conjugation using low concentrations of protein and low density of attachment sites on the substrate so that each protein molecule is spatially separated from each other protein molecule. In examples where photo-activatable crosslinkers are used, a light pattern may be used such that proteins are affixed to predetermined locations.

In some methods, bulk proteins that have been purified may be conjugated to a substrate and processed using methods described herein so as to identify the purified protein. Bulk proteins may comprise purified proteins that have been collected together. In some examples, bulk proteins may be conjugated at a location that is spatially separated from each other conjugated protein or bulk proteins such that each conjugated protein or bulk protein is optically resolvable. Proteins, or bulk proteins, may thus be individually labeled with a unique spatial address. In some embodiments, this can be accomplished by conjugation using low concentrations of protein and low density of attachment sites on the substrate so that each protein molecule is spatially separated from each other protein molecule. In examples where photo-activatable crosslinkers are used, a light pattern may be used such that one or more proteins are affixed to predetermined locations.

In some embodiments, each protein may be associated with a unique spatial address. For example, once the proteins are attached to the substrate in spatially separated locations, each protein can be assigned an indexed address, such as by coordinates. In some examples, a grid of pre-assigned unique spatial addresses may be predetermined. In some embodiments the substrate may contain easily identifiable fixed marks such that placement of each protein can be determined relative to the fixed marks of the substrate. In some examples the substrate may have grid lines and/or and "origin" or other fiducials permanently marked on the surface. In some examples the surface of the substrate may be permanently or semi-permanently marked to provide a reference by which to locate cross linked proteins. The shape of the patterning itself, such as the exterior border of the conjugated polypeptides may also be used as fiducials for determining the unique location of each spot.

The substrate may also contain conjugated protein standards and controls. Conjugated protein standards and controls may be peptides or proteins of known sequence which have been conjugated in known locations. In some examples, conjugated protein standards and controls may serve as internal controls in an assay. The proteins may be applied to the substrate from purified protein stocks, or may be synthesized on the substrate through a process such as Nucleic Acid-Programmable Protein Array (NAPPA).

In some examples, the substrate may comprise fluorescent standards. These fluorescent standards may be used to calibrate the intensity of the fluorescent signals from assay to assay. These fluorescent standards may also be used to correlate the intensity of a fluorescent signal with the number of fluorophores present in an area. Fluorescent standards may comprise some or all of the different types of fluorophores used in the assay.

Affinity Reagents

Once the substrate has been conjugated with the proteins from the sample, multi-affinity reagent measurements can be performed. The measurement processes described herein may utilize various affinity reagents as described herein.

Binding Measurements

Given a set of modified affinity reagents and a conjugated substrate, affinity reagents may be iteratively applied to the substrate. Each measurement cycle consists of several stages. In the first stage, affinity reagents are applied to the substrate where they may adsorb to the conjugated proteins.

Next, the substrate can be lightly washed to remove non-specific binding. This washing step can be performed under conditions which will not elute affinity reagents which have bound to the immobilized proteins. Some examples of buffers which could be used for this step include phosphate buffered saline, Tris buffered saline, phosphate buffered saline with Tween20, and Tris buffered saline with Tween20.

Following adsorption, the binding addresses for each modified affinity reagent are determined, such as through measurement of a fluorophore that has been conjugated to the affinity reagents directly, or to a complement nucleic acid to a nucleic acid strand conjugated to the affinity reagents. The detection method is determined by the choice of detection moiety. Fluorophores and bioluminescent moieties may be optically detected, in some cases secondary detection reagents are required. The unique address of each immobilized protein on the substrate may be determined prior to the binding measurements, or a list of addresses containing immobilized proteins may be generated through the binding measurements.

Next, the affinity reagents can be desorbed through a more stringent wash. This wash step may remove some or all affinity reagents from the immobilized substrates. In some cases affinity reagents may have been chosen to have low to moderate binding affinities to facilitate removal. Used affinity reagents may be re-captured for reuse or discarded. In examples where affinity reagents with cleavable detection moieties are used, the detection moieties may be cleaved and removed at this stage. Following stringent washing, in some examples, any remaining fluorescence can be quenched and even more stringent washing applied to remove leftover affinity reagent. Carry-over/contamination can be detected by reimaging the substrate before applying the next affinity reagent. Contamination may also be detected by monitoring consecutive for images for recurring signals. This concludes one cycle of analysis.

In some embodiments the fluorescently tagged affinity reagents may be quenched by exposure to prolonged intense light at the activation wavelength. Quenching of the fluorescent tags may replace washing steps to remove the affinity reagents. In some embodiments, it may be desirable to cycle n fluorophores to distinguish which signals were derived from the previous n−1 cycles.

Cycles continue for each affinity reagent, or multiplexing thereof. The result of the measurement phase is a very large table listing the binding coordinates for each affinity reagent, or the affinity reagents which bound at each coordinated location, see for example FIG. 10.

Analysis

The last step in protein identification may comprise a software tool to determine the most likely identity of each protein at each coordinate of the substrate from the information about which affinity reagents bound to that coordinate. The software may utilize information about the binding characteristics of each affinity reagent. For example, if a given affinity reagent preferentially binds to proteins containing the tri-peptide epitope AAA. Given the information about the binding characteristic of each affinity reagent, a database of the proteins in the sample, and list of binding coordinates, the pattern of binding, the software tool assigns a probable identity to each coordinate as well as a confidence for that identity. In the extreme case of precise 1-1 mappings between affinity reagents and proteins, this can be accomplished with a simple lookup table. However, in the case where binding is more complex, this may be performed via solving the appropriate satisfaction problem. In cases where the binding characteristics are highly complex, an expectation maximization approach may be employed.

The software could also utilize a listing of some or all locations in which each affinity reagent did not bind and use this information about the absence of epitopes to determine the protein present. The software could also utilize information about which affinity reagents did and did not bind to each address. Thus the software would use the information about both which epitopes were present and which epitopes were not present. The software may comprise a database. The database may contain sequences of some or all known proteins in the species from which the sample was obtained. For example if the sample is known to be of human origin then a database with the sequences of some or all human proteins may be used. If the species of the sample is unknown then a database of some or all protein sequences may be used. The database may also contain the sequences of some or all known protein variants and mutant proteins, and the sequences of some or all possible proteins that could result from DNA frameshift mutations. The database may also contain sequences of possible truncated proteins that may arise from premature stop codons, or from degradation.

The software may comprise one or more algorithms, such as a machine learning, deep learning, statistical learning, supervised learning, unsupervised learning, clustering, expectation maximization, maximum likelihood estimation, Bayesian inference, linear regression, logistic regression, binary classification, multinomial classification, or other pattern recognition algorithm. For example, the software may perform the one or more algorithms to analyze the information (e.g., as inputs of the one or more algorithm) of (i) the binding characteristic of each affinity reagent, (ii) the database of the proteins in the sample, (iii) the list of binding coordinates, and/or (iv) the pattern of binding of affinity reagents to proteins, in order to generate or assign (e.g., as outputs of the one or more algorithms) (a) a probable identity to each coordinate and/or (b) a confidence (e.g., confidence level and/or confidence interval) for that identity. Examples of machine learning algorithms may include support vector machines (SVMs), neural networks, convolutional neural networks (CNNs), deep neural networks, cascading neural networks, k-Nearest Neighbor (k-NN) classification, random forests (RFs), and other types of classification and regression trees (CARTs).

The software may be trained by performing the methods of this disclosure on a substrate where the identity of the protein at each address is predetermined. For example the software may be trained using a Nucleic Acid-Programmable Protein Array or epitope tiling array as a training dataset.

The raw data from the binding assays may comprise a series of images from which binding measurements of labeled affinity reagents to unknown proteins are derived. These binding measurements may then be used to infer the identity of proteins assayed. In some embodiments, these binding measurements may be used to infer the identity of each protein that is assayed. In some embodiments, these binding measurements may be used to provide characteristics related to the identity of proteins that are assayed. In some embodiments, protein inference may be determined based on three types of information: 1) binding measurements of affinity reagents to particular proteins, 2) a list of candidate protein sequences, and 3) information from which a semi-accurate prediction of the expected degree of binding for each affinity reagent to each candidate protein may be derived. Methods discussed herein provide statistical models of affinity reagents from which the probability of the affinity reagent binding any protein may be computed provided the primary sequence of a given protein. In some embodiments, statistical models may be trained using a series of binding measurements of the affinity reagent to each of a collection of proteins. These types of approaches may be used to predict measurements and/or characteristics of affinity reagent-to-protein binding when direct empirical measurements are not available. For example, these methods may be used when the number of proteins in a collection of proteins is such that determining empirical measurements would be time or cost prohibitive.

First, binding measurements may be acquired for the affinity reagent against a plurality of polypeptides or proteins. These binding measurements can be used to train a statistical model from which binding of the affinity reagent to any arbitrary protein may be predicted provided its primary sequence. Methods for acquiring such measurements include, but are not limited to, ELISA assays, flow cytometry assays, binding to protein arrays, binding to peptide arrays, and surface plasmon resonance assays. Protein binding may be modeled as a linear combination of the count of each of the J epitopes in the protein sequence and the fractional contribution of binding of the affinity reagent to that epitope to the protein-level binding measurement. This may be expressed as:

$$M_{Pr} = \sum_{t=1}^{t=J} c_{t,pr} \beta_t$$

Where:
$M_{pr}$=Binding measurement of affinity reagent to protein pr
$c_{t,pr}$=Count of epitope t in protein pr
$\beta_t$=Fractional binding contribution of affinity reagent to epitope t Measurements for an affinity reagent against multiple proteins form a linear system of equations:

$$\vec{M} = C\vec{\beta} + \varepsilon$$

Where:
$\vec{M}$ is a length N column vector containing the observed binding measurements for each protein
C is an N×J matrix of epitope counts with each column being counts for a particular epitope in each measured protein
$\vec{\beta}$ is a length J column vector of fractional binding of the reagent to each possible epitope ε is a scalar constant to correct for background binding or a noise floor It is trivial to extend the model to include non-standard amino acids or to model different types of epitopes (for example single residues, dimers, trimers, 4-mers, 5-mers). In the case of binding measurements to known proteins, $\vec{M}$ and C are known variables and values for $\vec{\beta}$ and E may be derived by linear regression or related approaches. In particular, non-negative least squares and non-negative least absolute shrinkage and selection operator (LASSO) regression may be well-suited for this problem. Non-negative least squares bounds the solution $\vec{\beta}$ to be non-negative, and non-negative LASSO regression further imposes a sparsity constraint. LASSO regression is particularly effective when the system is underdetermined, that is, when the number of unique proteins measured is less than the number of unique epitopes. Once $\vec{\beta}$ has been determined, binding measurement predictions can be made for any protein by counting each epitope in the sequence of the protein to generate values for c and evaluating the summation $\Sigma_{t=1}^{t=J} c_{t,pr}\beta_t$ to generate a binding affinity measurement prediction.

This is just one example of a way of modeling protein to affinity reagent binding. These data may be used to train any model that predicts protein binding affinity from either the primary sequence of a protein or a derivative of the primary sequence (e.g. amino acid composition, trimer count, predicted three dimensional structure). Another example could comprise using a non-linear model, for example with an exponential function relating trimer affinity to observed protein binding measurements or a multiplicative model where trimer-level affinities are multiplied to generate a protein level affinity. As another example, a neural network could be used to predict protein binding affinity from protein sequence or trimer composition. Additionally, a support vector regression model could be used to predict protein binding affinity from protein sequence or trimer composition.

Determining Characteristics of Sample

Once decoding is complete, the probable identities of the proteins conjugated to each address are defined. Consequently, their abundance in the mixture can be estimated by counting observations. Thus a listing of each protein present in the mixture, and the number of observances of that protein can be compiled.

Further, if a photo-cleavable linker, or other form of specifically cleavable linker, is used to attach the proteins to the substrate then specific proteins of interest may be released from the substrate and collected for further study.

For example specific proteins may be identified and eluted for further study. The methods of this disclosure may also serve as a way to purify and/or isolate a desired protein from a mixture. In some cases the method may be able to purify and/or isolate specific isotypes or post translationally modified proteins. In samples for which a complete list of possible proteins and associated sequences is not available this method may be able to distinguish different proteins of distinguish groups of proteins, these could then be eluted for further study. For example, for highly complex samples containing many unknown proteins, such as gut microbiome samples, the methods described herein may be used to fractionate the sample prior to mass spectrometry. In some cases proteins may be eluted from the substrate once their identities can be called. Removing the proteins from the substrate as they are identified allows subsequent rounds of affinity reagent binding to continue for the proteins whose identities cannot yet be called, and may decrease background noise and off target signals for the remaining rounds. In some examples one or more affinity reagents with specificity to particular proteins may be used as a first round to identify high abundance proteins such as serum albumin or immunoglobulins in a blood sample, these high abundance proteins may then be removed early in the process. In some cases a subset of the proteins on the substrate may be removed after every round of affinity reagent binding, or after every second, third, fourth, fifth, sixth, seventh, eighth, ninth, tenth, fifteenth, twentieth or more than twentieth round of affinity reagent binding. The signal to noise ratio may increase after each round of protein elution.

In some cases, unidentified proteins may be grouped or clustered based on their binding patterns. For example, in some cases, proteins present in the sample may not be represented in the sequence database. Unidentified proteins may be clustered into groups based on their binding patterns to the affinity probes with the goal of each group containing a set of unknown proteins in the sample with the same sequence. Protein quantities may be estimated for each group and included in quantitative analyses including, but not limited to, differential quantification between healthy and disease states, longitudinal analysis, or biomarker discovery. In some cases, an unidentified group may be selectively removed from the substrate for identification by mass spectrometry. In other cases, the unidentified group may be identified by performing further binding affinity measurement experiments specifically designed to generate confident identification.

In some cases after a protein or set of proteins have been removed it may be possible to add additional sample to the substrate. For example serum albumin is a high abundance protein in blood serum which may account for about half the protein in a sample, removing serum albumin after a first round of affinity reagent binding may allow the addition of further blood sample to the substrate. In some embodiments it may be preferred to remove high abundance proteins prior to immobilizing a sample on a substrate, for example through immunoprecipitation or affinity column purification.

Protein modifications may be identified using the methods of this disclosure. For example, post translational modifications may be identified by iterative cycles of detection using modification specific detection reagents interspersed with enzymatic processing (for example phosphatase treatment). Affinity reagents specific for different modifications may be used to determine the presence of absence of such modifications on the immobilized proteins. The method also allows quantification of the number of instances of each protein with and without a given modification.

Mutations in proteins may be detected by matching inconsistencies between the binding pattern of a sample protein and the predicted protein identity. For example an immobilized protein or polypeptide on the substrate which matches the affinity reagent binding profile of a known protein except for the binding of one affinity reagent may have an amino acid substitution. As affinity reagents may have overlapping epitopes an immobilized protein may have several mismatches from the predicted affinity binding pattern despite having a single amino acid substitution. DNA mutations which cause frameshifts of premature stop codons may also be detected.

The number of affinity reagents required may be less than the total number of epitopes present in the sample. For example if the affinity reagents are selected such that each affinity reagent recognizes one unique three peptide epitope then the total set of affinity reagents to recognize all possible epitopes in the sample is 20×20×20=8000. However the methods of the present disclosure may only require about 100, 200, 300, 400, 500, 600, 700, 800, 900, 1000, 1500, 2000, 2500, 3000, 3500, 4000, 4500, 5000, 5500 or 6000 of these affinity reagents. In some cases the methods may only require less than about 500, 1000, 2500, 3000, 3500, 4000, 4500, 5000, 5500 or 6000 affinity reagents. FIG. 13 shows the results of a simulation demonstrating the percentage of known human proteins that can be identified given a set of x affinity reagents specific to unique amino acid 3-mers as a function of the binding efficiency of each affinity reagent. As seen in FIG. 13, 98% of human proteins can be uniquely identified with 8000 3-mer affinity reagents, and a binding likelihood of 10%.

The methods of the present disclosure may be highly accurate. The methods of the present disclosure may be able to identify each protein with about 90%, 91%, 92%, 93%, 94%, 95%, 96%, 97%, 98%, 98.5%, 99%, 99.5% 99.9% or more than 99.9% accuracy.

The methods of the present disclosure may be able to predict the identity of each protein with about 90%, 91%, 92%, 93%, 94%, 95%, 96%, 97%, 98%, 98.5%, 99%, 99.5% 99.9% or more than 99.9% confidence. The degree of confidence may be different for different proteins within the sample. For example proteins with very unique sequences may be identified with higher confidence than proteins which are highly similar to other proteins. In some cases a protein may be identified as part of a family of proteins with high confidence, however the exact identity of the protein may be predicted with lower confidence. In some cases proteins that are extremely large or extremely small may be predicted with lower confidence than proteins of more moderate size.

In some cases a protein may be identified as part of a family of proteins with high confidence, however the exact identity of the protein may be predicted with lower confidence. For example, a protein containing a single amino acid variant may be difficult to resolve from the canonical form of the protein with high confidence. In this case, neither the canonical sequence nor the single amino acid variant-containing form may have high confidence, but a high confidence can be assessed to the unknown protein being part of the group of proteins containing both sequences. A similar case may occur in instances where a protein may have multiple related isoforms with similar sequence.

The methods of the present disclosure may be able to identify some or all proteins in a given sample. The methods of the present disclosure may be able to identify about 90%, 91%, 92%, 93%, 94%, 95%, 96%, 97%, 98%, 98.5%, 99%, 99.5% 99.9% or more than 99.9% of proteins in a sample.

The methods of the present disclosure may be able to rapidly identify proteins in a sample. The methods of the present disclosure may be able to identify more than about 100, about 1000, about 5000, about 10000, about 20,000, about 30,000, about 40,000, about 50,000, about 100,000, 1,000,000, about 10,000,000, about 100,000,000, about 1,000,000,000, about 10,000,000,000, about 100,000,000,000, about 1,000,000,000,000 proteins per flow cell per day. The methods of the present disclosure may be able to identify more than about $10^{10}$, $10^{11}$, $10^{12}$, $10^{13}$, $10^{14}$, $10^{15}$, $10^{16}$, $10^{17}$, or more than about $10^{17}$ proteins per flow cell per day. The methods of the present disclosure may be able to identify about $10^{10}$-$10^{12}$, $10^{11}$-$10^{14}$, $10^{12}$-$10^{16}$, or $10^{13}$-$10^{17}$ proteins per flow cell per day. The methods of the present disclosure may be able to identify more than 95% of the proteins within about 10 pg, about 20 pg, about 30 pg, about 40 pg, about 50 pg, about 60 pg, about 70 pg, about 80 pg, about 90 pg, about 100 pg, about 300 pg, about 300 pg, about 400 pg, about 500 pg, about 600 pg, about 700 pg, about 800 pg, about 900 pg, about 1 ng, about 2 ng, about 3 ng, about 4 ng, about 5 ng, about 6 ng, about 7 ng, about 8 ng, about 8 ng, about 10 ng, about 10 ng, about 20 ng, about 30 ng, about 40 ng, about 50 ng, about 60 ng, about 70 ng, about 80 ng, about 90 ng, about 100 ng, about 300 ng, about 300 ng, about 400 ng, about 500 ng, about 600 ng, about 700 ng, about 800 ng, about 900 ng, about 1 µg, about 2 µg, about 3 µg, about 4 µg, about 5 µg, about 6 µg, about 7 µg, about 8 µg, about 8 µg, about 10 µg, about 10 µg, about 20 µg, about 30 µg, about 40 µg, about 50 µg, about 60 µg, about 70 µg, about 80 µg, about 90 µg, about 100 µg, about 300 µg, about 300 µg, about 400 µg, about 500 µg, about 600 µg, about 700 µg, about 800 µg, about 900 µg, or more than about 1 mg of protein per flow cell per day.

The methods of the present disclosure may be used to assess the proteome after an experimental treatment. The methods of the present disclosure may be used to assess the effect of a therapeutic intervention.

The methods of the present disclosure may be used for biomarker discovery. Monitoring proteome expression in subjects with and without disease may identify biomarkers. Monitoring proteome expression in subjects prior to developing diseases, or in subjects at risk of developing diseases may identify biomarkers that predict risk. Evaluating the proteome expression of a subject may indicate the health of the subject or the risk of developing certain diseases or disorders. The methods of this disclosure may be used to evaluate therapies, or differentiate drug/therapy responders from non-responders. The methods of this disclosure may be of particular use for personalized medicine.

The methods of the present disclosure may be used to diagnose disease. Different diseases or disease stages may be associated with different panels of protein expression. Different panels of protein expression may be associated with different treatment outcomes for each given treatment. A subject's proteome expression data may be used to diagnose the subject and/or select the most appropriate therapy.

The methods of the present disclosure may be used to identify the individual or species a sample come from. For example the methods of the present disclosure could be used to determine if a sample is actually from the claimed species or source. The methods described herein may have an advantage over PCR based methods in samples with abundant protein but limited nucleic acid. For example, the methods of the present disclosure may be useful for identifying the origins of honey samples. For further examples, the methods of the present disclosure could be used to assess food safety and food quality control.

The methods of the present disclosure may be used to identify any single protein molecule from a pool of protein molecules using less affinity reagents than the number of possible proteins. For example the methods may identify, with certainty above a threshold amount, an unidentified single protein molecule from a pool of n possible proteins, using a panel of affinity reagents, wherein the number of affinity reagents in the panel is m, and wherein m is less than n. The unidentified protein may be a known protein which corresponds to known protein and gene sequences, or may be an unknown protein without known protein or gene sequences. In the case of an unknown protein this method may identify a signature of the unknown protein, and thus the presence and quantity of the unknown protein, but not the amino acid sequence. The methods of the present disclosure may be used to select a panel of m affinity reagents capable of identifying an unidentified protein selected from a pool of n possible proteins. The methods disclosed herein are also capable of uniquely identifying and quantifying n proteins in a mixture of proteins using m binding reagents, and wherein each protein is identified via a unique profile of binding by a subset of the m the binding reagents. Further, m may be less than about a half, a third, a fourth, a fifth, a sixth, a seventh, a tenth, a twentieth, a fiftieth or a hundredth of n. For further example the present disclosure may be used to select a panel of less than about 100, 200, 300, 400, 500, 600, 700, 800, 900, 1000, 1500, 2000, 2500, 3000, 3500, or 4000 affinity reagents, such that the panel of affinity reagents is capable of uniquely identifying each of at least about 100, 500, 1000, 2000, 3000, 4000, 5000, 6000, 7000, 8000, 9000, 10,000, 12,000, 14,000, 16,000, 18,000, 20,000, 25,000, 30,000, 35,000, 40,000, 50,000, 100,000, 200,000, 300,000, 400,000, 500,000, 600,000, 700,000, 800,000, 900,000, 1,000,000, 2,000,000, 3,000,000, 4,000,000, or 5,000,000 different proteins.

The methods of the present disclosure may be capable of identifying most of the proteins in a proteome. The methods of the present disclosure may be capable of identifying most of the proteins in a mammalian, bird, fish, amphibian, reptilian, vertebrate, invertebrate, plant, fungal, bacterial or archaeal proteome. The methods of the present disclosure may be capable of identifying more than about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% of the proteins in a proteome.

EXAMPLES

Example 1

Protein Identification Using Antibodies that Bind Unique 3-mer Peptides

A computational experiment was performed to determine the relationship between the percentage coverage of the set of all epitopes in a proteome and the percentage of the proteome that may be identified using the methods of this disclosure. For this experiment the set of all 3-mer amino acid epitopes was selected. Protein modifications were not considered. As there are 20 naturally occurring amino acids the total set of all 3-mer epitopes is 20×20×20=8000 possible epitopes. For the simulation x was set as the number of epitopes screened in an experiment, for each value of x from 1 to 8000 a set of x epitopes were randomly selected and the percentage of the proteome which could be identified was calculated. FIG. 13 shows the results of this simulation.

Example 2

Protein Identification Using Antibodies that Bind Unique 3-mer Peptides

A further computational experiment was performed to determine the impact of the number of affinity reagents on identifiability and coverage. Data series were calculated for a range of affinity reagent pool sizes to show the percentage of the proteome which may be identified (y axis) for each possible coverage of a protein and the results are shown in Table 1. For example, a protein with 100 amino acids has 98 3-mer amino acid epitopes "landing sites", if 20% of these 3-mer amino acid epitopes are bound that may or may not be sufficient to identify the protein. As shown in FIG. 15, with an affinity reagent pool of 250 3-mer specific affinity reagents if 20% of the landing sites of each protein are bound, then only about 7% of the proteome may be identified. For an affinity reagent pool of 8000 affinity reagents then with 20% of landing sites bound about 98% of the proteome may be identified.

indicating complete denaturation of the Green Fluorescent Protein. The protein was then incubated with an anti-peptide antibody with an attached Alexa-Fluor 647. The anti-peptide antibody was then rinsed with 0.1% Tween-20. This was then imaged using TIRF on a Nikon Eclipse Ti with an Andor NEO sCMOS camera. FIG. 17 shows a resulting image captured (colors reversed for clarity).

Example 4

Identification of a Protein

A proteome of four possible proteins, Green Fluorescent Protein, RNASE1, LTF, and GSTM1, is depicted in FIG. 18. In this example, a single molecule of an unknown protein from this proteome is conjugated to a position on a substrate. The unknown protein is sequentially interrogated by a panel of nine different affinity reagents. Each of the nine different affinity reagents recognize a different amino acid trimer [AAA, AAC, AAD, AEV, GDG, QSA, LAD, TRK, DGD], and each is labeled with a fluorescent dye. It is determined that the unknown protein is bound by the affinity reagents DGD, AEV, LAD, GDG, and QSA. Analysis of the sequences of the four proteins of this proteome indicates that

TABLE 1

Impact of number of 3-mer d-code probes on identifiability vs coverage of proteome

| | 8000 | 7000 | 6000 | 5000 | 4000 | 3000 | 2000 | 1000 | 500 | 250 |
|---|---|---|---|---|---|---|---|---|---|---|
| 1.00% | 0.1825 | 0.135 | 0.0845 | 0.072 | 0.042 | 0.0125 | 0.0035 | 0 | 0 | 0 |
| 2.00% | 0.492 | 0.41 | 0.3515 | 0.26 | 0.156 | 0.0985 | 0.037 | 0.0035 | 0.0005 | 0 |
| 3.00% | 0.677 | 0.614 | 0.55 | 0.455 | 0.344 | 0.2175 | 0.0985 | 0.015 | 0.0005 | 0 |
| 4.00% | 0.786 | 0.745 | 0.676 | 0.604 | 0.472 | 0.334 | 0.176 | 0.029 | 0.003 | 0 |
| 5.00% | 0.843 | 0.811 | 0.765 | 0.7005 | 0.61 | 0.4765 | 0.269 | 0.054 | 0.0075 | 0 |
| 6.00% | 0.9025 | 0.852 | 0.809 | 0.7645 | 0.6815 | 0.569 | 0.3485 | 0.092 | 0.012 | 0.0015 |
| 7.00% | 0.9005 | 0.877 | 0.8435 | 0.81 | 0.7285 | 0.626 | 0.4345 | 0.1395 | 0.022 | 0.0025 |
| 8.00% | 0.9275 | 0.9025 | 0.8875 | 0.835 | 0.782 | 0.678 | 0.491 | 0.192 | 0.034 | 0.002 |
| 9.00% | 0.9415 | 0.923 | 0.898 | 0.8725 | 0.814 | 0.728 | 0.5495 | 0.221 | 0.0415 | 0.0065 |
| 10.00% | 0.9575 | 0.941 | 0.919 | 0.8835 | 0.8535 | 0.751 | 0.601 | 0.261 | 0.0715 | 0.007 |
| 12.00% | 0.9635 | 0.957 | 0.946 | 0.913 | 0.8825 | 0.81 | 0.663 | 0.3445 | 0.0955 | 0.0145 |
| 15.00% | 0.978 | 0.969 | 0.962 | 0.9505 | 0.9185 | 0.8605 | 0.7675 | 0.443 | 0.1585 | 0.0295 |
| 17.00% | 0.981 | 0.9765 | 0.9645 | 0.9575 | 0.927 | 0.884 | 0.8005 | 0.503 | 0.1915 | 0.0435 |
| 20.00% | 0.9885 | 0.986 | 0.9725 | 0.9635 | 0.9575 | 0.9105 | 0.847 | 0.584 | 0.2525 | 0.0775 |
| 25.00% | 0.99 | 0.9865 | 0.9785 | 0.9745 | 0.966 | 0.9445 | 0.8915 | 0.6955 | 0.357 | 0.1165 |
| 30.00% | 0.9865 | 0.9895 | 0.985 | 0.9825 | 0.973 | 0.9625 | 0.9245 | 0.76 | 0.4355 | 0.1665 |
| 50.00% | 0.9915 | 0.9915 | 0.9935 | 0.9895 | 0.9855 | 0.978 | 0.967 | 0.89 | 0.691 | 0.374 |

Example 3

Illuminated Protein Molecules Conjugated on a Substrate

A fluorescent protein sample, Phycoerythrin, was directly conjugated to an NHS-Ester coated coverslip for 4 hours in an incubation chamber at 4 degrees. The fluorescent protein sample was then imaged on a Leica DMi8 with a Hamamatsu orca flash 4.0 camera using 300 ms exposure. FIGS. 16A and 16B show a resulting image captured (colors reversed for clarity). As seen in FIGS. 16A and 16B, each dark spot represents an area of fluorescence signal indicating the presence of a protein. FIG. 16B is a blow-up of FIG. 16A. Arrows in FIG. 16B indicate signals representing proteins that are clearly distinguishable from background noise.

A second protein sample, Green Fluorescent Protein, was denatured and directly conjugated to an NHS-Ester coated coverslip for 4 hours in an incubation chamber at 4 degrees. Initial imaging showed no baseline residual fluorescence, only GFP contains all five of these three amino acid motifs, these motifs are underlined in the sequence of FIG. 18. Thus, it is determined that the single molecule of the unknown protein is a GFP protein.

Example 5

Implementation Example

Considered in this example are binding measurements of an affinity reagent to a nucleic acid programmable protein array (NAPPA) containing 720 unique proteins with 3-5 replicates each included on the array. In some embodiments, these replicates may be scattered across the array. Binding is assessed by hybridizing a fluorescently-labelled affinity reagent to the array and measuring observed fluorescence at each spot on the array. In this example, the identity of each protein at each spot is known. Accordingly, fluorescence may be mapped to protein identities.

In this example, the protein binding measurement (fluorescence) is modeled as a linear combination of the count of each of the 8000 possible trimers in the protein sequence and the fractional contribution to observed fluorescence attributable to binding of the affinity reagent to that trimer. That is:

$$F_{pr} = \sum_{t=1}^{t=8000} c_{t,pr} \beta_t$$

Where:
F$_{pr}$=Fluorescence for protein pr
c$_{t,pr}$=Count of trimer t in protein pr
β$_t$=Fractional fluoresence from binding of affinity reagent to trimer t Measurements for an affinity reagent against multiple proteins form a linear system of equations:

$$\vec{F} = C\vec{\beta} + \varepsilon$$

Where:
$\vec{F}$ is a length N column vector containing the observed fluorescence for each protein
C is an N×8000 matrix of trimer counts with each column being counts for a particular trimer in each measured protein
$\vec{\beta}$ is a length 8000 column vector of fractional fluorescence for each possible trimer
ε is a scalar constant to correct for background binding or a noise floor The model described herein may be extended to include non-standard amino acids or model n-mers of different lengths. In the case of known NAPPA or similar binding measurements, $\vec{F}$ and C are known variables and values for $\vec{\beta}$ and ε may be derived by linear regression or related approaches. In particular, non-negative least squares and non-negative least absolute shrinkage and selection operator (LASSO) regression may be well-suited for this problem. Non-negative least squares bounds the solution $\vec{\beta}$ to be non-negative, and non-negative LASSO regression further imposes a sparsity constraint. LASSO regression may be particularly effective when the system is underdetermined, that is, when the number of unique proteins measured is less than the number of unique trimers (8,000 in this example).

Binding to the aforementioned NAPPA array was simulated for an affinity reagent with the following relative affinities:
LAS: 0.75
GEL: 0.05
YIC: 0.001
STK: 0.001
Binding to all other trimers was assigned affinity 0.00001.

Binding to each protein on the NAPPA array was simulated by calculating the expected binding using the described statistical model and aforementioned binding affinities with Gaussian noise applied having a standard deviation of 5% of the expected binding affinity.

From these simulated data, LASSO was used (with the LASSO sparsity parameter α set to 1e-3) to learn the binding affinities of the reagent from the protein binding measurements. The learned affinities were:
LAS 0.750034
GEL 0.040796
ASW 0.012120
SGD 0.005001
QPH 0.003975
LGC 0.003788
KGR 0.002475
VPS 0.002416
EIK 0.002305
SES 0.002149
RIS 0.001235
SSE 0.001067
STS 0.000953
APP 0.000889
HSD 0.000785
KSQ 0.000735
VQK 0.000637
PPT 0.000538
GCS 0.000417
RPR 0.000106
QPQ 0.000051
ACS 0.000026
With all other trimers having an affinity of zero.

This example indicates that the approach is able to build a reasonable estimate of affinity reagent binding albeit with a tolerable amount of noise.

Example 6

Selection of KW Affinity Reagent

Figure 6:
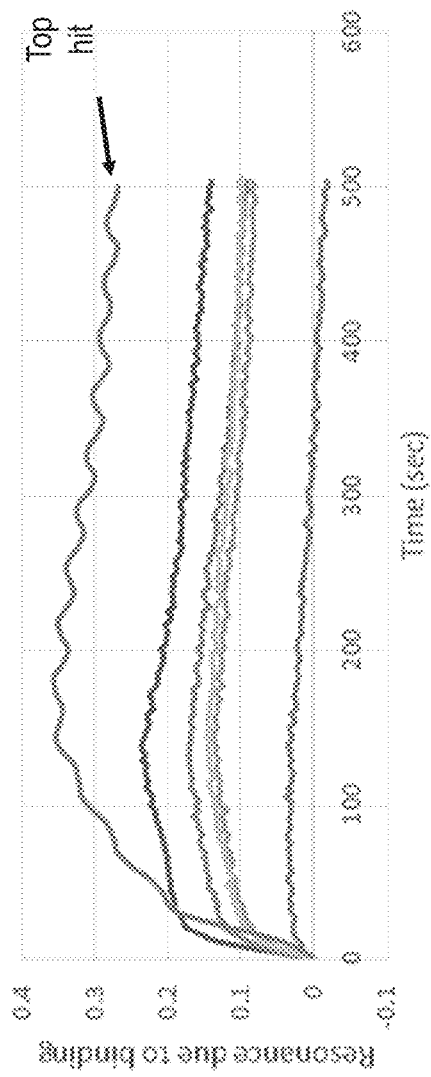
FIG. 6 illustrates target binding of several aptamers identified in an aptamer selection screen, in accordance with some embodiments.
Figure 7:
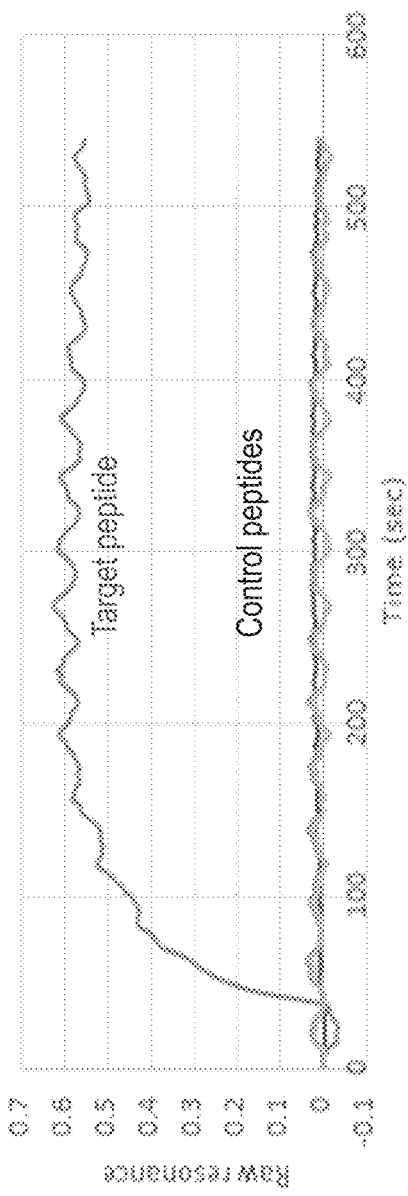
FIG. 7 illustrates preliminary characterization of an identified aptamer, in accordance with some embodiments.

An affinity reagent selection screen was conducted to select aptamers which bound to any of four different target epitopes—KW, LFQ, IRN, and EGE. Array-based surface plasmon resonance imaging selection was used to select aptamers which bound the targets from an aptamer library. Preliminary validation was conducted on aptamers which bound to the target KW. FIG. 6 shows binding of the 5 top hits to the KW target as measured by surface plasmon resonance. FIG. 7 shows binding of the best antiKW aptamer compared to negative control peptides.

Figure 8:
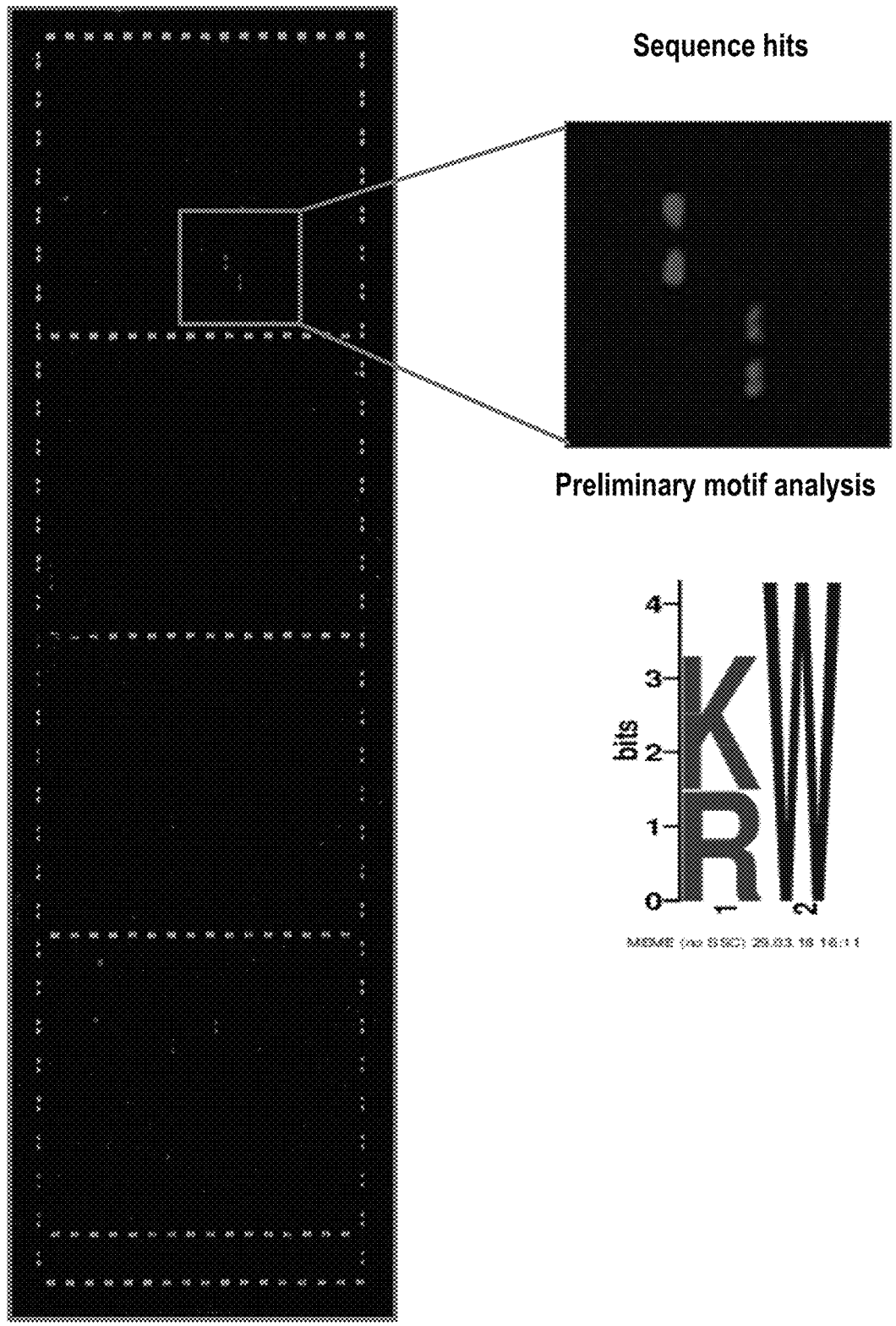
FIG. 8 illustrates preliminary characterization of an identified aptamer, in accordance with some embodiments.

To determine the epitope specificity of the top anti KW aptamer from FIG. 6 the aptamer was fluorescently labeled and applied to a peptide array. Based on the binding of the labeled aptamer to the peptide array the epitopes recognized by the aptamer were determined to be KW and KR with relatively similar affinity for both. The binding data and preliminary motif analysis are shown in FIG. 8.

Example 7

High-Throughput Sequencing Fluorescent Ligand Interaction Profiling

Figure 10:
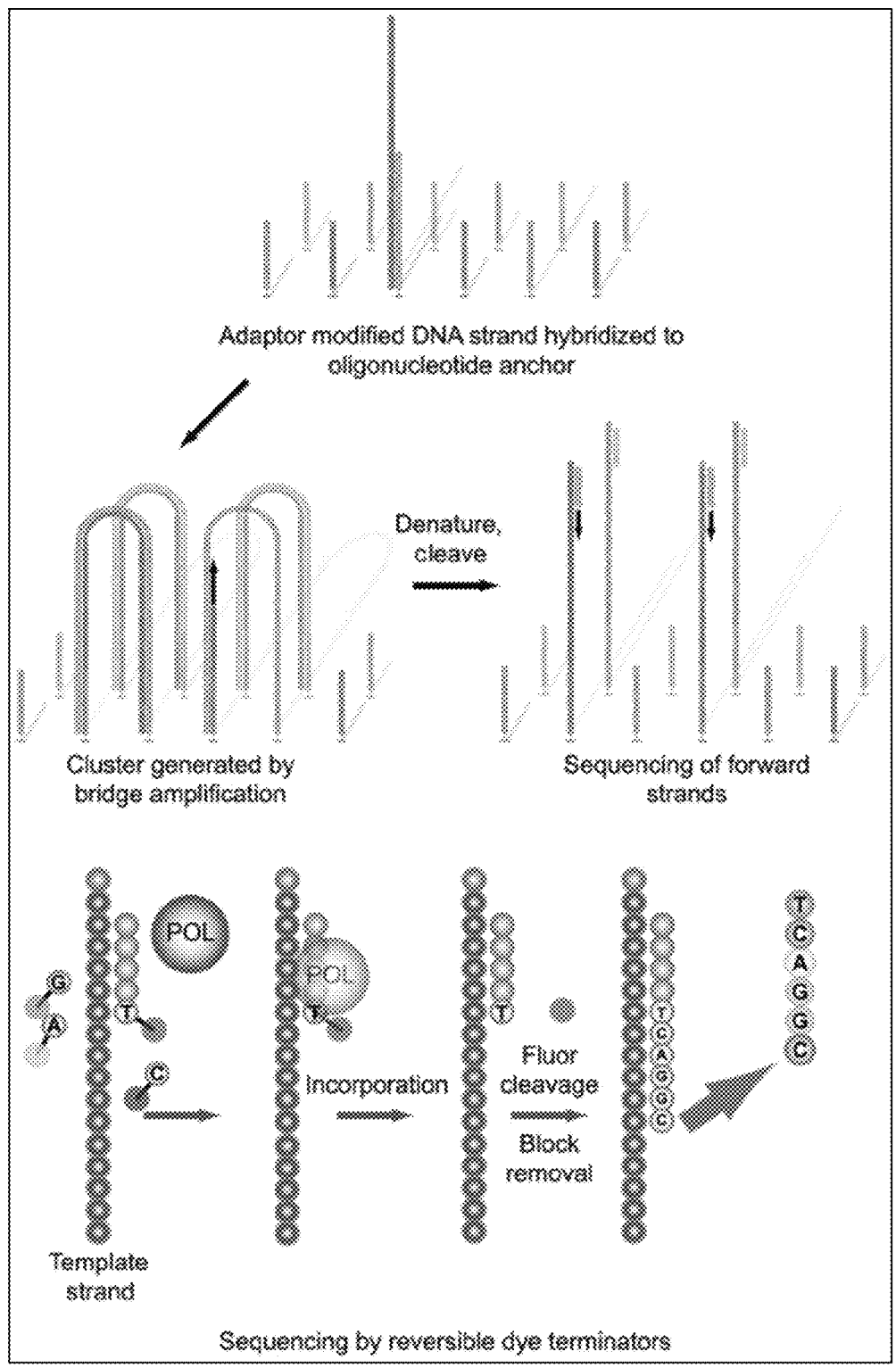
FIG. 10 illustrates an example of cluster amplification, in accordance with some embodiments.
Figure 11:
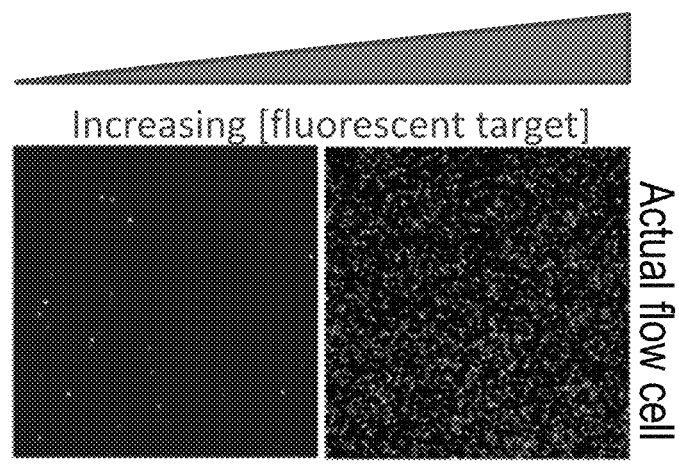
FIG. 11 illustrates binding of a fluorescently labeled peptide target to aptamer clusters on a flow cell, in accordance with some embodiments.
Figure 12:
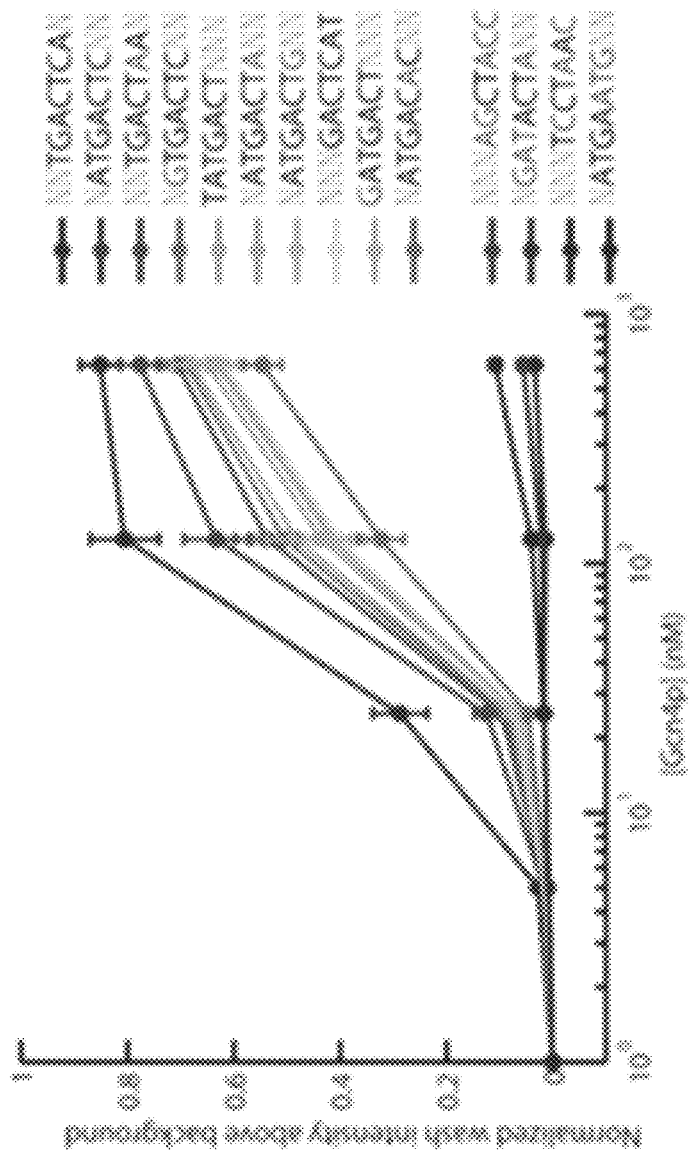
FIG. 12 illustrates binding affinities of several aptamers (SEQ ID NOS 18-31, respectively, in order of appearance) for a peptide target, in accordance with some embodiments.

A high-throughput sequencing fluorescent ligand interaction profiling assay was conducted by obtaining an aptamer library, and incorporating adapters sequences on both ends of the aptamers of the library. The library of aptamers with adapters was applied to flow cell comprising immobilized oligo primers and cluster amplification was conducted as depicted in FIG. 10. After cluster amplification the clusters (each representing a single aptamer from the aptamer library) were sequenced using reversible dye terminators. The clusters were then denatured to remove the sequencing reagents, washed, and were allowed to fold into their native aptamer conformations. A fluorescently labeled peptide target was applied to the clusters at four different concentrations, and was imaged to show the clusters which bound the fluorescently labeled peptide target. FIG. 11 shows representative images of the flow cell with bound fluorescently labeled peptide target and two different concentrations. The fluorescence data was combined with the sequencing data to provide affinity measurements for each aptamer of the aptamer library represented on the flow cell. FIG. 12 shows sequences and binding affinities of several different aptamers for the fluorescently labeled peptide target (LFQ).

Example 8

Peptide Synthesis and Validation

Materials:
All reagents and solvents were of peptide synthesis grade or highest purity available. Amino acid derivatives were obtained from Aapptech, (Louisville, KY USA) and all solvents for peptide synthesis, SPE and RP±HPLC were obtained from Acros Organics, USA.

Peptide Synthesis:
Peptides were synthesized on MultiPep RSi synthesizer (Intavis, Germany) employing standard Fmoc/tBu chemistry. Amino acid derivatives were activated by N,N,N',N'-Tetramethyl-O-(1H-benzotriazol-1-yl)uronium hexafluorophosphate (HBTU) (0.5M). The standard synthesis protocol employed in the 96-vessel microreaction block to synthesize peptide. Rink Amide Resin (Intavis, Germany) was loaded at 0.53 mmol/g of amine content to 2 micromol per vessel. Following addition sequence was used to synthesize peptides:

| Resin Preparation | | |
|---|---|---|
| 1 | Memo | synthesis scale: 2 μmol |
| 1 | RinseNeedle | 1500/2000 μl (DMF) |
| 2 | Pipet | 1500 μl/1500 μl CapMixture (Acetic Anhydride) -> Drain |
| 3 | RinseNeedle | 1500/2000 μl (DMF) |
| 4 | Pipet | 1500 μl /1500 μl N-methylpiperidine solution -> Drain |
| 5 | RinseNeedle | 1000/2000 μl (DMF) |
| 6 | PrimeManifold | 10000 μl, DMF |
| 7 | WashResin | 1200 μl, DMF, 4x |
| 8 | Extract | 60 s |
| Cycle | | 1. -> N. (count = N) (N – number of couplings) |
| 9 | Deprotection | 50 μl, N-methylpiperidine |
| 10 | Deprotection | 50 μl, N-methylpiperidine |
| 11 | RinseNeedle | 1000/2000 μl |
| 12 | WashResin | 1800 μl, DMF, 2x |
| 13 | WashResin | 1200 μl, DMF, 8x |
| 14 | Extract | 30 s |
| 15 | Coupling | 20 μl HBTU + 5 μl NMM + 2 μl NMP + 21 μl Amino-acid derivative |
| 16 | Coupling | 20 μl HBTU + 5 μl NMM + 2 μl NMP + 21 μl Amino-acid derivative |
| 17 | Capping | 50 μl, CapMixture (Acetic Anhydride) |
| 18 | RinseNeedle | 1000/2000 μl (DMF) |
| 19 | WashResin | 1200 μl, DMF, 6x |
| 20 | Extract | 60 s |
| Final Action | | |
| 21 | Deprotection | 80 μl, N-methylpiperidine |
| 22 | Deprotection | 80 μl, N-methylpiperidine |
| 23 | Deprotection | 80 μl, N-methylpiperidine |
| 24 | RinseNeedle | 500/2500 μl (DMF) |
| 25 | WashResin | 1800 μl, DMF, 2x |
| 26 | WashResin | 1200 μl, DMF, 8x |
| 27 | PrimeManifold | 10000 μl, Ethanol |
| 28 | WashResin | 1200 μl, Ethanol, 2x |
| 29 | Extract | 300 s |
| 30 | RinseNeedle | 1000/3000 μl (DMF) |

All amino-acid derivatives were used as 0.5M solutions in DMF, except of Fmoc-Lysine (Biotin) (0.3M).
N-methylpiperidine was used as 2M solution in DMF, Acetic anhydride was used as 5% solution in DMF (0.529M). Coupling continued for 30 min for each cycle and repeated 2 times for each building block. Amino-acid was used in 10× excess over amine to ensure complete coupling. Peptides were cleaved with a solution of 5% water, 2.5% Triisopropylsilane in trifluoroacetic acid (TFA) at room temperature for 2 h, precipitated with tret-butyl methylether at −20 C and washed three times with cold tret-butyl methylether (200 ul). The dried peptides were dissolved in 1 mL of 0.1% aqueous TFA (500 microliters) and stored at −20 C.

Solid-Phase Extraction
The crude peptides were purified on a Sep-Pak C18 Multi 96-well plate (WAT054955) containing 40 mg of C18 sorbents in each well using the Multi 96 vacuum manifold (Waters, USA). The eluates were collected in 2 mL collection racks (WAT058956). In a typical protocol, the cartridge or plate was washed with 1 ml of MeOH, and conditioned with 0.1% aqueous TFA before loading the peptide sample. Peptides were loaded by passing the solution slowly through the stationary phase without vacuum to accomplish near quantitative peptide binding. The solid phase was washed with 0.1% aqueous TFA to remove salts and other polar impurities, before the bound peptides were eluted with 1 mL of 70% aqueous acetonitrile. Solvent was evaporated using Centrivap overnight and pellet was re-dissolved in 500 microliters of DI water. Concentration was measured using Tecan Spark plate reader using water as blank and collecting absorption spectra in the range of 200 to 1000 nm. Absorption and extinction coefficient at 214 nm was used to calculate concentration of peptide. UV transparent 96-well plates (ThermoFisher 8404) were used to measure the concentration of peptides.

Figure 9:
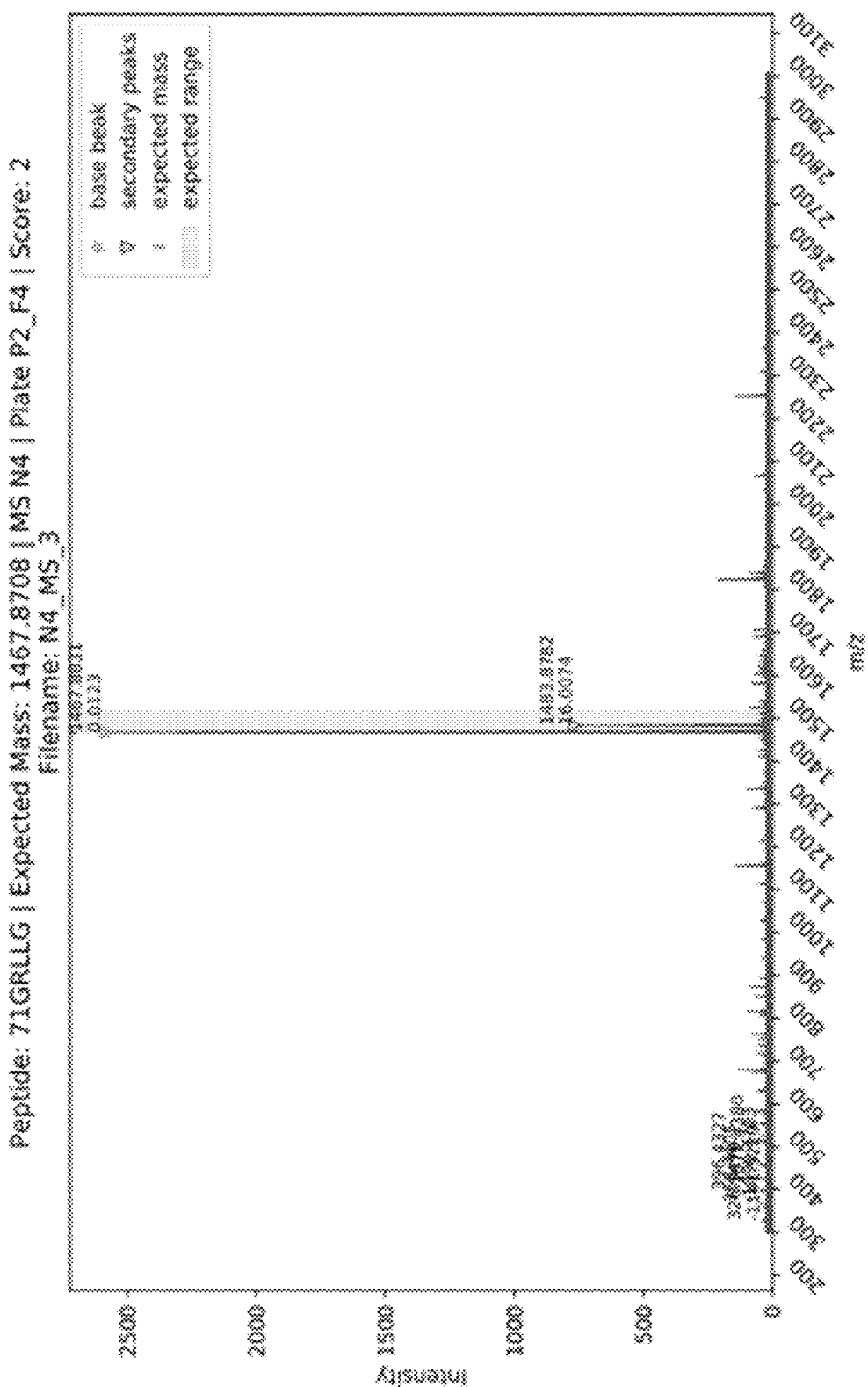
FIG. 9 illustrates Mass Spectrometry verification of a synthesized peptide (SEQ ID NO: 17), in accordance with some embodiments.

Mass-Spectrometry:
Matrix solution was purchased from Agilent Technologies (Cat # G2037A). Samples were prepared by co-spotting 1 microliter of peptide stock solution and 1 microliter of matrix on the MALDI sample plate and letting the sample dry under ambient conditions. Mass spectra were recorded on a MALDI-TOF mass-spectrometer AB SCIEX 5800 TOF/TOF. A representative Mass spectra is shown in FIG. 9.

Computer Control Systems
The present disclosure provides computer control systems that are programmed to implement methods of the disclosure. FIG. 14 shows a computer system 1401 that is programmed or otherwise configured to characterize and identify biopolymers, such as proteins. The computer system 1401 can regulate various aspects of assessing and analyzing samples of the present disclosure, such as, for example, observing signals at unique spatial addresses of a substrate; determining a presence of an identifiable tag linked to a biopolymer portion at unique spatial addresses based on observed signals; assessing the determined identifiable tags against a database of biopolymer sequences to determine characteristics of biopolymer portions. The computer system 1401 can be an electronic device of a user or a computer system that is remotely located with respect to the electronic device. The electronic device can be a mobile electronic device.

The computer system 1401 includes a central processing unit (CPU, also "processor" and "computer processor" herein) 1405, which can be a single core or multi core processor, or a plurality of processors for parallel processing. The computer system 1401 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The computer system 1401 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the computer system 1401, can implement a peer-to-peer network, which may enable devices coupled to the computer system 1401 to behave as a client or a server.

The CPU 1405 can execute a sequence of machine-readable instructions, which can be embodied in a program or software. The instructions may be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and writeback.

The CPU 1405 can be part of a circuit, such as an integrated circuit. One or more other components of the system 1401 can be included in the circuit. In some cases, the circuit is an application specific integrated circuit (ASIC).

The storage unit 1415 can store files, such as drivers, libraries and saved programs. The storage unit 1415 can store user data, e.g., user preferences and user programs. The computer system 1401 in some cases can include one or more additional data storage units that are external to the computer system 1401, such as located on a remote server that is in communication with the computer system 1401 through an intranet or the Internet.

The computer system 1401 can communicate with one or more remote computer systems through the network 1430. For instance, the computer system 1401 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1401 via the network 1430.

Methods as described herein can be implemented by way of machine (e.g., computer processor) executable code stored on an electronic storage location of the computer system 1401, such as, for example, on the memory 1410 or electronic storage unit 1415. The machine executable or machine readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1401 can include or be in communication with an electronic display 1435 that comprises a user interface (UI) 1440. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1405. The algorithm can, for example, determine characteristics and/or identities of biopolymer portions, such as protein portions. For example, algorithms may be used to determine a most likely identity of a candidate biopolymer portion, such as a candidate protein portion.

In some embodiments aptamers or peptamers which recognize short epitopes present in many different proteins may be referred to as digital aptamers or digital peptamers. An aspect of the invention provides a set of digital aptamers or digital peptamers, wherein the set comprises at least about 15 digital aptamers or digital peptamers, wherein each of the 15 digital aptamers or digital peptamers has been characterized to bind specifically to a different epitope consisting of 3 or 4 or 5 consecutive amino acids, and wherein each digital aptamer or digital peptamer recognizes a plurality of distinct and different proteins that comprise the same epitope to which the digital aptamer or digital peptamer binds. In some embodiments the set of digital aptamers or digital peptamers comprises 100 digital aptamers or digital peptamers that bind epitopes consisting of 3 consecutive amino acids. In some embodiments the set of digital aptamers or digital peptamers further comprises 100 digital aptamers that bind epitopes consisting of 4 consecutive amino acids. In some embodiments the set of digital aptamers or digital peptamers further comprises 100 digital aptamers or digital peptamers that bind epitopes consisting of 5 consecutive amino acids. In some cases, digital affinity reagents may be an antibody, aptamer, peptamer, peptide or Fab fragment.

In some embodiments the set of digital aptamers comprises at least about 20, 30, 40, 50, 60, 70, 80, 90, 100, 200, 300, 400, 500, 600, 700 800, 900, or 1000 digital aptamers. In some embodiments the set of digital aptamers comprises at least 1000 digital aptamers that bind epitopes consisting of 4 consecutive amino acids. In some embodiments the set of digital aptamers further comprises at least 100 digital aptamers that bind epitopes consisting of 5 consecutive amino acids. The set of digital aptamers further comprises at least 100 digital aptamers that bind epitopes consisting of 3 consecutive amino acids. In some embodiments the set of digital aptamers are immobilized on a surface. In some embodiments the surface is an array.

In another aspect the invention provides a method for generating a protein binding profile of a sample comprising a plurality of different proteins, said method comprising: contacting said sample with a set of digital aptamers, under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; optionally removing an unbound protein; and detecting binding of protein to said digital aptamers, whereby a protein binding profile of the sample is generated.

In some embodiments the method further comprises the step of treating the sample with a protein cleaving agent prior to step (a) of contacting the sample with the set of digital aptamers under conditions that permit binding.

In another aspect the invention comprises a library of protein binding profiles for two or more different samples each of which comprises a plurality of proteins, said method comprising: contacting a sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; optionally removing an unbound protein; generating a protein binding profile of the sample being tested by detecting binding of protein to the digital aptamers, whereby a protein binding profile is generated; and repeating the steps above with at least two samples.

In some embodiments the method further comprises the step of treating the sample with a protein cleaving agent prior to the step of contacting the sample with the set of digital aptamers under conditions that permit binding.

In another aspect the invention comprises a method for characterizing a test sample, comprising: contacting the test sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; optionally removing an unbound protein generating a protein binding profile of said test sample by detecting binding of protein to the digital aptamers; and comparing the generated protein binding profile of the test sample with a protein binding profile of a reference sample to characterize the test sample.

In another aspect the invention comprises a method for determining presence or absence of a bacteria, virus, or cell in a test sample, said method comprising: contacting the test sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; optionally removing an unbound protein; generating a protein binding profile of the test sample by detecting binding of protein to the digital aptamers, whereby a protein binding profile is generated; and comparing the protein binding profile of the test sample with a protein binding profile of a reference sample, whereby presence or absence of the bacteria, virus or cell in the test sample is determined by the comparison.

In another aspect the invention comprises a method for identifying a test protein in a sample, said method comprising: contacting a sample comprising or suspected of comprising the test protein with a set of digital aptamers that comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; and determining the identity of the test protein by detecting of binding of the test protein to the set of digital aptamers, wherein at least about six digital aptamers bind the test protein; and wherein presence of binding indicates presence of at least about six epitopes in the test protein, wherein the identity of the at least about six epitopes is used to identify the test protein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for selecting an affinity reagent which binds a desired peptide epitope in a plurality of sequence contexts, the method comprising:
   obtaining a peptide library comprising a plurality of at least 400 sequence contexts, each peptide of the peptide library comprising the sequence αXβ, wherein X is the desired peptide epitope, wherein X is a sequence of 2, 3 or 4 amino acids, wherein each of α and β comprises at least one amino acid, and wherein each of α and β varies amongst the plurality of sequence contexts within the peptide library; and
   screening one or more affinity reagents against the peptide library to select an affinity reagent from among the one or more affinity reagents which binds the desired peptide epitope X in at least 10% of the plurality of sequence contexts, wherein the selected affinity reagent is selected from the group consisting of an antibody, an aptamer, a peptamer, and an antibody fragment.

2. The method of claim 1, wherein each of α and β consists of one amino acid.

3. The method of claim 1, wherein at least one of α and β further comprises a linker.

4. The method of claim 1, wherein at least one of α and β further comprises a modification selected from the group consisting of a N-terminal modification, a C-terminal modification, a positively-charged group, a negatively-charged group, a hydrophobic group, and a sugar.

5. The method of claim 1, wherein each of α and β consists of between one and three amino acids.

6. The method of claim 1, wherein the selected affinity reagent is the antibody.

7. The method of claim 1, further comprising:
Characterizing the binding of the selected affinity reagent by screening the selected affinity reagent against a plurality of peptides of the same length of the desired epitope.

8. The method of claim 7, wherein the plurality of peptides of the same length of the desired epitope is representative of at least 90% of all possible variations of peptides of the same length of the desired epitope.

9. The method of claim 1, further comprising:
characterizing the binding of the selected affinity reagent by screening the selected affinity reagent against a plurality of peptides, wherein each peptide of the plurality of peptides comprises the desired epitope and one or more flanking residues.

10. The method of claim 7, further comprising:
characterizing the binding of the selected affinity reagent by screening the selected affinity reagent against a second plurality of peptides, wherein each peptide of the plurality of peptides comprises a secondary epitope and one or more flanking residues.

11. The method of claim 1, further comprising:
characterizing the binding of the selected affinity reagent at least in part by screening the selected affinity reagent against a plurality of subsets of a plurality of peptides shorter than the desired peptide epitope.

12. The method of claim 1, further comprising characterizing the selected affinity reagent by screening the selected affinity reagent against a panel of proteins or peptides which contain the desired epitope.

13. The method of claim 1, wherein the selected affinity reagent binds to at least 20% of the plurality of sequence contexts.

14. The method of claim 1, further comprising characterizing the selected affinity reagent by screening the selected affinity reagent against a panel of proteins which do not contain the X epitope.

15. The method of claim 1, wherein the selected affinity reagent binds to at least 30% of the plurality of sequence contexts.

16. The method of claim 1, wherein the selected affinity reagent is screened against a library of random peptides having a length between 2 and 10 amino acids, and further comprising:
identifying the peptides bound by the selected affinity reagent; and
retaining the selected affinity reagent if 1) it binds less than twenty different epitopes and 2) it binds at least 10% of all peptides longer than 5 amino acids containing that epitope.

17. The method of claim 16, wherein the selected affinity reagent binds at least 15% of all peptides longer than 5 amino acids containing the epitope.

18. The method of claim 1, further comprising:
characterizing the binding of the affinity reagent by screening the affinity reagent against a library of peptides, the library of peptides comprising peptides shorter than the desired epitope, peptides of the same length of the desired epitope, and peptides longer than the desired epitope; and
identifying the sequences of bound peptides, thereby characterizing the binding of the affinity reagent.

19. The method of claim 1, wherein the selected affinity reagent is the aptamer.

20. The method of claim 1, wherein the selected affinity reagent is the peptamer.

21. The method of claim 1, wherein the selected affinity reagent is the antibody fragment.

22. The method of claim 1, wherein the peptide library is used in a denatured state to select said affinity reagent.

23. The method of claim 1, further comprising retaining the selected affinity reagent for further screening.

\* \* \* \* \*

UNITED STATES PATENT AND TRADEMARK OFFICE
CERTIFICATE OF CORRECTION

PATENT NO. : 11,970,693 B2  
APPLICATION NO. : 16/791456  
DATED : April 30, 2024  
INVENTOR(S) : Parag Mallick Page 1 of 1

It is certified that error appears in the above-identified patent and that said Letters Patent is hereby corrected as shown below:

In the Claims

Claim 1, Column 67, Line 62, change "each of a and comprises" to "each of α and β comprises".

Signed and Sealed this
Fifteenth Day of October, 2024

Katherine Kelly Vidal
*Director of the United States Patent and Trademark Office*